US008519131B2

(12) United States Patent
Matsunaga et al.

(10) Patent No.: US 8,519,131 B2
(45) Date of Patent: Aug. 27, 2013

(54) MODIFIED METAL COMPLEX AND USE THEREOF

(75) Inventors: Tadafumi Matsunaga, Tsukuba (JP); Nobuyoshi Koshino, Tsukuba (JP); Hideyuki Higashimura, Tsukuba (JP); Hiroshi Hamamatsu, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 596 days.

(21) Appl. No.: 12/530,174

(22) PCT Filed: Mar. 10, 2008

(86) PCT No.: PCT/JP2008/054329
§ 371 (c)(1),
(2), (4) Date: Sep. 4, 2009

(87) PCT Pub. No.: WO2008/111568
PCT Pub. Date: Sep. 18, 2008

(65) Prior Publication Data
US 2010/0105909 A1    Apr. 29, 2010

(30) Foreign Application Priority Data

Mar. 9, 2007  (JP) ................. 2007-061009
Mar. 28, 2007 (JP) ................. 2007-084345
Aug. 7, 2007  (JP) ................. 2007-205956

(51) Int. Cl.
*C07F 15/06* (2006.01)
*B01J 31/12* (2006.01)

(52) U.S. Cl.
USPC ........................................... 546/10; 502/167

(58) Field of Classification Search
USPC .................. 546/10; 313/504; 502/167
See application file for complete search history.

(56) References Cited

U.S. PATENT DOCUMENTS

| | | |
|---|---|---|
| 2009/0062110 A1 | 3/2009 | Koshino et al. |
| 2009/0318681 A1 | 12/2009 | Matsunaga et al. |
| 2010/0086823 A1 | 4/2010 | Koshino et al. |
| 2010/0105853 A1 | 4/2010 | Matsunaga et al. |
| 2010/0129698 A1 | 5/2010 | Okada et al. |
| 2011/0015059 A1 | 1/2011 | Matsunaga et al. |

FOREIGN PATENT DOCUMENTS

| | | |
|---|---|---|
| JP | 2006-035186 A | 2/2006 |
| WO | 2007/091616 A1 | 8/2007 |

OTHER PUBLICATIONS

Ya-Qiong Gong et al., "Syntheses, crystal structures and photoluminescence of two Cd(II) coordination polymers derived from a flexible bipyridyl ligand," Journal of Molecular Structure, vol. 705, No. 1-3, Nov. 1, 2004, pp. 29-34.

H. Olmez et al., "Spectrothermal Studies on Co(II), Ni(II), Cu(II) and Zn(II) Salicylato (1,10-Phenanthroline) Complexes," Journal of Thermal Analysis and Calorimetry, vol. 76, No. 3, Jun. 1, 2004, pp. 793-800.

J.-J. Zhang et al., "Preparation, Thermal Decomposition Process and Kinetics for Terbium p-Methoxybenzoate Ternary Complex with 1,10-Phenanthroline," Journal of Thermal Analysis and Calorimetry, vol. 79, No. 1, Jan. 1, 2005, pp. 181-186.

Jian Gao et al., "Structually Defined Catalysts for Enantioselective Oxidative Coupling Ractions", Angew. Chem. Int. Ed., 2003, pp. 6008-6012, No. 42.

Meenal D. Godbole et al., "Highly Efficient Disproportionation of Dihydrogen Peroxide: Synthesis, Structure, and Catalase Activity of Manganese Complexes of the Salicylimidate Ligand", Eur. J. Inorg. Chem., 2005, pp. 305-313.

Susumu Kitagawa et al., "Functional Porous Coordination Polymers", Angew. Chem. Ind. Ed., 2004, pp. 2334-2375, No. 43.

Fung Lam et al., "Synthesis of Dinucleating Phenanthroline-Based Ligands", Tetrahedron 55, 1999, pp. 8377-8384.

Fung Lam et al., "Synthesis of Acyclic Dinucleating Phenanthroline-Pyridine and Phenanthroline-Phosphine Ligands", Tetrahedron Letters, 1995, pp. 6261-6262, vol. 36, No. 35.

Zenghe Liu et al., "Schiff Base Complexes of Vanadium(III, IV, V) as Catalysts for the Electroreduction of $O_2$ to $H_2O$ in Acetonitrile", Inorg. Chem., 2001, pp. 1329-1333, No. 40.

Tatsuhiro Okada et al., "A Comparative Study of Organic Cobalt Complex Catalyst for Oxygen Reduction in Polymer Electrolyte Fuel Cells", Journal of Inorganic and Organometallic Polymers, 1999, pp. 199-219, vol. 9, No. 4.

Kagaku Sosetsu No. 34 Shokubai Sekkei, Japan Scientific Societies Press, Aug. 1, 1982, pp. 176-189.

Hisae Wada et al., "Di(phenoxo)-bridged Dinuclear $Mn_2$(II,II) and $Mn_2$(II,III) Complexes of Macrocyclic Ligands: Structure, Properties, and Catalase-Like Function", Bull. Chem. Soc. Jpn., 1995, pp. 1105-1114, No. 68.

Landon, Philip, et al., "Selective oxidation of CO in the presence of $H_2$, $H_2O$ and $CO_2$ via gold for use in fuel cells," Chem. Comm., 2005, pp. 3385-3387.

Pilkington, N. H., et al., "Complexes of Binucleating Ligands, III. Novel Complexes of a Macrocyclic Binucleating Ligand," Australian Journal of Chemistry, 1970, 23, pp. 2225-2236.

(Continued)

*Primary Examiner* — Charanjit Aulakh
(74) *Attorney, Agent, or Firm* — Sughrue Mion, PLLC

(57) ABSTRACT

A modified metal complex obtained by subjecting a metal complex containing an organic compound having one nitrogen-containing aromatic heterocycle and four or more structures of a phenol, thiophenol, aniline or nitrogen-containing aromatic heterocyclic ring or an organic compound having two or more phenol rings and three or more nitrogen-containing aromatic heterocycles, in its molecule as a ligand, to a heating, radiation irradiation or discharge treatment until a mass reduction rate after the treatment becomes from 1 to 90 mass %, thereby the complex shows a carbon content after the treatment of 5 mass % or more.

16 Claims, 7 Drawing Sheets

(56) References Cited

OTHER PUBLICATIONS

Woltinger, Jens, et al., "Zeolite-Encapsulated Cobalt Salophen Complexes as Efficient Oxygen-Activating Catalysts in Palladium-Catalyzed Aerobic 1,4-Oxidation of 1,3-Dienes," Chem. Euro. J., 1999, 5, pp. 1460-1467.

Japanese Office Action issued in JP Application No. 2008-060467, dated Jun. 11, 2013.

Maoqi Feng et al., "Synthesis and Reactivity of Nonbridged Metal-Metal Bonded Rhodium and Iridium Phenanthroline-Based $N_2O_2$ Dimers," Organometallics, 2002, vol. 21, No. 13, pp. 2743-2750.

So-Ngan Pun et al., "Iron(I) complexes of 2,9-bis(2-hydroxyphenyl)-1,10-phenanthroline($H_2$dophen) as electrocatalysts for carbon dioxide reduction. X-Ray crystal structures of [Fe(dophen)Cl]$_2$·2HCON(CH$_2$)$_2$ and [Fe(dophen)(N-Melm)$_2$]ClO$_4$(N-Melm = 1-methylimidazole)," Journal of the Chemical Society, Dalton Transactions, 2002, vol. 2002, pp. 575-583.

Danielle M. Goken et al., "Alkylation of [2,2'-([2,2'-bipyridine]-6,6'-diyl)bis[phenolato]-N,N',O,O']nickel(II) during catalytic reduction of 1-iodooctane," Journal of Electroanalytical Chemistry, 2004, vol. 564, pp. 123-132.

Wan-Hung Chung et al., "Electrocarboxylation of arylmethyl chlorides catalyzed by cobalt 6,6'-bis(2-hydroxyphenyl)-2,2'-bipyridine," Journal of Electroanalytical Chemistry, 2000, vol. 486, No. 1, pp. 32-39.

MODIFIED METAL COMPLEX AND USE THEREOF

TECHNICAL FIELD

The present invention relates to a modified metal complex showing high stability against an acid or heating. Further, the present invention relates to a modified metal complex suitable as a catalyst. Furthermore, the present invention relates to a catalyst using the modified metal complex.

BACKGROUND ART

Metal complexes each act as a catalyst in a redox reaction (redox catalyst) involving electron transfer such as an oxygenation reaction, an oxidative coupling reaction, a dehydrogenation reaction, a hydrogenation reaction, or an oxide decomposition reaction, and are each used in the production of an organic compound or polymer compound. Further, the metal complexes are used in various uses including additives, modifiers, cells, and sensor materials. It has been known that these metal complexes exhibit excellent catalyst activity as an oxygen-reduction catalyst and hydrogen peroxide decomposition catalyst (see Z. Liu, F. C. Anson, Inorganic Chemistry, 40, 1329 (2001); and M. D. Godbole et al., European Journal of Inorganic Chemistry, 305 (2005)).

However, when any such metal complex as described above is used as a redox catalyst, the thermal stability and chemical stability of the complex are insufficient, so the use of the catalyst upon performance of a reaction in the presence of an acid or under heating involves a problem. Accordingly, an improvement in stability of a metal complex catalyst against the presence of an acid or heating in a reaction to which the catalyst is applied has been aspired.

A method of subjecting a metal complex to a heating treatment has been described in Tatsuhiro Okada, et. al., Journal of Inorganic and Organometallic Polymers, 9, 199, (1999) as a method of improving the stability of the metal complex. However, the reaction activity of such catalyst as described in the document is not enough for the catalyst to be put into practical use, so an additional improvement of the reaction activity has been demanded.

In addition, the following fact has been known particularly about an assembled metal complex out of the metal complexes: when the metal complexes are assembled, a specific reaction space is provided, so the reaction rate of a redox reaction can be increased, or the reaction selectivity can be controlled (see, for example, Susumu Kitagawa, Ryo Kitaura, Shin-ichiro Noro, Angewandte Chemie International Edition, 43, 2334 (2004)).

It is known that, among the metal complexes, those having a transition metal atom as their center metals exhibit excellent reaction activity as a hydrogen peroxide decomposition catalyst or an oxidative coupling reaction catalyst (see Bulletin of Chemical Society of Japan, 68, 1105 (1995); and Angewandte Chemie International Edition, 42, 6008 (2003)).

However, the stability of the metal complex described in Bulletin of Chemical Society of Japan, 68, 1105 (1995) or Angewandte Chemie International Edition, 42, 6008 (2003) is insufficient in stability, having trouble with the use of the catalyst particularly when the reaction is run in the presence of an acid or when the reaction is run under heating. For this, it has been desired to improve the stability of the metal complex catalyst against the presence of an acid or heating in order to use the metal complex as a catalyst.

DISCLOSURE OF INVENTION

According to the present invention, there can be provided a modified metal complex excellent in thermal stability.

Further, according to the present invention, there can be provided a modified metal complex having high reaction activity as a redox catalyst, and being excellent in thermal stability.

According to the present invention, there is provided the following means:

(1) A modified metal complex obtained by the step of subjecting a metal complex comprising an organic compound having one nitrogen-containing aromatic heterocycle and four or more structures selected from the group consisting of a phenol ring, a thiophenol ring, an aniline ring and a nitrogen-containing aromatic heterocycle in its molecule as a ligand to any one treatment of a heating treatment, a radiation irradiation treatment and a discharge treatment until a mass reduction rate after the treatment becomes 1 mass % or more and 90 mass % or less, thereby the complex shows a carbon content after the treatment of 5 mass % or more.

(2) A modified metal complex obtained by the step of subjecting a metal complex comprising an organic compound having two or more phenol rings and three or more nitrogen-containing aromatic heterocycles in its molecule as a ligand to any one treatment of a heating treatment, a radiation irradiation treatment and a discharge treatment until a mass reduction rate after the treatment becomes 1 mass % or more and 90 mass % or less, thereby the complex shows a carbon content after the treatment of 5 mass % or more.

(3) The modified metal complex described in (1) or (2), wherein the metal complex comprises transition metal atom(s) belonging to Period 4 to Period 6 in the periodic table.

(4) The modified metal complex described in any one of (1) to (3), wherein the number of metal atoms contained in the metal complex is 1 to 10.

(5) The modified metal complex described in any one of (1) to (4), wherein the ligand is a ligand represented by formula (I):

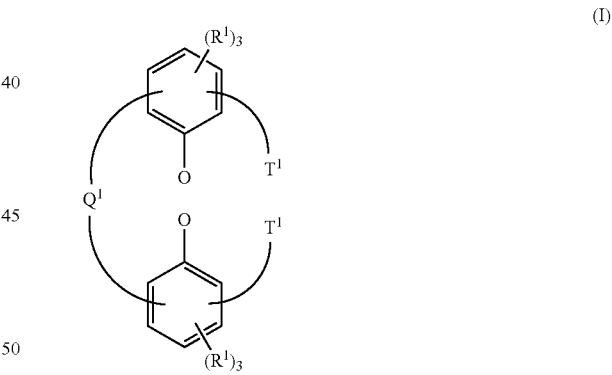

wherein $R^1$ represents a hydrogen atom or a substituent; two $R^1$'s bonded to two adjacent atoms may be coupled with each other, and $R^1$'s may be same as or different from each other; $Q^1$ represents a divalent organic group having at least one nitrogen-containing aromatic heterocycle; $T^1$ represents a monovalent organic group having at least one nitrogen-containing aromatic heterocycle, and two $T^1$'s may be same as or different from each other; and it should be noted that the charge is omitted.

(6) The modified metal complex described in any one of (1) to (3), which is a polymer comprising a residue of the ligand represented by formula (I).

(7) The modified metal complex described in (6), which is a polymer comprising the residue of the ligand represented by formula (I) as a repeating unit.

(8) The modified metal complex described in any one of (1) to (7), comprising nitrogen atom(s) and oxygen atom(s) as ligand atoms.
(9) The modified metal complex described in any one of (1) to (8), which is obtained by heating the metal complex at a temperature of 250° C. or higher and 1,200° C. or lower.
(10) The modified metal complex described in any one of (1) to (9), wherein the metal complex has an absorption local maximum in a range of 1,500 to 1,600 cm$^{-1}$ in a spectrum measured by laser Raman spectrometry at an excitation wavelength of 532 nm.
(11) A modified metal complex obtained by the step of subjecting a mixture of the metal complex before the treatment specified in (1) or (2), and a carbon carrier or at least one organic compound selected from an organic compound having a boiling point or melting point of 250° C. or higher and an organic compound having a thermal polymerization initiation temperature of 250° C. or lower, to any modification treatment of a heating treatment, a radiation irradiation treatment and a discharge treatment until a mass reduction rate after the modification treatment becomes 1 mass % or more and 90 mass % or less, thereby the complex shows a carbon content after the modification treatment of 5 mass % or more.
(12) A modified metal complex obtained by the step of subjecting a composition comprising the metal complex before the treatment specified in (1) or (2), and a carbon carrier and/or a conductive polymer, to a heating treatment, a radiation irradiation treatment or a discharge treatment.
(13) A catalyst, comprising the modified metal complex according to any one of (1) to (12).
(14) A carbon compound, which is a metal complex comprising a heteroatom as a ligand atom,
wherein the carbon compound has one or more other peaks at a distance of 0.58 Å or less from a peak derived from a first adjacent atom observed in the range of 1.0 Å or more to 2.5 Å or less in the extended X-ray absorption fine structure (EXAFS) radial distribution function of the central metal of the metal complex.
(15) The carbon compound according to (14), which has an absorption local maximum in a range of 1,500 to 1,600 cm$^{-1}$ in a spectrum determined by laser Raman spectroscopy at an excitation wavelength of 532 nm.
(16) A catalyst, comprising the carbon compound according to (14) or (15).
(17) A modified metal complex obtained by the step of subjecting a mononuclear complex, comprising an organic compound having one nitrogen-containing aromatic heterocycle, one phenol ring, and one or two structures selected from the group consisting of a phenol ring, a thiophenol ring and a nitrogen-containing aromatic heterocycle in its molecule as a ligand, to any modification treatment of a heating treatment, a radiation irradiation treatment and a discharge treatment until a mass reduction rate after the modification treatment becomes 1 mass % or more and 90 mass % or less, thereby the complex shows a carbon content after the modification treatment of 5 mass % or more.
(18) A modified metal complex obtained by the step of subjecting a mononuclear complex, comprising an organic compound having two phenol rings and one or two nitrogen-containing aromatic heterocycles in its molecule as a ligand, to any modification treatment of a heating treatment, a radiation irradiation treatment and a discharge treatment until a mass reduction rate after the modification treatment becomes 1 mass % or more and 90 mass % or less, thereby the complex shows a carbon content after the modification treatment of 5 mass % or more.
(19) The modified metal complex described in (17) or (18), wherein the mononuclear complex comprises a transition metal atom belonging to Period 4 to Period 6 in the periodic table.
(20) The modified metal complex described in any one of (17) to (19), wherein the ligand is a ligand represented by formula (XI) or (XII):

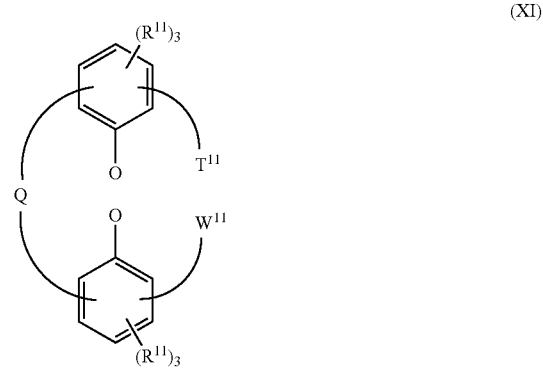

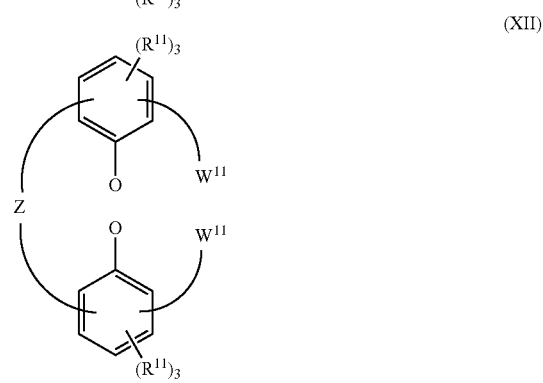

wherein $R^{11}$ represents a hydrogen atom or a substituent; two adjacent $R^{11}$'s may be coupled with each other, and $R^{11}$'s may be same as or different from each other; Q represents a divalent organic group comprising one nitrogen-containing aromatic heterocycle; Z represents a divalent organic group comprising one or two nitrogen-containing aromatic heterocycles; $T^{11}$ represents a nitrogen-containing aromatic heterocycle; $W^{11}$ represents a nitrogen-free, monovalent aromatic substituent or a hydrogen atom; when $W^{11}$'s are present, the $W^{11}$'s may be same as or different from each other; and it should be noted that the charges are omitted.
(21) The modified metal complex described in any one of (17) to (20), wherein the mononuclear complex comprises the nitrogen atom and the oxygen atom as a ligand atom.
(22) The modified metal complex described in any one of (17) to (21), which is obtained by heating the mononuclear complex at a temperature of 250° C. or higher and 1,200° C. or lower.
(23) A modified metal complex obtained by the step of subjecting a mixture of the mononuclear complex used in (17) or (18), and a carbon carrier or at least one organic compound selected from an organic compound having a boiling point or melting point of 250° C. or higher and an organic compound having a thermal polymerization initiation temperature of 250° C. or lower, to any modification treatment of a heating treatment, a radiation irradiation treatment and a discharge treatment until a mass reduction rate after the modification treatment becomes 1 mass % or more and 90 mass % or less, thereby the complex shows a carbon content after the modification treatment of 5 mass % or more.

(24) A modified metal complex obtained by the step of subjecting a composition comprising the metal complex used in (17) or (18) and a carbon carrier and/or a conductive polymer, to a heating treatment, a radiation irradiation treatment or a discharge treatment.

(25) A catalyst, comprising the modified metal complex according to any one of (17) to (24).

(26) An electrode catalyst, comprising the modified metal complex according to any one of (17) to (24).

Hereinafter, a first embodiment of the present invention means to include the modified metal complexes described in the items (1) to (12) above, the catalyst described in the item (13) above, the carbon compounds described in the items (14) to (15) above, and the catalyst described in the item (16) above.

A second embodiment of the present invention means to include the modified metal complexes described in the items (17) to (24) above, the catalyst described in the item (25) above, and the electrode catalyst described in the item (26) above.

Herein, the present invention means to include all of the above first and second embodiments, unless otherwise specified.

Other and further features and advantages of the invention will appear more fully from the following description, appropriately referring to the accompanying drawings.

BEST MODE FOR CARRYING OUT THE INVENTION

Figure 1:
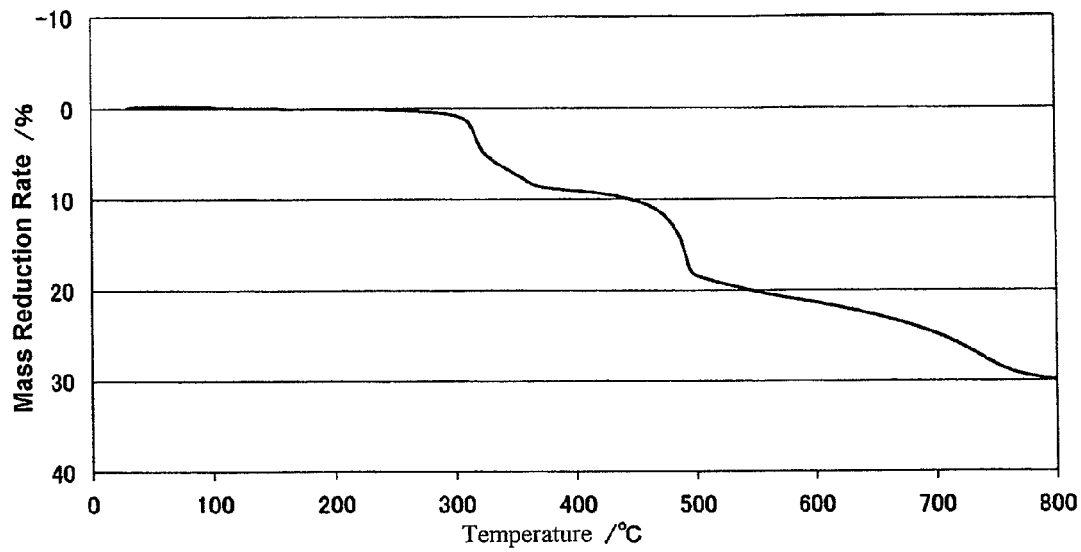
FIG. 1 shows a thermogravimetric analysis chart of the metal complex (A).
Figure 2:
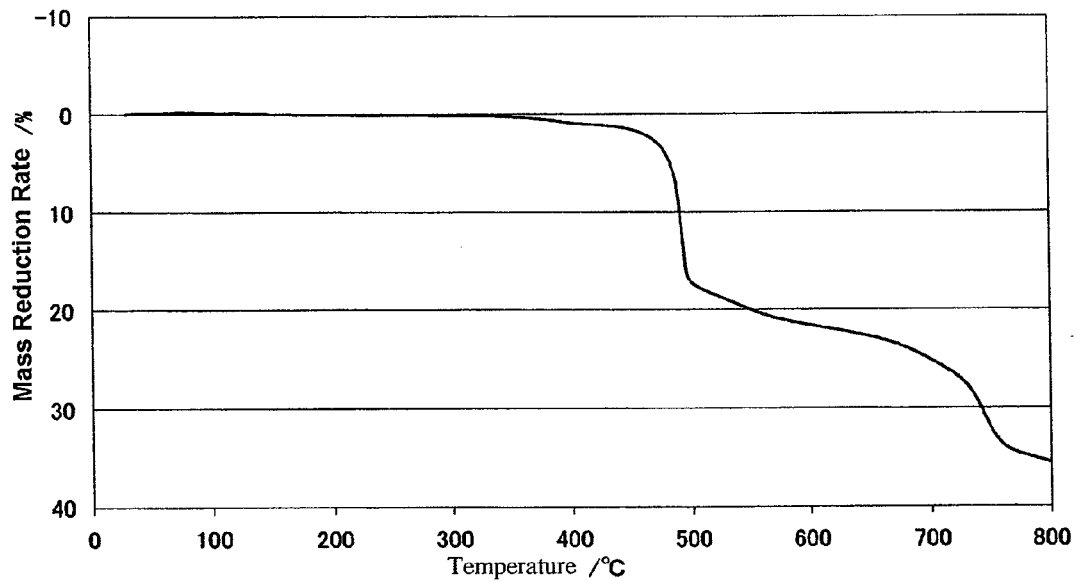
FIG. 2 shows a thermogravimetric analysis chart of the metal complex (B).
Figure 3:
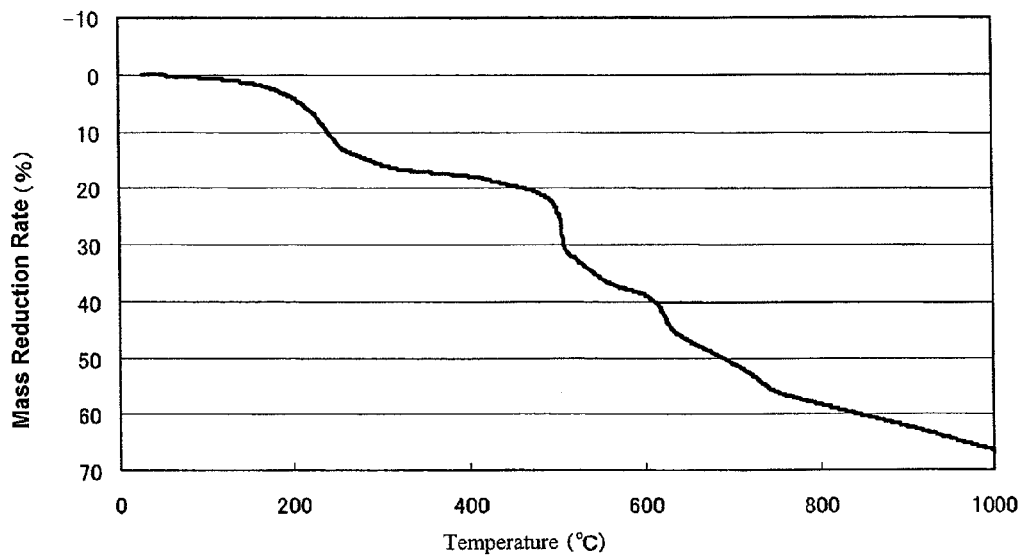
FIG. 3 shows a thermogravimetric analysis chart of the metal complex (D).
Figure 4:
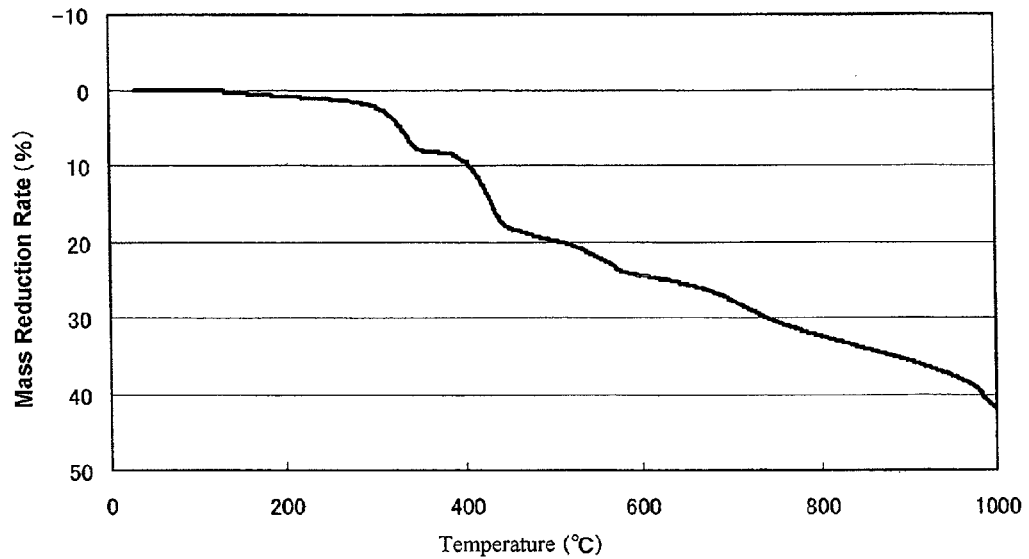
FIG. 4 shows a thermogravimetric analysis chart of the metal complex (E).

First, the first embodiment of the present invention will be described.

A ligand of a metal complex applied to the first embodiment of the present invention is an organic compound having one nitrogen-containing aromatic heterocycle and four or more structures each selected from a phenol ring, a thiophenol ring, an aniline ring, and a nitrogen-containing aromatic heterocycle. Specific structures of the organic compound are exemplified in formulae (a) to (e).

It should be noted that the charges are omitted.

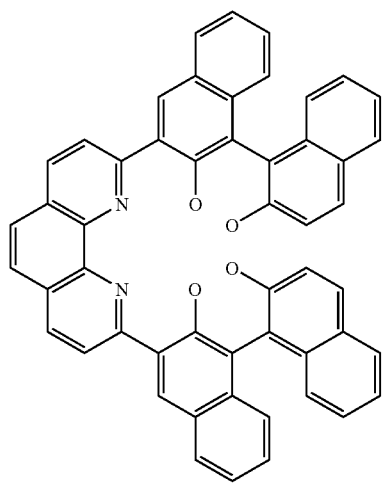

(a)

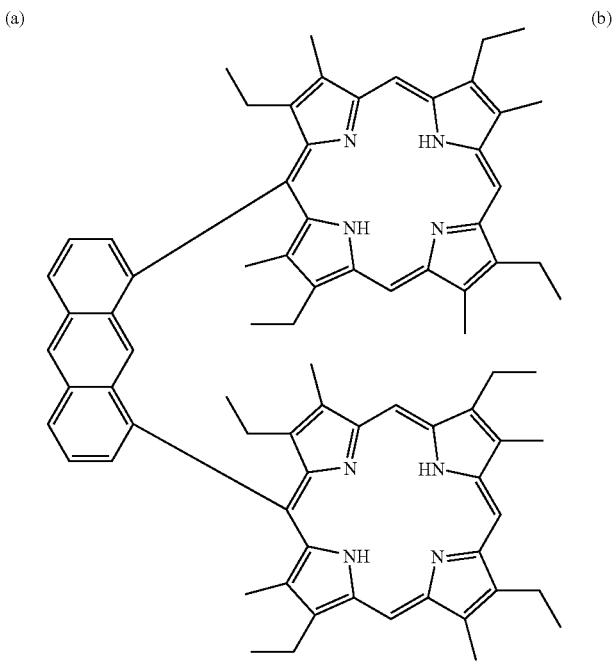

(b)

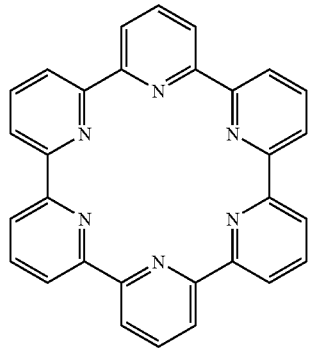

(c)

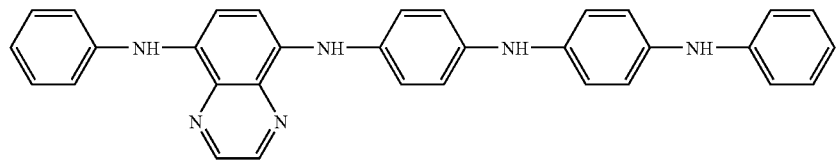

(d)

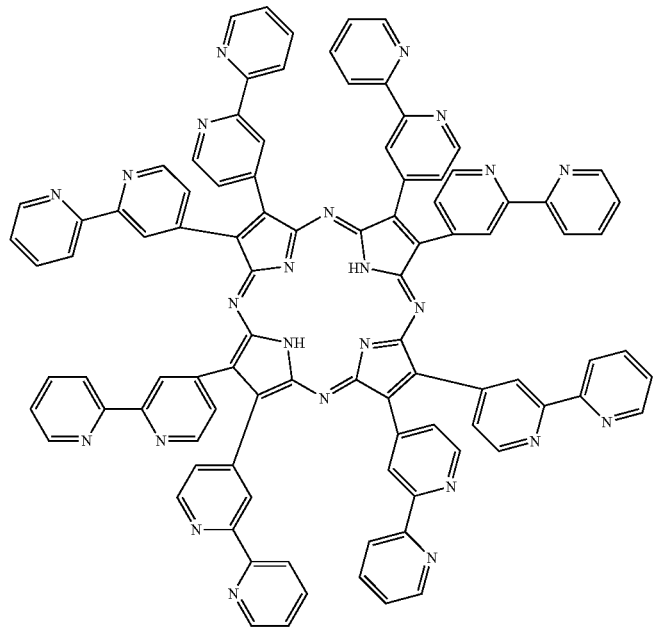

(e)

The term "nitrogen-containing aromatic heterocycle" as used herein refers to an aromatic group as a compound structure satisfying at least the following condition: the structure has an aromatic heterocyclic structure containing at least one nitrogen atom in its ring. The atoms of which the ring system is constituted may include a heteroatom such as an oxygen atom or a sulfur atom in addition to carbon and nitrogen. Specific examples of the nitrogen-containing aromatic heterocycle include groups having, as a basic structure, pyridine, pyrazine, pyridazine, pyrimidine, pyrrole, triazole, pyrazole, thiazole, oxazole, imidazole, indole, benzoimidazole, phenanthroline, carbazole, quinoline, isoquinoline, cinnoline, phthalazine, quinazoline, quinoxaline, benzodiazine, or the like. Note that phenanthroline has two nitrogen-containing aromatic heterocycles. One or more proton may be released from a hydroxyl group (OH), a sulfhydryl group (SH), and an amino group.

In addition, the term "phenol ring" refers to an aromatic group as a compound structure satisfying at least the following condition: the structure has a benzene ring structure to which at least one hydroxy group (OH) is bonded. The term "thiophenol ring" refers to an aromatic group as a compound structure satisfying at least the following condition: the structure has a benzene ring structure to which at least one sulfhydryl group (SH) is bonded. The term "aniline ring" refers to an aromatic group as a compound structure satisfying at least the following condition: the structure has a benzene ring structure to which at least one amino group is bonded.

Specific examples of the aromatic groups as a compound structure satisfying at least the condition that the structure has a benzene ring structure include: aromatic hydrocarbons such as benzene, naphthalene, indene, biphenylene, acenaphthylene, fluorene, phenalene, phenanthrene, anthracene, fluoranthene, acephenanthrylene, aceanthrylene, triphenylene, pyrene, chrysene, naphthacene, picene, perylene, pentacene, tetraphenylene, hexacene, and coronene; and groups having, as a basic structure, a fused heterocyclic compound containing an oxygen and sulfur elements, such as benzothiophene, benzofuran, and xanthene. Preferred is a group of an aromatic hydrocarbon and more preferred is a group obtained from benzene, naphthalene, indene, biphenylene, acenaphthylene, fluorene, and phenanthrene.

Further, the organic compound as a ligand more preferably has two or more phenol rings, three or more nitrogen-containing aromatic heterocycles, and two or more phenol rings. The use of a ligand having such structure improves the stability. The number of nitrogen-containing aromatic heterocycles is preferably 3 to 8, more preferably 3 to 5, and particularly preferably 3 or 4. In addition, the number of phenol rings is preferably 2 to 6, more preferably 2 to 4, and particularly preferably 2.

The ligand of the metal complex before a modification treatment used in the first embodiment of the present invention is more preferably, for example, an organic compound represented by formula (I). It should be noted that the charge is omitted.

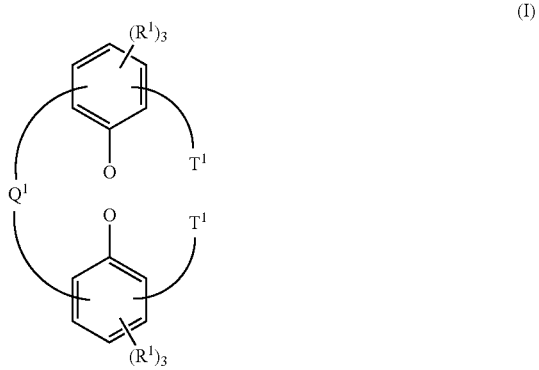

In formula (I), $R^1$ represents a hydrogen atom or a substituent; two $R^1$'s bonded to two adjacent atoms may be coupled with each other; $R^1$'s may be same as or different from each other; $Q^1$ represents a divalent organic group having at least one nitrogen-containing aromatic heterocycle; $T^1$ represents a monovalent organic group having at least one nitrogen-containing aromatic heterocycle; and two $T^1$'s may be same as or different from each other.

When $R^1$ in formula (I) is a substituent, examples of the substituent include a hydroxyl group, an amino group, a nitro group, a cyano group, a carboxyl group, a formyl group, a hydroxysulfonyl group, a halogen atom, a monovalent hydrocarbon group which may be substituted, a hydrocarbyloxy group which may be substituted (hydrocarbon oxy group which may be substituted), an amino group substituted with two monovalent hydrocarbon groups which may be unsubstituted or substituted (namely, hydrocarbon disubstituted amino group which may be substituted), a hydrocarbylmercapto group which may be substituted (hydrocarbon mercapto group which may be substituted), a hydrocarbylcarbonyl group which may be substituted (hydrocarbon carbonyl group which may be substituted), a hydrocarbyloxycarbonyl group which may be substituted (hydrocarbon oxycarbonyl group which may be substituted), an aminocarbonyl group substituted with two monovalent hydrocarbon groups which may be unsubstituted or substituted (namely, hydrocarbon disubstituted aminocarbonyl group which may be substituted) and a hydrocarbyloxysulfonyl group which may be substituted (hydrocarbon sulfonyl group which may be substituted). Among these groups, a monovalent hydrocarbon group which may be substituted, a hydrocarbyloxy group which may be substituted, an amino group substituted with two monovalent hydrocarbon groups which may be unsubstituted or substituted, a hydrocarbylmercapto group which may be substituted, a hydrocarbylcarbonyl group which may be substituted and a hydrocarbyloxycarbonyl group which may be substituted are preferable, a monovalent hydrocarbon group which may be substituted, a hydrocarbyloxy group which may be substituted and an amino group substituted with two monovalent hydrocarbon groups which may be unsubstituted or substituted are more preferable, and a monovalent hydrocarbon group which may be substituted and a hydrocarbyloxy group which may be substituted are even more preferable. In these groups, a nitrogen atom to which a hydrogen atom is bonded is preferably substituted with a monovalent hydrocarbon group. Further, when the group represented by $R^1$ has more than one substituents, two substituents may be combined to form a ring.

Examples of the monovalent hydrocarbon group represented by the above $R^1$ include alkyl groups having 1 to 50 carbon atoms (preferably, alkyl groups having 1 to 20 carbon atoms) such as a methyl group, an ethyl group, a propyl group, an isopropyl group, a butyl group, an isobutyl group, a tert-butyl group, a pentyl group, a hexyl group, a nonyl group, a dodecyl group, a pentadecyl group, an octadecyl group and a docosyl group; cyclic saturated hydrocarbon groups having 3 to 50 carbon atoms (preferably, cyclic saturated hydrocarbon groups having 3 to 20 carbon atoms) such as a cyclopropyl group, a cyclobutyl group, a cyclopentyl group, a cyclohexyl group, a cyclononyl group, a cyclododecyl group, a norbornyl group and an adamantyl group; alkenyl groups having 2 to 50 carbon atoms (preferably, alkenyl groups having 2 to 20 carbon atoms) such as an ethenyl group, a propenyl group, a 3-butenyl group, a 2-butenyl group, a 2-pentenyl group, a 2-hexenyl group, a 2-nonenyl group and 2-dodecenyl group; aryl groups having 6 to 50 carbon atoms (preferably, aryl groups having 6 to 20 carbon atoms) such as a phenyl group, a 1-naphthyl group, a 2-naphthyl group, a 2-methylphenyl group, a 3-methylphenyl group, a 4-methylphenyl group, a 4-ethylphenyl group, a 4-propylphenyl group, a 4-isopropylphenyl group, a 4-butylphenyl group, a 4-tert-butylphenyl group, a 4-hexylphenyl group, a 4-cyclohexylphenyl group, a 4-adamantylphenyl group and a 4-phenylphenyl group; and aralkyl groups having 7 to 50 carbon atoms (preferably, aralkyl groups having 7 to 20 carbon atoms) such as a phenylmethyl group, a 1-phenylethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl group, a 5-phenyl-1-pentyl group and a 6-phenyl-1-hexyl group.

As the monovalent hydrocarbon group represented by $R^1$, hydrocarbon groups having 1 to 20 carbon atoms are preferable, hydrocarbon groups having 1 to 12 carbon atoms are more preferable, hydrocarbon groups having 2 to 12 carbon atoms are even more preferable, hydrocarbon groups having 1 to 10 carbon atoms are even more preferable, and hydrocarbon groups having 3 to 10 carbon atoms are even more preferable.

The hydrocarbyloxy, hydrocarbylmercapto, hydrocarbylcarbonyl, hydrocarbyloxycarbonyl and hydrocarbylsulfonyl group respectively represented by $R^1$ are groups obtained by bonding one of the aforementioned monovalent hydrocarbon groups to an oxy, mercapto, carbonyl, oxycarbonyl and sulfonyl group, respectively.

The "amino group substituted with two monovalent hydrocarbon groups which may be unsubstituted or substituted" and "aminocarbonyl group substituted with two monovalent hydrocarbon groups which may be unsubstituted or substituted" represented by R¹ are groups in which two hydrogen atoms in an amino group and aminocarbonyl group (namely, —C(=O)—NH₂) are respectively substituted with the aforementioned monovalent hydrocarbon group. Specific examples and preferable examples of monovalent hydrocarbon groups contained therein are the same as monovalent hydrocarbon groups represented by R¹.

In the monovalent hydrocarbon group, hydrocarbyloxy group, hydrocarbylmercapto group, hydrocarbylcarbonyl group, hydrocarbyloxycarbonyl group and hydrocarbylsulfonyl group represented by R¹, a part or all of the hydrogen atoms contained in these groups may be substituted with, for example, a halogen atom, a hydroxyl group, an amino group, a nitro group, a cyano group, a monovalent hydrocarbon group which may be substituted, a hydrocarbyloxy group which may be substituted, a hydrocarbylmercapto group which may be substituted, a hydrocarbylcarbonyl group which may be substituted, a hydrocarbyloxycarbonyl group which may be substituted and a hydrocarbylsulfonyl group which may be substituted.

Among the above R¹'s, a particularly preferable one is a hydrogen atom, a methyl group, an ethyl group, a propyl group, an isopropyl group, a butyl group, an isobutyl group, a tert-butyl group, a phenyl group, a methylphenyl group and a naphthyl group.

Q¹ in formula (I) is a divalent organic group having at least one nitrogen-containing aromatic heterocycle. Specific examples thereof include a pyridylene group, a pyrazilene group, a pyrimidylene group, a pyridazilene group, a pyrolylene group, a thiazolylene group, an imidazolylene group, an oxazolylene group, a triazolylene group, an indolylene group, a benzoimidazolylene group, a benzofurylene group, a benzothienylene group, a quinolylene group, an isoquinolylene group, a cinnolilene group, a phthalazilene group, a quinazolilene group, a quinoxalilene group, a benzodiazilene group, a 1,10-phenanethrolyene group, a 2,2'-bipyridylene group, a 2,2'-bithiophenylene group, a 2,2'-bipyrrolene group, a 2,2'-bithiazolylene group, a 2,2'-bifurylene group, a 2,2'-bipyrimidylene group, a 2,2'-bipyridazilene group and a 2,2'-biimidazolylene group. Q¹¹ is preferably a pyridylene group, a pyrazilene group, a pyrimidylene group, a pyridazilene group, a pyrolylene group, a 1,10-phenanethrolyene group, a 2,2'-bipyridylene group, a 2,2'-bithiophenylene group, a 2,2'-bipyrrolene group, a 2,2'-bithiazolylene group, a 2,2'-bifurylene group, a 2,2'-bipyrimidylene group, a 2,2'-bipyridazilene group and a 2,2'-biimidazolylene group, a and more preferably a 1,10-phenanethrolyene group, a 2,2'-bipyridylene group, a 2,2'-bipyrrolene group, a 2,2'-bithiazolylene group and a 2,2'-biimidazolylene group.

Also, these groups may be further substituted with substituents in the above R¹.

T¹ represents a nitrogen-containing aromatic heterocyclic group which may be substituted. Specific examples of the nitrogen-containing aromatic heterocyclic group include a pyridyl group, a pyrazyl group, a pyrimidyl group, a pyridazyl group, a pyrrolyl group, a pyrazolyl group, a thiazolyl group, an imidazolyl group, an oxazolyl group, a triazolyl group, an indolyl group, a benzoimidazolyl group, a quinolyl group, an isoquinolyl group, a cinnolyl group, a phthalazyl group, a quinazolyl group, a quinoxalyl group, and a benzodiazyl group.

Preferred are a pyridyl group, a pyrazyl group, pyridazyl group, a pyrrolyl group, a pyrazolyl group, a pyridazyl group, a thiazolyl group, an indolyl group, and a benzoimidazolyl group. More preferred are a pyridyl group, a pyrrolyl group, a pyrazolyl group, a pyridazyl group, and a thiazolyl group.

Also, these groups may be further substituted with substituents in the above R¹.

The ligand represented by formula (I) is preferably a ligand having a structure represented by formula (II).

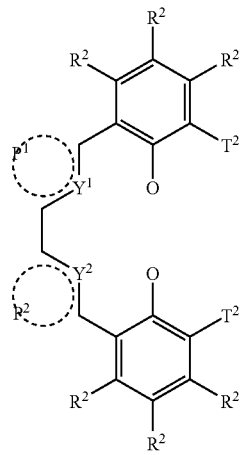

(II)

(In formula (II), R² has the same meaning as that of R¹ in formula (I); two R²'s bonded to two adjacent atoms may be coupled with each other; and R²'s may be same as or different from each other. Y¹ and Y² each represent any one of the following groups.

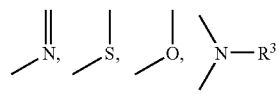

(R³ represents a hydrogen atom or a hydrocarbon group having 1 to 4 carbon atoms.)

P¹ represents a group of atoms necessary for forming a heterocyclic ring together with Y¹ and the two carbon atoms at a position adjacent to Y¹; P² represents a group of atoms necessary for forming a heterocyclic ring together with Y² and the two carbon atoms at a position adjacent to Y²; and P¹ and P² may be further bonded to each other to form a ring. T² has the same meaning as that of T¹ in formula (I); and it should be noted that the charge is omitted.)

In formula (II), Y¹ and Y² each represent any one of the following groups.

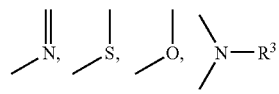

(R³ represents a hydrogen atom or a hydrocarbon group having 1 to 4 carbon atoms.)

P¹ represents a group of atoms necessary for forming a nitrogen-containing aromatic heterocyclic ring together with Y¹ and the two carbon atoms at a position adjacent to Y¹; P² represents a group of atoms necessary for forming a nitrogen-containing aromatic heterocyclic ring together with Y² and the two carbon atoms at a position adjacent to Y²; and P¹ and P² may be further bonded to each other to form a ring. Specific examples of the nitrogen-containing aromatic heterocycle include pyridine, pyrazine, pyrimidine, pyrrole, N-alkylpyrrole, thiazole, imidazole, oxazole, isoquinoline, and quinazoline. Those may be substituted by $R^1$ above. Preferred are pyridine, pyrazine, pyrimidine, pyrrole, N-alkylpyrrole, thiazole, imidazole, and oxazole, and more preferred are pyridine, pyrazine, pyrimidine, pyrrole, N-alkylpyrrole, and imidazole. Each of those groups may be further substituted with a substituent represented by $R^1$. The alkyl group of N-alkylpyrrole is preferably a methyl group or an ethyl group, or more preferably a methyl group.

In addition, the $P^1$ and $P^2$ structure may be bonded to each other to form a new ring, and the ring preferably has a structure represented by any one of formulae (III-1) to (III-6), and more preferably has a structure represented by any one of formulae (III-1) to (III-3).

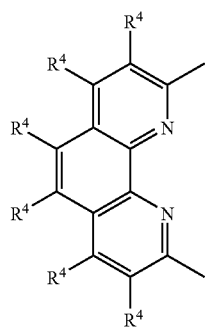

(III-1)

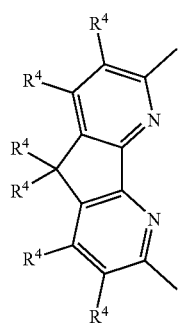

(III-2)

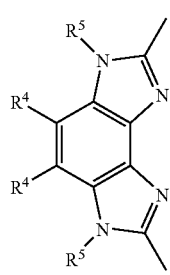

(III-3)

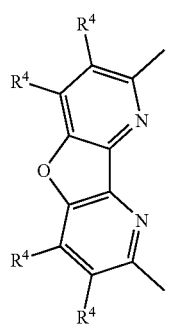

(III-4)

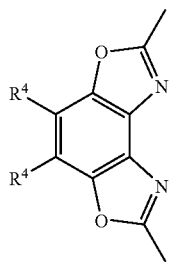

(III-5)

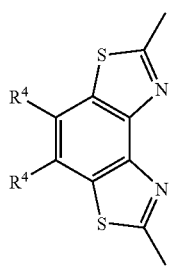

(III-6)

(In formulae (III-1) to (III-6), $R^4$ has the same meaning as that of $R^1$ in formula (I); $R^4$'s may be the same or different from each other; $R^5$ represents a hydrogen atom or a hydrocarbon group having 1 to 30 carbon atoms; and $R^5$'s may be the same or different from each other.)

$R^5$ preferably represents a hydrogen atom or a hydrocarbon group represented by 1 to 8 carbon atoms. Specific examples thereof include a methyl group, an ethyl group, a propyl group, an isopropyl group, a butyl group, an isobutyl group, a t-butyl group, a hexyl group, a phenyl group, and an octyl group.

The ligand in the metal complex preferably has 5 to 15 ligand atoms each of which is capable of bonding to the metal atom by coordination bond. Here, the coordinating atoms are, as described in page 966, Ryogo KUBO et al., Encyclopedia of Physics and Chemistry 4th ed. (issued on Jan. 10, 1991, Iwanami Shoten), atoms having unshared electron pairs to donate electrons to an unoccupied orbital of the metal atoms and bonded with the metal atoms by coordination bond.

The total number of coordinating atoms in the ligand is preferably 5 to 12, more preferably 6 to 10, and particularly preferably 6 to 8. Further, the coordinating atoms may be electrically neutral or charged ions.

The coordinating atom preferably is selected from a nitrogen atom, an oxygen atom, a phosphorus atom and a sulfur atom and coordinating atoms may be the same or different from each other. They are more preferably selected from a nitrogen atom, an oxygen atom, and a sulfur atom; and particularly preferably selected from a nitrogen atom and an oxygen atom.

Here, as the ligand having the structure represented by formula (II), ligands represented by the following formulae (IV-1) to (IV-18) are given as examples. Among these ligands, ligands represented by the formulae (IV-1) to (IV-12) are preferable, and ligands represented by the formulae (IV-1) to (IV-6) are particularly preferable. It should be noted that the charges are omitted.

(IV-1)
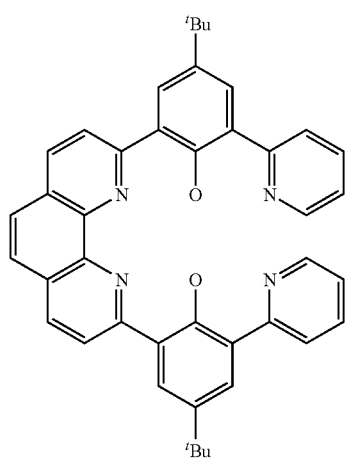
(IV-4)
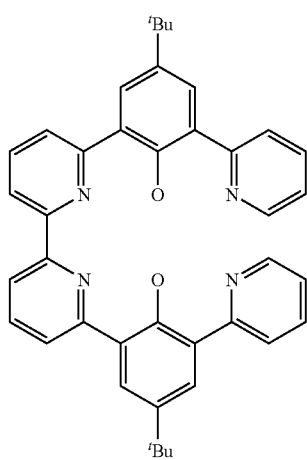
(IV-2)
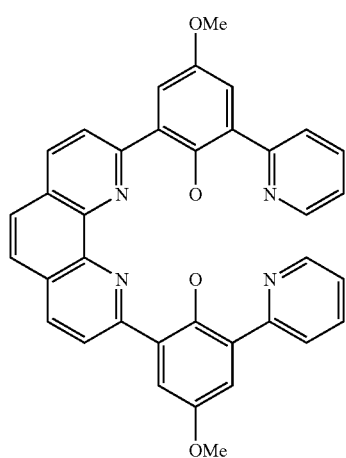
(IV-5)
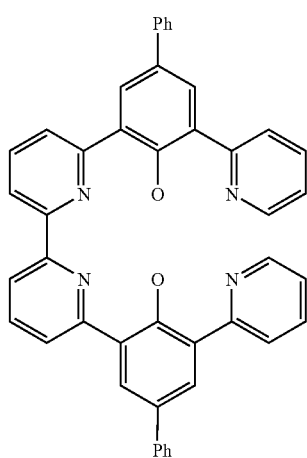
(IV-3)
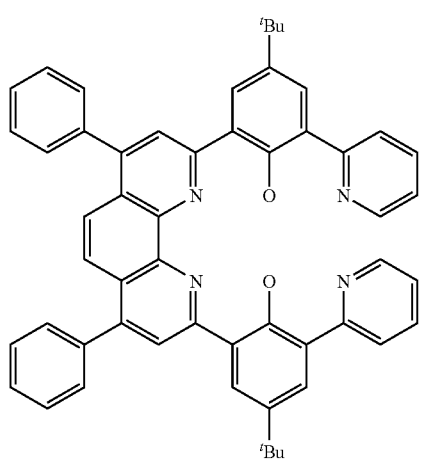
(IV-6)
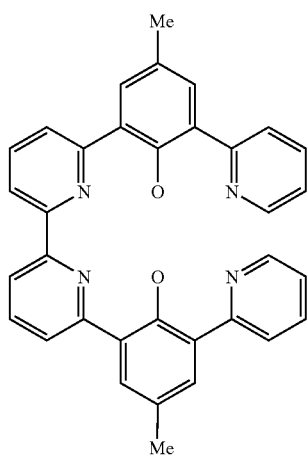

(IV-7)
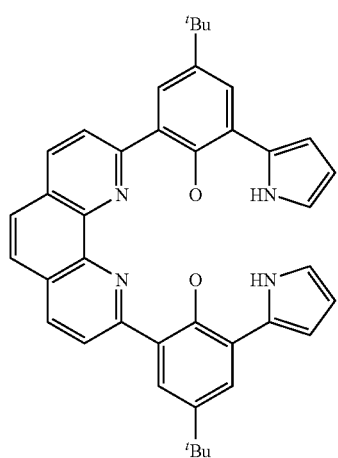
(IV-8)
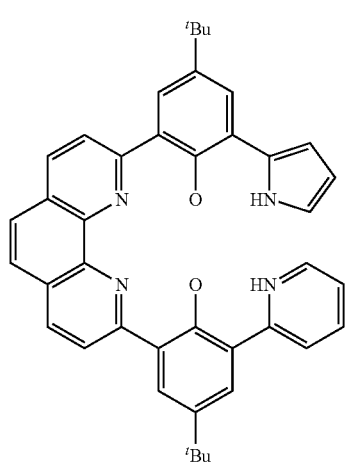
(IV-9)
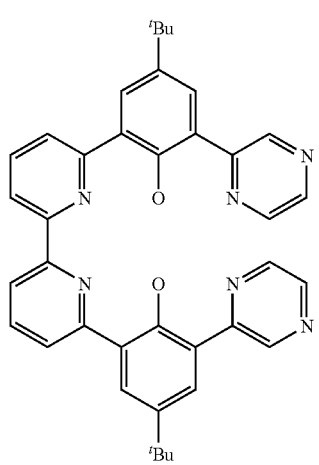
(IV-10)
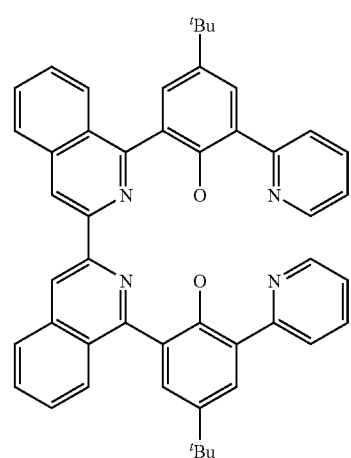
(IV-11)
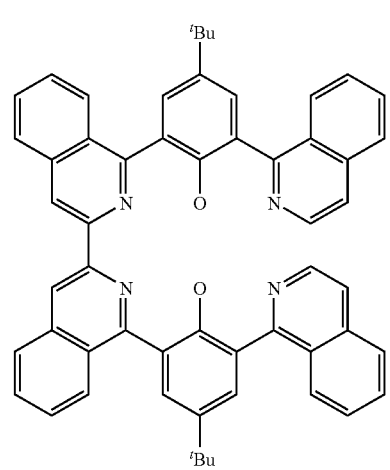
(IV-12)
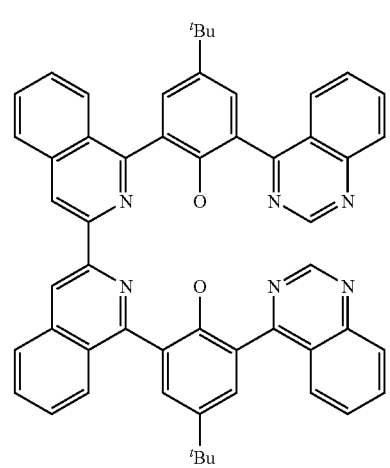

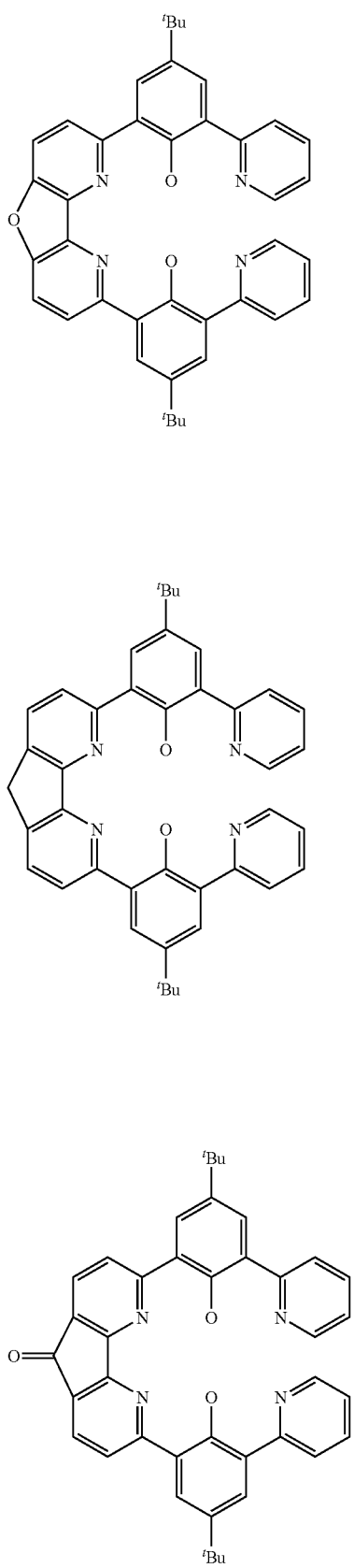

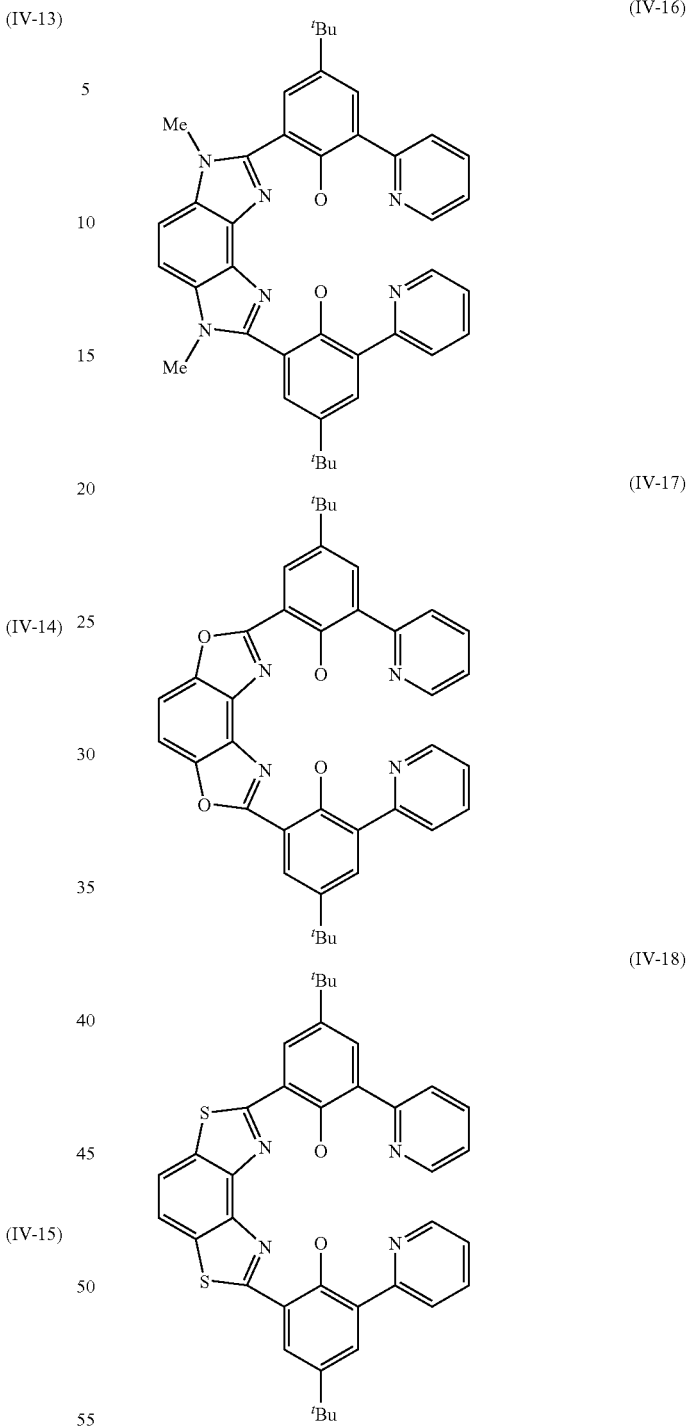

In addition, the metal atom to which the ligand atoms in the metal complex of the present invention are coordination-bonded may be free of charge, or may be a charged ion.

Next, the second embodiment of the present invention will be described.

The inventors of the present invention have made extensive studies with a view to finding a redox catalyst showing particularly high reaction activity. As a result, the inventors have found that a mononuclear complex composed of an aromatic structure shows more excellent stability particularly against heat or an acid than a mononuclear complex composed of an aliphatic structure disclosed heretofore does. The inventors have completed the second embodiment of the present invention on the basis of the finding.

A ligand of a mononuclear complex applied to the second embodiment of the present invention is an organic compound having one nitrogen-containing aromatic heterocycle, one phenol ring, and one or two structures each selected from the group consisting of a phenol ring, a thiophenol ring, and a nitrogen-containing aromatic heterocycle. Specific structures of the organic compound are exemplified in formulae (1a) to (1c). It should be noted that the charges are omitted.

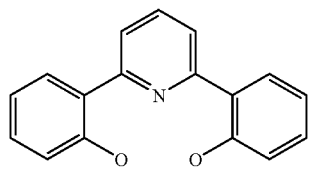
(1a)

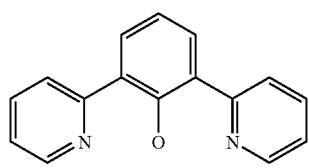
(1b)

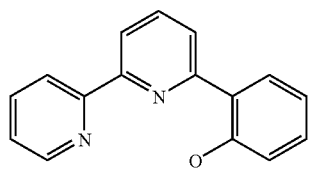
(1c)

The term "nitrogen-containing aromatic heterocycle" as used herein refers to an aromatic group as a compound structure satisfying at least the following condition: the structure has an aromatic heterocyclic structure containing at least one nitrogen atom in its ring. The atoms of which the ring system is constituted may include a heteroatom such as an oxygen atom or a sulfur atom in addition to carbon and nitrogen. Specific examples of the nitrogen-containing aromatic heterocycle include groups having, as a basic structure, pyridine, pyrazine, pyridazine, pyrimidine, pyrrole, triazole, pyrazole, thiazole, oxazole, imidazole, indole, benzoimidazole, phenanthroline, carbazole, quinoline, isoquinoline, cinnoline, phthalazine, quinazoline, quinoxaline, benzodiazine, or the like. It should be noted that phenanthroline has two nitrogen-containing aromatic heterocycles.

Further, the organic compound as a ligand more preferably has two phenol rings. The use of a ligand having such structure improves the stability of the complex.

In addition, the term "phenol ring" refers to an aromatic group as a compound structure satisfying at least the following condition: the structure has a benzene ring structure to which at least one hydroxy group (OH) is bonded. The term "thiophenol ring" refers to an aromatic group as a compound structure satisfying at least the following condition: the structure has a benzene ring structure to which at least one sulfhydryl group (SH) is bonded.

Specific examples of the aromatic groups as a compound structure satisfying at least the condition that the structure has a benzene ring structure include: aromatic hydrocarbons such as benzene, naphthalene, indene, biphenylene, acenaphthylene, fluorene, phenalene, phenanthrene, anthracene, fluoranthene, acephenanthrylene, aceanthrylene, triphenylene, pyrene, chrysene, naphthacene, picene, perylene, pentacene, tetraphenylene, hexacene, and coronene; and groups having, as a basic structure, a fused heterocyclic compound containing an oxygen and sulfur elements, such as benzothiophene, benzofuran, and xanthene. Preferred is a group of an aromatic hydrocarbon and more preferred is a group obtained from benzene, naphthalene, indene, biphenylene, acenaphthylene, fluorene, and phenanthrene.

The ligand used in the second embodiment of the present invention is more preferably an organic compound represented by formula (XI) or (XII).

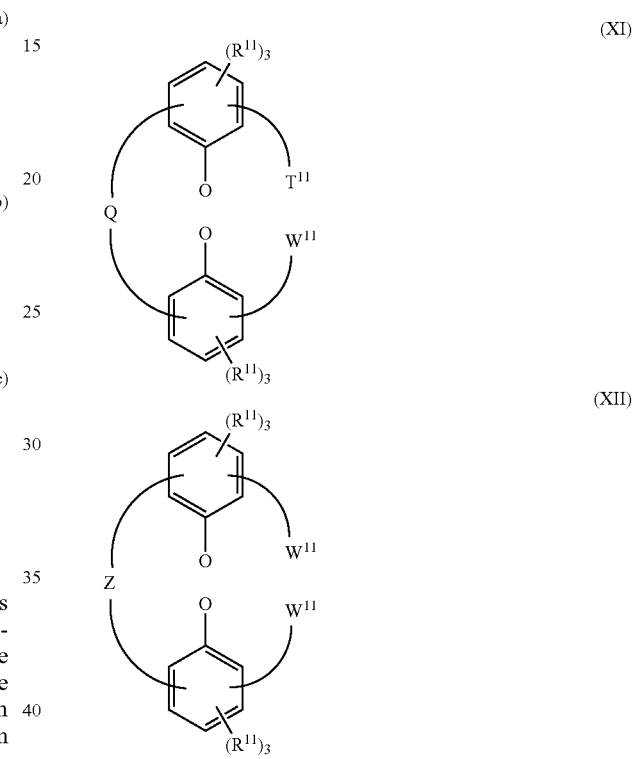

(In formulae (XI) and (XII), $R^{11}$ represents a hydrogen atom or a substituent; two adjacent $R^{11}$'s may be coupled with each other; $R^{11}$'s may be same as or different from each other; Q represents a divalent organic group having at least one nitrogen-containing aromatic heterocycle; Z represents a divalent organic group comprising one or two nitrogen-containing aromatic heterocycles; $T^{11}$ represents a nitrogen-containing aromatic heterocycle; $W^{11}$ represents a nitrogen-free, monovalent aromatic substituent or a hydrogen atom; $W^{11}$'s may be same as or different from each other; and it should be noted that the charges are omitted.)

$R^{11}$ in formula (XI) or (XII) has the same meaning as that of $R^1$ in formula (I), and a preferable range thereof is also the same.

As the monovalent hydrocarbon group represented by $R^{11}$, hydrocarbon groups having 1 to 20 carbon atoms are preferable, hydrocarbon groups having 1 to 12 carbon atoms are more preferable, hydrocarbon groups having 2 to 12 carbon atoms are even more preferable, hydrocarbon groups having 1 to 10 carbon atoms are even more preferable, and hydrocarbon groups having 3 to 10 carbon atoms are even more preferable, and alkyl groups having 3 to 10 carbon atoms are particularly preferable.

Among the above $R^{11}$, a particularly preferable one is a hydrogen atom, a methyl group, an ethyl group, a propyl group, an isopropyl group, a butyl group, an isobutyl group, a tert-butyl group, a phenyl group, a methylphenyl group, a 4-t-butylphenyl group and a naphthyl group.

Q in formula (XI) represents a divalent organic group having one nitrogen-containing aromatic heterocycle. Specific examples thereof include a pyridylene group, a pyrazilene group, a pyrimidylene group, a pyridazilene group, a pyrolylene group, a thiazolylene group, an imidazolylene group, an oxazolylene group, a triazolylene group, an indolylene group, a benzoimidazolylene group, a benzofurylene group, a benzothienylene group, a quinolylene group, an isoquinolylene group, a cinnolilene group, a phthalazilene group, a quinazolilene group, a quinoxalilene group, and a benzodiazilene group. It is preferable a pyridylene group, a pyrazilene group, a pyrimidylene group, a pyridazilene group, or a pyrolylene group; and further preferable a pyridylene group.

Z in formula (XII) is a divalent organic group having one or two nitrogen-containing aromatic heterocycles. Specific examples thereof include, in addition to the organic group described in Q, a 1,10-phenanthroline group, a 2,2'-bipyridylene group, a 2,2'-bipyrrolene group, a 2,2'-bithiazolylene group, a 2,2'-bipyrimidylene group, a 2,2'-bipyridazylene group, and a 2,2'-biimidazolylene group; preferably a 2,2'-bipyridylene group, a 2,2'-bipyrrolene group, a 2,2'-bithiazolylene group, a 2,2'-bipyrimidylene group, a 2,2'-bipyridazylene group, a 2,2'-biimidazolylene group, and a 1,10-phenanthrolylene group; and more preferably a 2,2'-bipyridylene group, a 2,2'-bipyrrolene group, a 2,2'-bithiazolylene group, a 2,2'-biimidazolylene group, and a 1,10-phenanthrolylene group.

In addition, those groups each may have a hydrogen group substituted by a substituent described in $R^1$ above.

In formula (XI), $T^{11}$ represents a nitrogen-containing aromatic heterocycle. Specific examples thereof include pyridine, pyrazine, pyrimidine, pyridazine, pyrrole, thiazole, imidazole, oxazole, triazole, indole, benzoimidazole, quinoline, isoquinoline, cinnoline, phthalazine, quinazoline, quinoxaline and benzodiazine. Among these heterocycles, pyridine, pyrazine, pyrimidine, pyridazine, pyrrole, thiazole, imidazole, oxazole, triazole, indole, and benzoimidazole are preferable; and pyridine, pyrazine, pyrimidine, pyridazine, pyrrole, thiazole, imidazole and oxazole are more preferable. These substituents may be substituted with a substituent represented by the above $R^1$.

$W^{11}$ in formula (XI) or (XII) represents a nitrogen-free, monovalent aromatic substituent or a hydrogen atom. When $W^{11}$'s are present, the $W^{11}$'s may be same as or different from each other. Specific examples thereof include a thienyl group, a benzothienyl group, a dibenzothienyl group, a furyl group, a benzofuryl group, a dibenzofuryl group, a silolyl group, a benzosilolyl group, a dibenzosilolyl group, a hydrogen atom, and substituents in $R^1$ above.

Preferred are a thienyl group, a benzothienyl group, a furyl group, a benzofuryl group, a hydrogen atom, and substituents in $R^{11}$ above.

In addition, these groups each may be further substituted by a hydrocarbon group described in $R^{11}$ above.

The ligand represented by formula (XI) or (XII) is particularly preferably a ligand having a structure represented by formula (XIII).

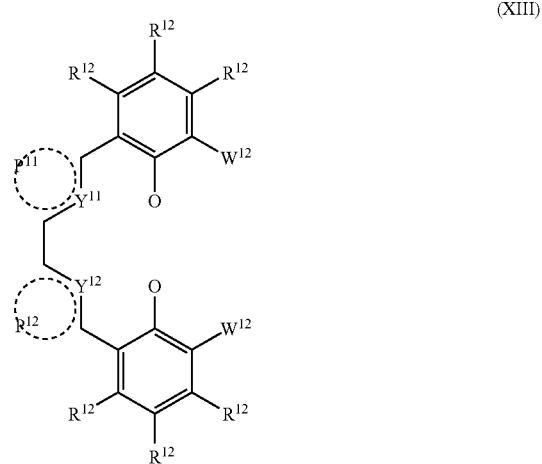

(XIII)

(In formula (XIII), $R^{12}$ has the same meaning as that of $R^{11}$ in formula (XI) or (XII); two $R^{12}$'s bonded to two adjacent atoms may be coupled with each other; and $R^{12}$'s may be same as or different from each other. $Y^{11}$ and $Y^{12}$ each independently represent any one of the following groups.

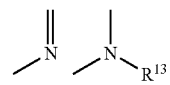

($R^{13}$ represents a hydrogen atom or a hydrocarbon group having 1 to 4 carbon atoms.)

$P^{11}$ represents a group of atoms necessary for forming an aromatic heterocyclic ring together with $Y^{11}$ and the two carbon atoms at a position adjacent to $Y^{11}$; $P^{12}$ represents a group of atoms necessary for forming a heterocyclic ring together with $Y^{12}$ and the two carbon atoms at a position adjacent to $Y^{12}$; and $P^{11}$ and $P^{12}$ may be further bonded to each other to form a ring. $W^{12}$ has the same meaning as that of $W^{11}$ in formula (XI); and it should be noted that the charge is omitted.)

$P^{11}$ and $P^{12}$ may be further bonded to each other to form a ring. Specific examples of the nitrogen-containing aromatic heterocycle include pyridine, pyrazine, pyrimidine, pyrrole, N-alkylpyrrole, thiazole, imidazole, oxazole, isoquinoline, and quinazoline. These may be substituted by $R^1$ above. Preferred are pyridine, pyrazine, pyrimidine, pyrrole, N-alkylpyrrole, thiazole, imidazole, and oxazole; and more preferred are pyridine, pyrazine, pyrimidine, pyrrole, N-alkylpyrrole, and imidazole. Each of these groups may be further substituted with a substituent described in $R^{11}$ above.

As described above, the $P^{11}$ and $P^{12}$ structure may be bonded to each other to form a new ring. For example, the ring preferably has a structure represented by any one of formulae (XIII-1) to (XIII-6), and more preferably has a structure represented by any one of formulae (XIII-1) to (XIII-3).

(XIII-1)

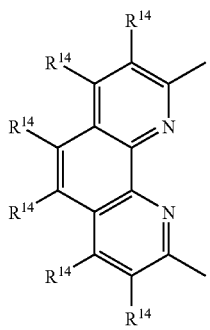

(XIII-2)

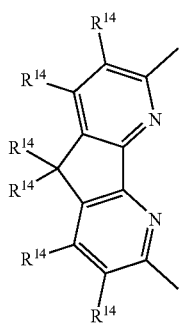

(XIII-3)

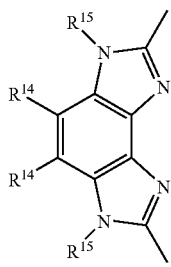

(XIII-4)

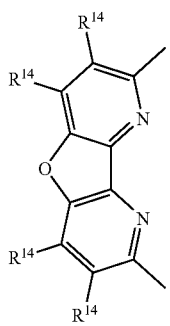

(XIII-5)

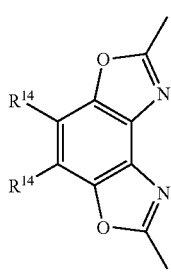

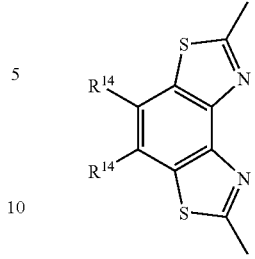

(III-6)

(In formulae (XIII-1) to (XIII-6), $R^{14}$ has the same meaning as that of $R^{11}$ in formula (XI); $R^{14}$'s may be the same or different from each other; $R^{15}$ represents a hydrogen atom or a hydrocarbon group having 1 to 20 carbon atoms; and $R^{15}$'s may be the same or different from each other.)

The ligand in the mononuclear complex preferably has 3 to 15 ligand atoms each of which is capable of bonding to the metal atom by coordination bond. Here, the coordinating atoms are, as described in page 966, Ryogo KUBO et al., Encyclopedia of Physics and Chemistry 4th ed. (issued on Jan. 10, 1991, Iwanami Shoten), atoms having unshared electron pairs to donate electrons to an unoccupied orbital of the metal atoms and bonded with the metal atoms by coordination bond.

The total number of coordinating atoms in the ligand is preferably 3 to 10, more preferably 3 to 8, and particularly preferably 4 to 6. Further, the coordinating atoms may be electrically neutral or charged ions.

The coordinating atom preferably is selected from a nitrogen atom, an oxygen atom and a sulfur atom and coordinating atoms may be the same or different from each other. They are more preferably selected from a nitrogen atom and an oxygen atom.

Here, as the ligand having the structure represented by formula (XIII), ligands represented by the following formulae (XIV-1) to (XIV-7) are given as examples. Among these ligands, ligands represented by the formulae (XIV-1) to (XIV-5) are preferable, and ligands represented by the formulae (XIV-1) to (XIV-4) are particularly preferable. It should be noted that the charges are omitted. (In the following formulae, $^tBu$ represents a tert-butyl group.)

(XIV-1)

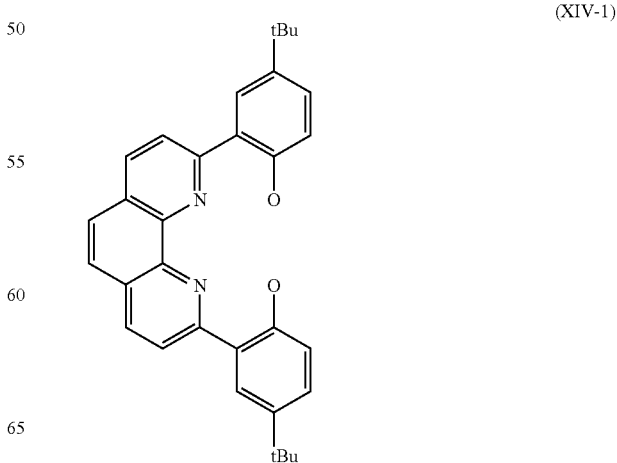

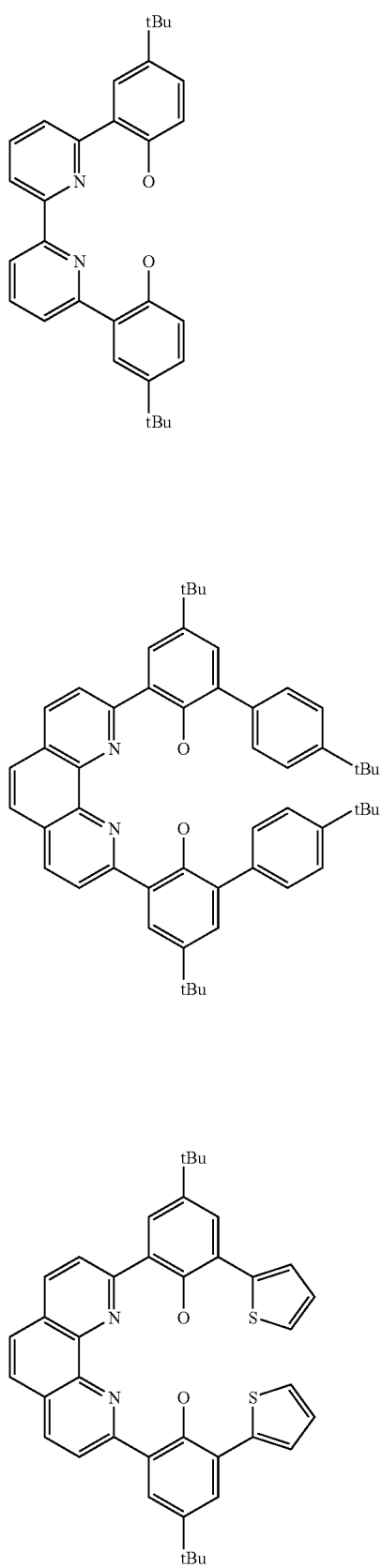
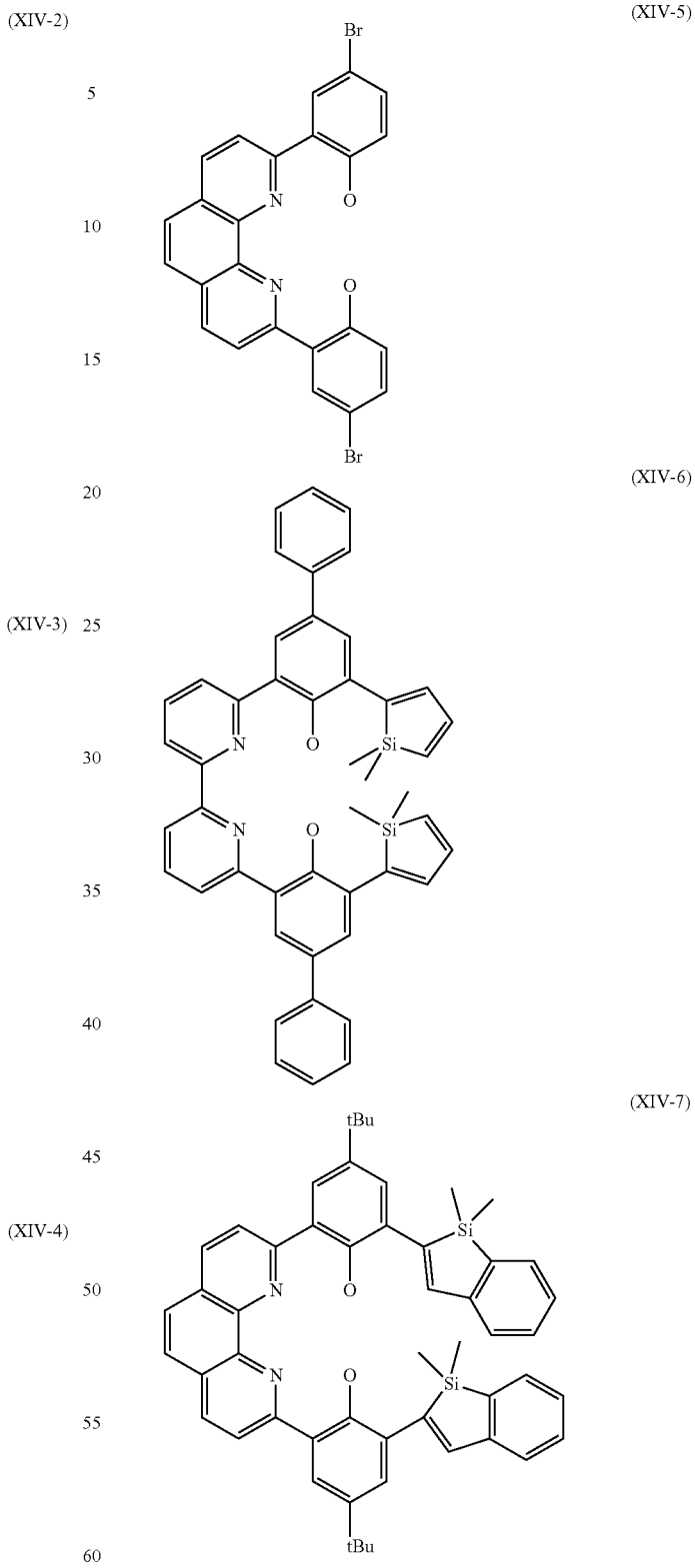
In addition, the metal atom in the mononuclear complex applied to the present invention may be free of charge, or may be a charged ion. The coordination morphology of the metal complex used in the present invention is as follows: the metal complex is preferably a metal complex obtained by causing a transition metal selected from the transition metals belonging to Period 4 and any one of the ligands represented by formulae (XIV-1) to (XIV-7) to react with each other, or more preferably a mononuclear complex obtained by causing a transition metal selected from manganese, iron, cobalt, nickel, and copper and any one of the ligands represented by formulae (XIV-1) to (XIV-4) to react with each other.

In the present invention, the above-mentioned metal atom is preferably a transition metal atom belonging to Period 4 to Period 6 of the periodic table.

In the first embodiment of the present invention, specific examples thereof include metal atoms selected from a group consisting of scandium, titanium, vanadium, chromium, manganese, iron, cobalt, nickel, copper, yttrium, zirconium, niobium, molybdenum, ruthenium, rhodium, palladium, silver, lanthanum, cerium, praseodymium, neodymium, samarium, europium, gadolinium, terbium, dysprosium, holmium, erbium, thulium, ytterbium, lutetium, hafnium, tantalum, tungsten, rhenium, osmium, iridium, platinum and gold.

Among them, preferable examples include metal atoms selected from a group consisting of scandium, titanium, vanadium, chromium, manganese, iron, cobalt, nickel, copper, yttrium, zirconium, niobium, molybdenum, silver, lanthanum, cerium, praseodymium, neodymium, samarium, europium, gadolinium, terbium, dysprosium, holmium, erbium, thulium, ytterbium, lutetium, hafnium, tantalum, and tungsten; and more preferable examples include metal atoms selected from a group consisting of scandium, titanium, vanadium, chromium, manganese, iron, cobalt, nickel, copper, zirconium, niobium, molybdenum, tantalum, and tungsten.

Among these atoms, particularly preferable examples include metal atoms selected from a group consisting of vanadium, chromium, manganese, iron, cobalt, nickel, and copper; and particularly preferable examples include metal atoms selected from a group consisting of manganese, iron, cobalt, nickel, and copper.

In the second embodiment of the present invention, specific examples thereof include metal atoms selected from a group consisting of scandium, titanium, vanadium, chromium, manganese, iron, cobalt, nickel, copper, yttrium, zirconium, niobium, molybdenum, ruthenium, rhodium, palladium, silver, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum and gold.

Among them, preferable examples include metal atoms selected from a group consisting of scandium, titanium, vanadium, chromium, manganese, iron, cobalt, nickel, copper, yttrium, zirconium, niobium, molybdenum, silver, lanthanum, cerium, praseodymium, neodymium, promethium, samarium, europium, gadolinium, terbium, dysprosium, holmium, erbium, thulium, ytterbium, lutetium, hafnium, tantalum, and tungsten; and more preferable examples include metal atoms selected from a group consisting of scandium, titanium, vanadium, chromium, manganese, iron, cobalt, nickel, copper, zirconium, niobium, molybdenum, tantalum, and tungsten.

Among these atoms, particularly preferable examples include metal atoms belonging to Period 4 of the periodic table selected from a group consisting of vanadium, chromium, manganese, iron, cobalt, nickel, and copper; and particularly preferable examples include metal atoms selected from a group consisting of manganese, iron, cobalt, nickel, and copper.

In addition, the metal complex used in the first embodiment of the present invention has preferably 1 to 10, more preferably 1 to 5, still more preferably 1 to 4, or particularly preferably 1 or 2 metal atoms.

The metal complex used in the first embodiment of the present invention must use an organic compound having one nitrogen-containing aromatic heterocycle and four or more structures each selected from the group consisting of a phenol ring, a thiophenol ring, an aniline ring, and a nitrogen-containing aromatic heterocycle in its molecule as a ligand; the metal complex may have any other ligand in addition to the above ligand. The mononuclear complex used in the second embodiment of the present invention may contain other ligands besides the above ligands. As such other ligands, compounds which are ionic or electrically neutral may be used. When these other ligands are contained, these other ligands may be the same or different from each other.

In the first embodiment of the present invention, examples of the electrically neutral compound for the above-described other ligand may include nitrogen atom-containing compounds such as ammonia, pyridine, pyrrole, pyridazine, pyrimidine, pyrazine, 1,2,4-triazine, pyrazole, imidazole, 1,2,3-triazole, oxazole, isoxazole, 1,3,4-oxadiazole, thiazole, isothiazole, indole, indazole, quinoline, isoquinoline, phenantrizine, cinnoline, phthalazine, quinazoline, quinoxaline, 1,8-naphthylidine, acridine, 2,2'-bipyridine, 4,4'-bipyridine, 1,10-phenanthroline, ethylenediamine, propylenediamine, phenylenediamine, cyclohexanediamine, piperazine, 1,4-diazabicyclo [2,2,2]octane, pyridine-N-oxide, 2,2'-bipyridine-N,N'-dioxide, oxamide, dimethyl glyoxime, and o-aminophenol; oxygen-containing compounds such as water, methanol, ethanol, 1-propanol, 2-propanol, n-butyl alcohol, isobutyl alcohol, sec-butyl alcohol, tert-butyl alcohol, 2-methoxyethanol, phenol, oxalic acid, catechol, salicylic acid, phthalic acid, 2,4-pentanedione, 1,1,1-trifluoro-2,4-pentanedione, hexafluoropentanedione, 1,3-diphenyl-1,3-propanedione, and 2,2'-binaphthol; sulfur-containing compounds such as dimethyl sulfoxide and urea; and phosphorus-containing compounds such as 1,2-bis(dimethylphosphino)ethane and 1,2-phenylenebis(dimethylphosphine).

Among them, preferable examples are ammonia, pyridine, pyrrole, pyridazine, pyrimidine, pyrazine, 1,2,4-triazine, pyrazole, imidazole, 1,2,3-triazole, oxazole, isoxazole, 1,3,4-oxadiazole, indole, indazole, quinoline, isoquinoline, phenantrizine, cinnoline, phthalazine, quinazoline, quinoxaline, 1,8-naphthylidine, acridine, 2,2'-bipyridine, 4,4'-bipyridine, 1,10-phenanthroline, ethylenediamine, propylenediamine, phenylenediamine, cyclohexanediamine, piperazine, 1,4-diazabicyclo [2,2,2]octane, pyridine-N-oxide, 2,2'-bipyridine-N,N'-dioxide, oxamide, dimethyl glyoxime, o-aminophenol, water, phenol, oxalic acid, catechol, salicylic acid, phthalic acid, 2,4-pentanedione, 1,1,1-trifluoro-2,4-pentanedione, hexafluoropentanedione, 1,3-diphenyl-1,3-propanedione, and 2,2'-binaphthol; and more preferable examples are ammonia, pyridine, pyrrole, pyridazine, pyrimidine, pyrazine, 1,2,4-triazine, pyrazole, imidazole, 1,2,3-triazole, oxazole, isoxazole, 1,3,4-oxadiazole, indole, indazole, quinoline, isoquinoline, phenantrizine, cinnoline, phthalazine, quinazoline, quinoxaline, 1,8-naphthylidine, acridine, 2,2'-bipyridine, 4,4'-bipyridine, 1,10-phenanthroline, ethylenediamine, propylenediamine, phenylenediamine, cyclohexanediamine, pyridine-N-oxide, 2,2'-bipyridine-N,N'-dioxide, o-aminophenol, phenol, catechol, salicylic acid, phthalic acid, 1,3-diphenyl-1,3-propanedione, and 2,2'-binaphthol.

Among them, particularly more preferable examples are pyridine, pyrrole, pyridazine, pyrimidine, pyrazine, pyrazole, imidazole, oxazole, indole, quinoline, isoquinoline, acridine, 2,2'-bipyridine, 4,4'-bipyridine, 1,10-phenanthroline, phenylenediamine, piperazine, 1,4-diazabicyclo [2,2,2]octane, pyridine-N-oxide, 2,2'-bipyridine-N,N'-dioxide, o-aminophenol, and phenol.

In the second embodiment of the present invention, examples of the electrically neutral compound for the above-described another ligand may include nitrogen atom-containing compounds such as ammonia, pyridine, pyrrole, pyridazine, pyrimidine, pyrazine, 1,2,4-triazine, pyrazole, imidazole, 1,2,3-triazole, oxazole, isoxazole, 1,3,4-oxadiazole, thiazole, isothiazole, indole, indazole, quinoline, isoquinoline, phenantrizine, cinnoline, phthalazine, quinazoline, quinoxaline, 1,8-naphthylidine, acridine, 2,2'-bipyridine, 4,4'-bipyridine, 1,10-phenanthroline, ethylenediamine, propylenediamine, phenylenediamine, cyclohexanediamine, pyridine-N-oxide, 2,2'-bipyridine-N,N'-dioxide, oxamide, dimethyl glyoxime, and o-aminophenol; oxygen-containing compounds such as water, methanol, ethanol, 1-propanol, 2-propanol, n-butyl alcohol, isobutyl alcohol, sec-butyl alcohol, tert-butyl alcohol, 2-methoxyethanol, phenol, oxalic acid, catechol, salicylic acid, phthalic acid, 2,4-pentanedione, 1,1,1-trifluoro-2,4-pentanedione, hexafluoropentanedione, 1,3-diphenyl-1,3-propanedione, and 2,2'-binaphthol; sulfur-containing compounds such as dimethyl sulfoxide and urea; and phosphorus-containing compounds such as 1,2-bis(dimethylphosphino)ethane and 1,2-phenylenebis(dimethylphosphine).

Among them, preferable examples are ammonia, pyridine, pyrrole, pyridazine, pyrimidine, pyrazine, 1,2,4-triazine, pyrazole, imidazole, 1,2,3-triazole, oxazole, isoxazole, 1,3,4-oxadiazole, indole, indazole, quinoline, isoquinoline, phenantrizine, cinnoline, phthalazine, quinazoline, quinoxaline, 1,8-naphthylidine, acridine, 2,2'-bipyridine, 4,4'-bipyridine, 1,10-phenanthroline, ethylenediamine, propylenediamine, phenylenediamine, cyclohexanediamine, pyridine-N-oxide, 2,2'-bipyridine-N,N'-dioxide, oxamide, dimethyl glyoxime, o-aminophenol, water, phenol, oxalic acid, catechol, salicylic acid, phthalic acid, 2,4-pentanedione, 1,1,1-trifluoro-2,4-pentanedione, hexafluoropentanedione, 1,3-diphenyl-1,3-propanedione, and 2,2'-binaphthol; and more preferable examples are ammonia, pyridine, pyrrole, pyridazine, pyrimidine, pyrazine, 1,2,4-triazine, pyrazole, imidazole, 1,2,3-triazole, oxazole, isoxazole, 1,3,4-oxadiazole, indole, indazole, quinoline, isoquinoline, phenantrizine, cinnoline, phthalazine, quinazoline, quinoxaline, 1,8-naphthylidine, acridine, 2,2'-bipyridine, 4,4'-bipyridine, 1,10-phenanthroline, ethylenediamine, propylenediamine, phenylenediamine, cyclohexanediamine, pyridine-N-oxide, 2,2'-bipyridine-N,N'-dioxide, o-aminophenol, phenol, catechol, salicylic acid, phthalic acid, 1,3-diphenyl-1,3-propanedione, and 2,2'-binaphthol.

Further, among the examples, particularly more preferable examples among them are pyridine, pyrrole, pyridazine, pyrimidine, pyrazine, pyrazole, imidazole, oxazole, indole, quinoline, isoquinoline, acridine, 2,2'-bipyridine, 4,4'-bipyridine, 1,10-phenanthroline, phenylenediamine, pyridine-N-oxide, 2,2'-bipyridine-N,N'-dioxide, o-aminophenol, and phenol.

Further, in the first embodiment of the present invention, examples of a ligand having anionic property are a hydroxide ion, a peroxide, a superoxide, a cyanide ion, a thiocyanate ion; halide ions such as a fluoride ion, a chloride ion, a bromide ion and an iodide ion, a sulfate ion, a nitrate ion, a carbonate ion, a perchlorate ion; tetraaryl borate ions such as a tetrafluoroborate ion and a tetraphenyl borate ion, a hexafluorophosphate ion, a methanesulfonate ion, a trifluoromethanesulfonate ion, a p-toluenesulfonate ion, a benzenesulfonate ion, a phosphate ion, a phosphite ion, an acetate ion, a trifluoroacetate ion, a 2-ethyl hexanoate ion, a propionate ion, a benzoate ion, a hydroxide ion, metal oxide ions, a methoxide ion, and an ethoxide ion.

Preferable examples are a hydroxide ion, a chloride ion, a sulfate ion, a nitrate ion, a carbonate ion, a perchlorate ion, a tetrafluoroborate ion, a tetraphenyl borate ion, a hexafluorophosphate ion, a methanesulfonate ion, a trifluoromethanesulfonate ion, a p-toluenesulfonate ion, a benzenesulfonate ion, a phosphate ion, an acetate ion, and a trifluoroacetate ion; and particularly preferable examples among them are a hydroxide ion, a chloride ion, a sulfate ion, a nitrate ion, a carbonate ion, a tetraphenyl borate ion, a trifluoromethanesulfonate ion, a p-toluenesulfonate ion, an acetate ion, a trifluoroacetate ion, and a 2-ethyl hexanoate ion.

Further, in the second embodiment of the present invention, examples of a ligand having anionic property are a hydroxide ion, a peroxide, a superoxide, a cyanide ion, a thiocyanate ion; halide ions such as a fluoride ion, a chloride ion, a bromide ion and an iodide ion, a sulfate ion, a nitrate ion, a carbonate ion, a perchlorate ion, tetraaryl borate ions such as a tetrafluoroborate ion and a tetraphenyl borate ion; a hexafluorophosphate ion, a methanesulfonate ion, a trifluoromethanesulfonate ion, a p-toluenesulfonate ion, a benzenesulfonate ion, a phosphate ion, a phosphite ion, an acetate ion, a trifluoroacetate ion, a propionate ion, a benzoate ion, a hydroxide ion, metal oxide ions, a methoxide ion, and an ethoxide ion and the like.

Among these, preferable examples are a hydroxide ion, a sulfate ion, a nitrate ion, a carbonate ion, a perchlorate ion, a tetrafluoroborate ion, a tetraphenyl borate ion, a hexafluorophosphate ion, a methanesulfonate ion, a trifluoromethanesulfonate ion, a p-toluenesulfonate ion, a benzenesulfonate ion, a phosphate ion, an acetate ion, and a trifluoroacetate ion; and particularly preferable examples among them are a hydroxide ion, a sulfate ion, a nitrate ion, a carbonate ion, a tetraphenyl borate ion, a trifluoromethanesulfonate ion, a p-toluenesulfonate ion, an acetate ion, and a trifluoroacetate ion.

Further, ions exemplified above as a ligand having anionic property may be a counter ion electrically neutralizing the metal complex itself or the mononuclear complex itself of the present invention.

Further, the metal complex or the mononuclear complex used in the present invention may sometimes have a counter ion having cationic property to keep the electric neutrality. Examples of the counter ion having cationic property may be alkali metal ions, alkaline earth metal ions; tetraalkylammonium ions such as a tetra(n-butyl)ammonium ion and a tetraethylammonium ion; and tetraarylphosphonium ions such as a tetraphenylphosphonium ion. Specific examples thereof include a lithium ion, a sodium ion, a potassium ion, a rubidium ion, a cesium ion, a magnesium ion, a calcium ion, a strontium ion, a barium ion, a tetra(n-butyl)ammonium ion, a tetraethylammonium ion, and a tetraphenylphosphonium ion; and more preferable examples include a tetra(n-butyl)ammonium ion, a tetraethylammonium ion, and a tetraphenylphosphonium ion.

Particularly preferable among them are, as a counter ion having cationic property, a tetra(n-butyl)ammonium ion and a tetraethylammonium ion.

Next, the method of synthesizing the metal complex or the mononuclear complex applicable to the present invention will be described. The metal complex and mononuclear complex of the present invention can each be obtained by: synthesizing the ligand organo-chemically; and mixing the ligand and a reactant that provides the metal atom (hereinafter referred to as "metal-providing agent"). As the metal-providing agent, an acetate, hydrochloride salt, sulfate or carbonate of the exemplified metals may be used. Here, the metal-providing agent is a metal salt composed of a combination of the metal atom M and the counter ion X described above. Specific preferable examples of the metal atom M include manganese, iron, cobalt, nickel, and copper. Specific preferable examples of the counter ion X include an acetate ion, a chloride ion, a nitrate ion, and a 2-ethylhexanoate ion. A metal salt composed of a combination of the metal atom M and the counter ion X selected from those preferable examples is preferable.

As described in a non-patent literature "Tetrahedron, 1999, 55, 8377.", the ligand can be synthesized by: performing an addition reaction of an organometallic reactant to a heterocyclic compound; oxidizing the resultant; subjecting the resultant to a halogenation reaction; and subjecting the resultant to a cross-coupling reaction with a transition metal catalyst.

Alternatively, the ligand can be synthesized by performing a multistage cross-coupling reaction using a halogenated aromatic heterocyclic compound (halogenated heterocyclic ring).

As described above, the metal complex of the present invention or the mononuclear complex for use in the present invention can be obtained by mixing the ligand and the metal-providing agent in the presence of a proper reaction solvent. Specific examples of the reaction solvent include water, acetic acid, oxalic acid, ammonia water, methanol, ethanol, n-propanol, isopropyl alcohol, 2-methoxyethanol, 1-butanol, 1,1-dimethylethanol, ethylene glycol, diethyl ether, 1,2-dimethoxyethane, methylethyl ether, 1,4-dioxane, tetrahydrofuran, benzene, toluene, xylene, mesitylene, durene, decalin, dichloromethane, chloroform, carbon tetrachloride, chlorobenzene, 1,2-dichlorobenzene, N,N'-dimethylformamide, N,N'-dimethyl acetamide, N-methyl-2-pyrrolidone, dimethylsulfoxide, acetone, acetonitrile, benzonitrile, triethylamine, and pyridine. A reaction solvent obtained by mixing two kinds of them may be used and a solvent which can dissolve the ligand and the metal-providing agent is preferred. The reaction can be performed at a temperature of generally −10 to 200° C., preferably 0 to 150° C., or particularly preferably 0 to 100° C. for a time period of generally 1 minute to 1 week, preferably 5 minutes to 24 hours, or particularly preferably 1 hour to 12 hours. It should be noted that the reaction temperature and the reaction time can also be appropriately optimized depending on the kinds of the ligand and the metal-providing agent.

An optimum method selected from a known recrystallization method, a known reprecipitation method, and a known chromatography method can be appropriately employed as a method involving isolating and purifying the produced metal complex or mononuclear complex from the reaction solution after the reaction, and two or more of these methods may be employed in combination.

It should be noted that the produced metal complex or mononuclear complex may deposit depending on the reaction solvent; the deposited metal complex or mononuclear complex can be isolated and purified by separating the metal complex by filtration or the like and subjecting the separated product to a washing operation and a drying operation as required.

The coordination morphology of the metal complex used in the first embodiment of the present invention is as follows: the metal complex is preferably a metal complex obtained by causing a transition metal selected from the transition metals belonging to Period 4 and any one of the ligands represented by formulae (IV-1) to (IV-12) to react with each other, or more preferably a metal complex obtained by causing a transition metal selected from manganese, iron, cobalt, nickel, and copper and any one of the ligands represented by the formulae (IV-1) to (IV-7) to react with each other.

A polymer having a residue of the ligand represented by the formula (I) refers to a polymer having a group composed of an atomic group obtained by removing part or all of the hydrogen atoms (one hydrogen atom in ordinary cases) in the ligand represented by formula (I), and the polymer to be used in this case is not particularly limited; examples of the polymer include a conductive polymer, a dendrimer, a natural polymer, a solid polymer electrolyte, polyethylene, polyethylene glycol, and polypropylene. Of those, the conductive polymer or the solid polymer electrolyte is particularly preferred. The term "conductive polymer" is a collective term for polymer substances each showing metallic or semi-metallic conductivity (Iwanami Physical and Chemical Science Dictionary, fifth edition: issued in 1988). Examples of the conductive polymer include: polyacetylene and a derivative of polyacetylene, polyparaphenylene and a derivative of polyparaphenylene, polyparaphenylene vinylene and a derivative of polyparaphenylene vinylene, polyaniline and a derivative of polyaniline, polythiophene and a derivative of polythiophene, polypyrrole and a derivative of polypyrrole, polyfluorene and a derivative of polyfluorene, polyfluorene and a derivative of polyfluorene polycarbazole and a derivative of polycarbazole, and polyindole and a derivative of polyindole described in "Conductive Polymer" (written by Shinichi Yoshimura, KYORITSU SHUPPAN CO., LTD) and "New Applications of Conducting Polymers" (edited by Yukio Kobayashi, CMC Publishing CO., LTD.); and copolymers of the conductive polymers.

Examples of the solid polymer electrolyte include polymers obtained by sulfonating perfluorosulfonic acid, polyether ether ketone, polyimide, polyphenylene, polyarylene, and polyarylene ether sulfone.

A polymer having the residue of the ligand represented by the formula (I) as a repeating unit refers to a polymer having the group composed of an atomic group obtained by removing part or all of the hydrogen atoms (two hydrogen atoms in ordinary cases) in the metal complex represented by the formula (I) as a repeating unit, and the polymer is produced by, for example, polymerizing a bifunctional monomer containing a large cyclic ligand. In addition, a polymer having a group composed of an atomic group obtained by removing part or all of the hydrogen atoms (one hydrogen atom in ordinary cases) in the metal complex having the ligand represented by formula (XI) or (XII) is also permitted. The polymer to be used in this case is not particularly limited; examples of the polymer include a conductive polymer, a dendrimer, a natural polymer, a solid polymer electrolyte, polyethylene, polyethylene glycol, and polypropylene. Of these, the conductive polymer or the solid polymer electrolyte is particularly preferred. The term "conductive polymer" is a collective term for polymer substances each showing metallic or semi-metallic conductivity (Iwanami Physical and Chemical Science Dictionary, fifth edition: issued in 1988). Examples of the conductive polymer include: polyacetylene and a derivative of polyacetylene, polyparaphenylene and a derivative of polyparaphenylene, polyparaphenylene vinylene and a derivative of polyparaphenylene vinylene, polyaniline and a derivative of polyaniline, polythiophene and a derivative of polythiophene, polypyrrole and a derivative of polypyrrole, polyfluorene and a derivative of polyfluorene, polyfluorene and a derivative of polyfluorene, polycarbazole and a derivative of polycarbazole, and polyindole and a derivative of polyindole described in "Conductive Polymer" (written by Shinichi Yoshimura, KYORITSU SHUPPAN CO., LTD) and "New Applications of Conducting Polymers" (edited by Yukio Kobayashi, CMC Publishing CO., LTD.); and copolymers of the conductive polymers.

Examples of the solid polymer electrolyte include polymers obtained by sulfonating perfluorosulfonic, acid, polyether ether ketone, polyimide, polyphenylene, polyarylene, and polyarylene ether sulfone.

In addition, a polymer having a group composed of an atomic group obtained by removing part or all of the hydrogen atoms (two hydrogen atoms in ordinary cases) in the metal complex having the ligand represented by formula (XI) or (XII) is also permitted. For example, examples thereof include those obtained by polymerizing a bifunctional monomer containing a large cyclic ligand.

Next, conditions for stabilization treatment (modification treatment) for the metal complex or mononuclear complex in the present invention are described in detail.

The multinuclear metal complex to be used for the treatment may be one multinuclear metal complex or two or more multinuclear metal complexes.

As pretreatment for the treatment, the metal complex or the mononuclear complex is particularly preferable to be dried at a temperature of 15° C. or higher and 200° C. or lower under reduced pressure of 10 Torr or lower for 6 hours or longer. The pretreatment may be carried out using a vacuum drier or the like.

In the first embodiment of the present invention, the atmosphere for carrying out the treatment of the multinuclear metal complex is preferably in the presence of hydrogen, helium, nitrogen, ammonia, oxygen, neon, argon, krypton, xenon, acetonitrile, or a gas mixture of these gases.

It is preferably in the presence of hydrogen, helium, nitrogen, ammonia, oxygen, neon, argon, or a gas mixture of these gases; and more preferably in the presence of hydrogen, nitrogen, ammonia, argon, or a gas mixture of these gases.

In addition, the pressure in the modification treatment can be appropriately changed depending on the modification treatment to be selected.

The temperature at which the metal complex is subjected to a heating treatment is not particularly limited as long as the following conditions are satisfied: the mass reduction rate after the heating treatment becomes 1 mass % or more and 90 mass % or less, and the carbon content of the modified product after the heating treatment is 5 mass % or more.

The treatment temperature for the heating treatment is preferably 250° C. or higher, more preferably 300° C. or higher, furthermore preferably 400° C. or higher, and even more preferably 500° C. or higher. In addition, an upper limit for the temperature at the time of the burning treatment is not particularly limited as long as the carbon content of the modified product after the treatment is 5 mass % or more; the temperature is preferably 1,200° C. or lower, or more preferably 1,000° C. or lower.

In the first embodiment of the present invention, as to the atmosphere used in the heat-treatment of the multinuclear complex, the multinuclear complex is preferably heat-treated in a reducing atmosphere such as hydrogen or carbon monoxide; an oxidizing atmosphere such as oxygen, carbon dioxide gas or water vapor; an inert gas atmosphere such as nitrogen, helium, neon, argon, krypton or xenon; or an atmosphere in the presence of gas or vapor of a nitrogen-containing compound such as ammonia and acetonitrile or of a mixture of these gases. More preferably the reducing atmosphere is a hydrogen atmosphere or a mixture gas atmosphere containing hydrogen and the above inert gas, the oxidizing atmosphere is an oxygen atmosphere or a mixture gas atmosphere containing oxygen and the above inert gas and the inert gas atmosphere is a nitrogen, neon or argon atmosphere or a mixture gas atmosphere containing these gases.

In addition, the pressure in the heating treatment is not particularly limited; the pressure is preferably around normal pressure, specifically about 0.5 to 1.5 atmospheric pressure.

In the second embodiment of the present invention, as to the atmosphere used in the heat-treatment of the mononuclear complex, the multinuclear complex is preferably heat-treated in a reducing atmosphere containing hydrogen or carbon monoxide, an oxidizing atmosphere containing oxygen, carbon dioxide gas or water vapor, an inert gas atmosphere containing nitrogen, helium, neon, argon, krypton or xenon, or in the presence of gas or vapor of a nitrogen-containing compound such as ammonia and acetonitrile or of a mixture of these gases. More preferably the reducing atmosphere is a hydrogen atmosphere or a mixture gas atmosphere containing hydrogen and the above inert gas, the oxidizing atmosphere is an oxygen atmosphere or a mixture gas atmosphere containing oxygen and the above inert gas and the inert gas atmosphere is a nitrogen, neon or argon atmosphere or a mixture gas atmosphere containing these gases.

Also, the pressure in relation to the heat treatment is, though not particularly limited to, preferably in the vicinity of normal pressure, that is, about 0.5 to 1.5 atmospheric pressure.

In the second embodiment of the present invention, the temperature at which the mononuclear complex is subjected to a heating treatment is not particularly limited as long as the following conditions are satisfied: the mass reduction rate after the treatment becomes 1 mass % or more.

The treatment temperature for the heating treatment is preferably 250° C. or higher, more preferably 300° C. or higher, furthermore preferably 400° C. or higher, and even more preferably 500° C. or higher. In addition, an upper limit for the temperature at the time of the burning treatment is not particularly limited as long as the following conditions are satisfied: the percentage by which the mass of the mononuclear complex reduces after the treatment as compared to that before the treatment becomes 1 mass % or more and 90 mass % or less, and the carbon content of the modified product after the treatment is 5 mass % or more; the temperature is preferably 1,200° C. or lower, or more preferably 1,000° C. or lower.

The treatment time for the heating treatment may be set properly depending on the above-mentioned gas to be used, temperature, and the like and in the state that the above-mentioned gas is tightly closed or ventilated, the temperature is gradually increased from room temperature to an aimed temperature and thereafter, it may be decreased immediately. Particularly, it is preferable to keep the temperature after the temperature reaches the aimed temperature since the metal complex or the mononuclear complex can be gradually heated and the durability can be improved more. The time period for which the temperature is held at the aimed temperature after the arrival is not particularly limited as long as the following conditions are satisfied: the mass reduction rate after the treatment becomes 1 mass % or more and 90 mass % or less, and the carbon content of the modified product after the treatment is 5 mass % or more; the time period is preferably 1 to 100 hours, more preferably 1 to 40 hours, still more preferably 2 hours to 10 hours, or particularly preferably 2 to 5 hours.

In the first embodiment of the present invention, an apparatus for the heating treatment is not either particularly limited and a tubular furnace, an oven, a furnace, an IH hot plate, and the like can be exemplified. The coordination structure of the modified metal complex of the present invention may stabilize in a condensate formed via the following mechanism: the metal complex undergoes a mass reduction involving low-molecular-weight desorption as a result of such heating treatment as described above, and the ligand react with each other to cause the metal complex to form the condensate. A similar effect is obtained in any modification treatment other than the heating treatment as long as the treatment can cause the mass reduction rate to fall within the above range.

In the second embodiment of the present invention, an apparatus for the heating treatment is not either particularly limited and an oven, a furnace, an IH hot plate, and the like can be exemplified. Further, if the amount of the mononuclear complex to be subjected to the heating treatment is about several tens of milligrams, in general, a furnace of a thermal analyzer to be used for thermal analysis can be employed. If a thermogravitational analyzer is used among thermal analyzers, the heating treatment can be stopped while the mass reduction rate is monitored and when a desired mass reduction rate is achieved and thus the heating treatment of the invention can easily be preformed.

Since the modified metal complex of the present invention, in particular, the second embodiment of the present invention has a ligand composed of an aromatic compound, a structure around the metal atom as a result of the heating treatment can be easily retained, so the coordination structure may be stable. With respect to modification treatments for substituting the heating treatment, the same effect can be caused if the treatment can cause the mass reduction rate in the above-mentioned range.

Examples of the modification treatments for substituting the heating treatment may be selected from methods of any radiation irradiation treatment selected from g electromagnetic waves or particle beams such as α-ray, β-ray, neutron beam, electron beam, γ-ray, X-ray, vacuum ultraviolet ray, ultraviolet ray, visible ray, infrared ray, microwave, electric wave, laser and the like; and electric discharge treatment such as corona discharge treatment, glow discharge treatment, plasma treatment (including low temperature plasma treatment).

Preferable modification treatment among them may be the radiating radiation treatment selected from X-ray, electron beam, ultraviolet ray, visible ray, infrared ray, microwave, and laser and low temperature plasma treatment. More preferable treatment may be a method of radiating radiation selected from ultraviolet ray, visible ray, infrared ray, microwave, and laser.

These methods may be carried out according to instruments and treatment methods to be used generally for surface reforming treatment of polymer films and for example, methods disclosed in a literature (Adhesion Society of Japan, "Chemistry of Surface Analysis, Reformation", issued by Nikkan Kogyo Shimbun on Dec. 19, 2003), etc. can be employed.

Herein, at the time of carrying out the above-mentioned radiation irradiation treatment or discharge treatment, the conditions may be arbitrarily set to adjust the mass reduction rate of the metal complex or the mononuclear complex by the treatment in a range of 1 mass % to 90 mass % and the carbon content of the modified product after the treatment of 5 mass % or more and preferable treatment time is within 10 hours, more preferably within 3 hours, furthermore preferably within 1 hour, and particularly preferably within 30 minutes.

As described above, any modification treatment of the heating treatment, radiation irradiation treatment, and discharge treatment is carried out to an extent that the mass reduction rate becomes 1 mass % or more, preferably 2 mass % or more, to obtain the modified metal complex of the invention.

On the other hand, in the case the mass is greatly decreased at the time of heating treatment, radiation irradiation treatment, or discharge treatment, the decomposition of the structure of the complex becomes too significant and therefore, it is not preferable. In the present invention, the upper limit of the mass reduction rate is preferably 80 mass % or less, more preferably 70 mass % or less, and particularly preferably 60 mass % or less.

Further, the modified metal complex of the present invention has a carbon content of 5 mass % or more by elemental analysis. The carbon content is preferably 10 mass % or more, more preferably 20 mass % or more, furthermore preferably 30 mass % or more, and even more preferably 40 mass % or more, and 98 mass % or less. The carbon content of the treated product in the present invention, in particular, the first embodiment of the present invention is preferably as high as possible because the complex structure additionally stabilizes, and the degree of assemblage of the metal atom in the modified metal complex easily increases.

The modified metal complex of the present invention, which can be obtained by any such treatment as described above, contains an unreacted metal complex, or a metal fine particle or metal oxide produced by the decomposition of the metal complex after the treatment in some cases. In such cases, a product obtained by removing the metal fine particle or metal oxide by an acid treatment or the like is the modified metal complex; this can be directly used as a catalyst as long as it can function as a modified metal complex without any trouble.

The term "modified metal complex" as used in the present invention refers to a metal complex or mononuclear complex subjected to a modification treatment selected from a heating treatment, a radiation irradiation treatment, and a discharge treatment until the mass reduction rate after the treatment becomes 1 mass % or more and 90 mass % or less, preferably 80 mass % or less, more preferably 70 mass % or less, and particularly preferably 60 mass % or less, the complex having a carbon content after the modification of 5 mass % or more. The modified metal complex is formed into preferably a carbon compound, or more preferably a graphene compound. It should be noted that the term "carbon compound" refers to a compound having a carbon content of 5 mass % or more. The same catalytic activity as that of the metal complex before the modification treatment can be stabilized, and furthermore, the catalytic activity can be additionally improved.

The mass reduction results mainly from the desorption of a low-molecular-weight substance from the metal complex, and whether such desorption of a low-molecular-weight substance is occurring can be judged by identifying a gas component produced by the modification treatment with a mass spectrometer or the like. In addition, the structure of the metal complex can be identified from a spectrum attributed to a bond between a metal atom and a ligand atom by, for example, an extended X-ray absorption fine structure (EXAFS) analysis method, infrared spectroscopy, or Raman spectroscopy.

As described above, with respect to the modified metal complex of the present invention, it is supposed that ligands are reacted with one another by the modification treatment, that is, ligands are condensed involving low molecule desorption of the ligands and the metal atoms maintain the spatial arrangement in the produced modified ligand approximately the same as that of the metal complex before the modification treatment. Here, the ligand modified product is preferably in such a state that the ligand is condensed and coupled by a graphene-like structure because the modified complex shows additionally high stability against each of an acid and heat. In this connection, "graphene-like structure" means a carbon hexagonal mesh structure of carbon atoms spread two-dimensionally by chemical bonds of $sp^2$ hybrid orbital and some of carbon atoms composing the graphene-like structure may be substituted with heteroatoms such as nitrogen. Further, the above-mentioned graphene-like structure may be layered to form a graphite-like structure.

In addition, when the modified metal complex of the present invention has the graphene-like structure, improving effect on the conductivity of the complex can be obtained. Existence of such graphene-like structure can be confirmed based on the existence of a peak (local maximum) at 1550 to 1600 $cm^{-1}$ in a spectrum obtained by laser Raman spectroanalysis at an excitation wavelength of 532 nm. The lower limit value at which the peak (local maximum) is observed is preferably 1,560 $cm^{-1}$, or more preferably 1,570 $cm^{-1}$. In addition, the upper limit value at which the peak (local maximum) is observed is preferably 1,595 $cm^{-1}$, or more preferably 1,590 $cm^{-1}$.

Next, another embodiment of the modified metal complex of the present invention will be described.

That is, the modified metal complex of the first embodiment of the present invention is a modified metal complex composition showing a ratio of weight loss by the treatment of 5 to 90 mass % and a carbon content after the modification treatment of 5 mass % or more in the case of subjecting a metal complex mixture of (a) a metal complex and (b) a carbon carrier, an organic compound having a boiling point or melting point of 250° C. or more or an organic compound having a thermal polymerization initiating temperature of 250° C. or less to any of heating treatment, radiation irradiation treatment, and discharge treatment. The modified metal complex of the second embodiment of the present invention is a modified metal complex showing a mass reduction rate after the treatment of 1 to 90 mass % and a carbon content after the modification treatment of 5 mass % or more in the case of subjecting a mononuclear metal complex mixture of (a1) a mononuclear complex and (b1) a carbon carrier, an organic compound having a boiling point or melting point of 250° C. or more or an organic compound having a thermal polymerization initiating temperature of 250° C. or less to any of heating treatment, radiation irradiation treatment, and electric discharge treatment. Herein, the mass reduction rate is on the basis of the total of (a) and (b) or (a1) and (b1) in the metal complex mixture.

In the first embodiment of the present invention, in the metal complex mixture, the ratio of (a) and (b) to be mixed is preferably designed such that the content of (a) is 1 to 70 mass % based on the total weight of (a) and (b). The content of the base metal complex is preferably 2 to 60 mass % and particularly preferably 3 to 50 mass %. In the second embodiment of the present invention, in the mononuclear complex mixture, the ratio of (a1) and (b1) to be mixed is preferably designed such that the content of (a1) is 1 to 70 mass % based on the total weight of (a1) and (b1). The content of (a1) is preferably 2 to 60 mass % and particularly preferably 3 to 50 mass %.

Examples of the carbon carrier include carbon particles such as Norit (trade name, manufactured by Norit Corporate Co.), Ketjen black (trade name, manufactured by Lion Corporation), Vulcan (trade name, manufactured by Cabot Corporation), black pearl (trade name, manufactured by Cabot Corporation), acetylene black (trade name, manufactured by Chevron Corporation); fullerene such as C60 and C70; carbon nanotubes, carbon nanohorns, carbon fibers and the like.

Examples of the organic compound having a boiling point or melting point of 250° C. or more are aromatic carboxylic acid derivatives such as perylene-3,4,9,10-tetracarboxylic dianhydride, 3,4,9,10-perylenetetracarboxylic acid diimide, 1,4,5,8-naphthalenetetracarboxylic dianhydride, 1,4,5,8-naphthalenetetracarboxylic acid diimide, 1,4,5,8-naphthalenetetracarboxylic acid, pyromellitic acid, and pyromellitic dianhydride. Herein, the boiling point or melting point can be measured by a conventionally known method and it may be selected from the measured values and also may be selected from the values disclosed in literatures or the like.

It may also be a calculated value obtained by a computation simulation or the like and it may be, for example, selected from the calculated value of the boiling point or melting point registered in SciFinder, which is a computer software program provided by Chemical Abstract Service. In the compounds shown below, the remark "calc" in the boiling point (b.p.) is a calculated value registered in the above-mentioned SciFinder.

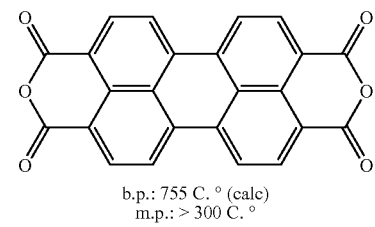

b.p.: 755 C. ° (calc)
m.p.: > 300 C. °

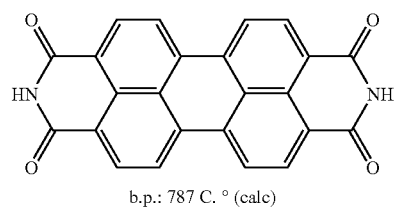

b.p.: 787 C. ° (calc)

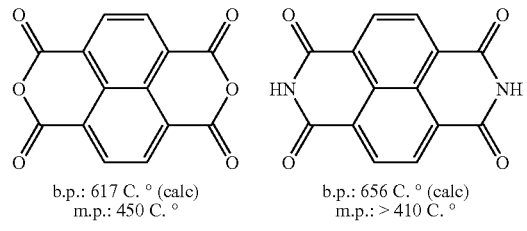

b.p.: 617 C. ° (calc)          b.p.: 656 C. ° (calc)
m.p.: 450 C. °                  m.p.: > 410 C. °

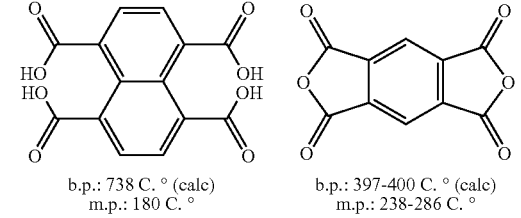

b.p.: 738 C. ° (calc)          b.p.: 397-400 C. ° (calc)
m.p.: 180 C. °                  m.p.: 238-286 C. °

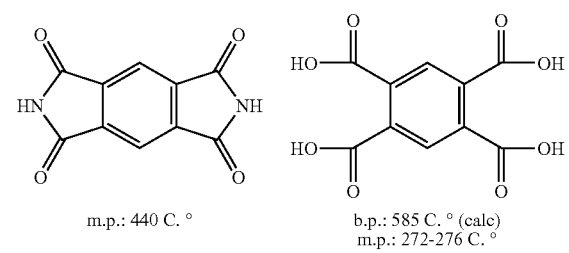

m.p.: 440 C. °                  b.p.: 585 C. ° (calc)
                                m.p.: 272-276 C. °

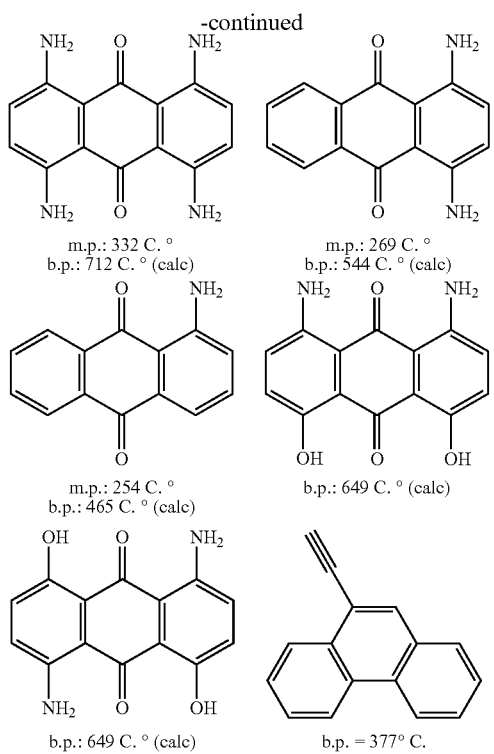

Further, the compound having a thermal polymerization initiation temperature of 250° C. or less is an organic compound having an aromatic ring and further a double bond or a triple bond and examples are organic compounds such as acenaphthylene and vinylnaphthylane. The numeral values attached to the respective compounds shown below are polymerization initiation temperatures of the respective organic compounds. The numeral values are described in "Base of Carbonization Engineering" (1st edition, 2nd printing, Ohmsha, Ltd. 1982).

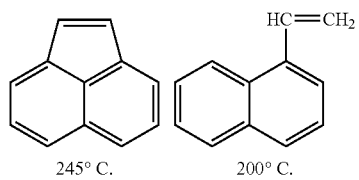

This embodiment is same as the first embodiment in terms of, for example, a modification treatment method, conditions for the treatment, a mass reduction rate as a result of the modification treatment (stabilization treatment), and the carbon content of the metal complex or mononuclear complex after the treatment except that the component (b) as well as the component (a) is used, or the component (b1) as well as the component (a1) is used as described above.

In the present invention, when, in particular, a metal complex using a heteroatom as a ligand atom is subjected to any one of the above treatments, a new bond is formed in addition to a bond between the central metal and the heteroatom, whereby the stability is additionally improved. The term "heteroatom" as used herein refers to an oxygen atom, a nitrogen atom, a sulfur atom, a phosphorus atom, a selenium atom, an arsenic atom, or a halogen atom, more preferably refers to an oxygen atom, a nitrogen atom, a sulfur atom, or a phosphorus atom, still more preferably refers to an oxygen atom, a nitrogen atom, or a sulfur atom, or particularly preferably refers to an oxygen atom or a nitrogen atom.

In addition, the metal atom in the metal complex has the same meaning as that of the above metal atom. The formation of the new bond to the central metal can be confirmed by employing an extended X-ray absorption fine structure (EXAFS) analysis method. The heteroatom coordinated to the central metal is observed as a peak derived from a first adjacent atom in the EXAFS radial distribution function of the central metal, and the peak is generally observed in the range of 1.0 Å or more and 2.5 Å or less. A lower limit value for the range in which the peak derived from the first adjacent atom is observed is preferably 1.1 Å or more, or more preferably 1.2 Å or more. In addition, an upper limit value for the range is preferably 2.2 Å or less, more preferably 1.8 Å or less, or particularly preferably 1.6 Å or less. The formation of the above new bond is observed as another peak at a position more distant from the central metal than the peak derived from the first adjacent atom is. The position of the peak is 0.58 Å or less, more preferably 0.57 Å or less, still more preferably 0.56 Å or less, or particularly preferably 0.55 Å or less from the peak derived from the first adjacent atom.

The number of the other peaks is not particularly limited as long as the number is one or more; the number is preferably one (1) to three (3), more preferably one (1) or two (2), or particularly preferably one (1). In addition, the intensity of each of the other peaks is preferably ⅖ or more, more preferably ½ or more, particularly preferably ⅔ or more, or most preferably ¾ or more of the intensity of the peak derived from the first adjacent atom.

The modified metal complex of the present invention, in particular, the first embodiment of the present invention can be used in combination with, for example, any one of the various carriers and additives, or its shape can be processed depending on various applications. Since the treated metal complex of the present invention has a stabilized complex structure and a high degree of assemblage of its metal atom, the complex can particularly suitably find use in applications including: decomposition catalysts for hydrogen peroxide; electrode materials for batteries; memory materials for electronic devices; membrane degradation inhibitors for fuel cells; oxidative coupling catalysts for aromatic compounds; catalysts for cleaning an exhaust gas and waste water; redox catalyst layers for dye-sensitized solar cells; carbon dioxide reduction catalysts; catalysts for the production of reformed hydrogen; and oxygen sensors.

The modified metal complex of the present invention, in particular, the second embodiment of the present invention can be used in combination with, for example, any one of the various carriers and additives, or its shape can be processed depending on various applications. The complex can find use in applications including: electrode catalysts and membrane degradation inhibitors for fuel cells; oxidative coupling catalysts for aromatic compounds; catalysts for cleaning an exhaust gas and waste water; redox catalyst layers for dye-sensitized solar cells; carbon dioxide reduction catalysts; catalysts for the production of reformed hydrogen; and oxygen sensors.

In addition, when the modified metal complex of the present invention is used as a catalyst, the complex can be used as a composition containing a carbon carrier and/or a conductive polymer. Such procedure is useful from, for example, the following viewpoints: additional improvements in stability and catalytic activity of the modified metal complex. Examples of the conductive polymer are polyacetylene, polyaniline, polypyrrole and the like. In addition, specific examples of the carbon carrier are same as those described above. In addition, as such composition, there can be used a mixture of the modified metal complexes of the present invention, carbon carriers or conductive polymers, or a combination of a carbon carrier and a conductive polymer.

Hereinafter, preferred applications of the modified metal complex of the present invention are described.

The modified metal complex of the present invention, in particular, the first embodiment of the present invention is preferably formed into a carbon compound, or more preferably a graphene compound. The same catalytic activity as that of the metal complex before the modification treatment can be stabilized, and furthermore, the catalytic activity can be additionally improved. Specifically, the complex is preferably used as a decomposition catalyst for a peroxide, in particular, a decomposition catalyst for hydrogen peroxide. When the complex is used as a decomposition catalyst for hydrogen peroxide, the complex shows the following characteristic: the complex can decompose hydrogen peroxide into water and oxygen while suppressing the production of a hydroxyl radical. Specifically, the complex can find use in applications including: degradation inhibitors for ionic conduction membranes to be used in solid polymer electrolyte type fuel cells or in the electrolysis of water; and antioxidants for medicine, agricultural chemicals, and food.

The modified metal complex of the present invention, in particular, the second embodiment of the present invention is preferably used in a solid polymer type fuel cell; in this application, the modified metal complex can be used after having been introduced into, for example, any one of an electrolyte, an electrode, and an interface between the electrolyte and the electrode. The solid polymer type fuel cell is generally constituted by laminating, through a separator, electrolyte membrane-electrode conjugates each composed of a fuel electrode into which a fuel containing hydrogen, methanol, or the like is introduced, an oxygen electrode supplied with an oxidant gas containing oxygen, and an electrolyte membrane interposed between the fuel electrode and the oxygen electrode. The complex is preferably introduced into a site selected from the oxygen electrode, the fuel electrode, and an interface between the electrolyte and each electrode. Any one of the various methods can be employed as a method of introducing the catalyst into, for example, the electrolyte, each electrode, or an interface between the electrolyte and the electrode. Examples of the method include: a method involving dispersing the modified metal complex in an electrolyte solution such as a fluorine-based ion exchange resin (such as a Nafion (registered trademark, Du Pont)), molding the prepared dispersion liquid into a membrane, and using the membrane as the electrolyte membrane or a method involving applying the dispersion liquid to the electrolyte membrane, drying the applied liquid, and using the resultant as an electrode; and a method involving applying a solution in which the modified product is dispersed to each electrode, drying the applied solution, and joining the electrolyte membrane to the resultant to introduce a peroxide decomposition catalyst layer into an interface between the electrolyte and the electrode.

In addition, the modified metal complex of the present invention is suitable also as an oxidative coupling catalyst for an aromatic compound; in this application, the complex can be used as a catalyst involved in the production of a polymer such as polyphenylene ether or polycarbonate. The modified product is used in, for example, such form as described below: the modified product is directly added to a reaction solution, or zeolite, silica, or the like is caused to carry the modified product.

The modified metal complex of the present invention can be used also as a desulfurization/denitration catalyst for transforming a sulfur oxide/nitrogen oxide in an exhaust gas from any one of the various factories and automobiles into sulfuric acid/ammonia and the like. The complex is used, for example, as follows: a tower through which an exhaust gas from a factory passes is filled with the complex, or a muffler of an automobile is filled with the complex.

Further, the modified metal complex of the present invention can be used also as a catalyst for reforming CO in reformed hydrogen. The reformed hydrogen contains CO and the like, so the following problem arises when the reformed hydrogen is used in a fuel cell: a fuel electrode is poisoned with CO. Accordingly, an utmost reduction of a CO concentration is desired. Specifically, the complex is used in accordance with, for example, the method described in Chemical Communication, 3385 (2005).

The modified metal complex of the present invention, in particular, the first embodiment of the present invention is a modified metal complex excellent in stability (such as acid resistance or thermal stability), and generally shows excellent catalytic activity. The modified metal complex of the present invention, in particular, the first embodiment of the present invention is a complex compound showing excellent metal retentivity in a solution. In addition, the metal atoms are assembled by any of a nitrogen-containing aromatic heterocycle, a phenol ring, a thiophenol ring, and an aniline ring, so a reaction space suitable for a catalytic reaction is provided. Moreover, a new bond is formed between the assembled metal complexes by a modification treatment, whereby the complex is expected to serve as a catalyst which not only shows improved stability but also is excellent in reaction selectivity.

According to the present invention, in particular, the first embodiment of the present invention, there can be provided a catalyst showing high reaction activity even in the presence of an acid or even under heating as a catalyst in a redox reaction involving electron transfer such as a peroxide decomposition reaction, an oxide decomposition reaction, an oxygenation reaction, an oxidative coupling reaction, a dehydrogenation reaction, a hydrogenation reaction, or an electrode reaction. The catalyst is extremely useful in industry because the catalyst can be suitably used in the synthesis of an organic compound or a polymer compound, or can be suitably used as an additive, a modifier, or a sensor material.

In the present invention, a modified metal complex showing high reaction activity and excellent in thermal stability can be provided as a redox catalyst by subjecting a metal complex or mononuclear complex to a modification treatment.

EXAMPLES

The present invention will be described in more detail based on examples given below, but the invention is not meant to be limited by these.

Synthesis Example 1

Metal Complex (A) was synthesized in accordance with the following reaction formula.

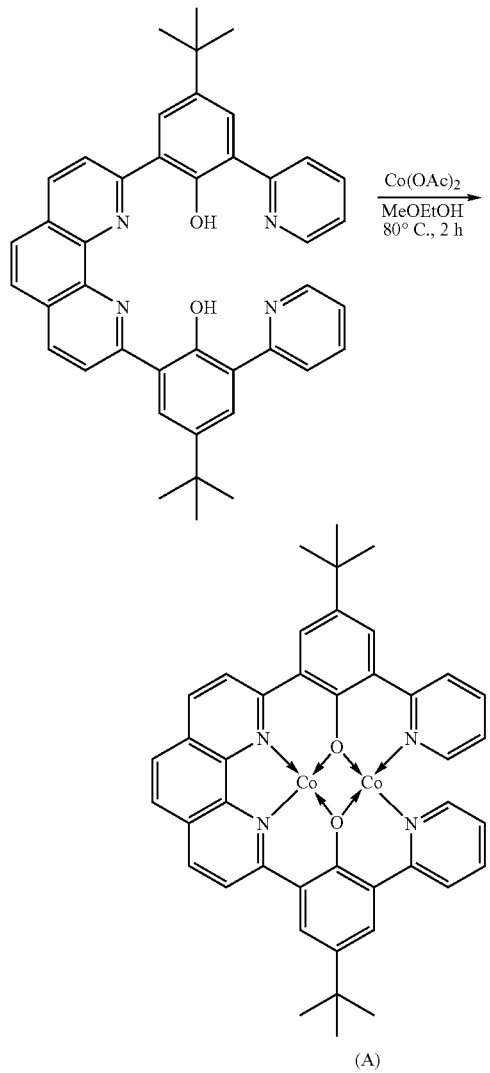

(A)

The above ligand as a raw material for the complex was synthesized on the basis of Tetrahedron, 55, 8377 (1999). Under a nitrogen atmosphere, 1.388 g of the ligand and solution of 1.245 g of cobalt acetate tetrahydrate in 200 mL of 2-methoxyethanol were loaded into a 500-mL egg plant flask, and the mixture was stirred for 2 hours while being heated at 80° C., whereby a brown solid was produced. The solid was taken by filtration, and was then washed with 20 mL of 2-methoxyethanol and dried, whereby Metal Complex (A) was obtained (yield 1.532 g, 74%).

Elementary Analysis Value (%):

Calculated Value (Calcd for $C_{49}H_{50}Co_2N_4O_8$); C, 62.56; H, 5.36; N, 5.96; Co, 12.53

Actual Measurement Value: C, 62.12; H, 5.07; N, 6.03; Co, 12.74

The Metal Complex (A) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (A).

Synthesis Example 2

Metal Complex (B) was synthesized in accordance with the following reaction formula.

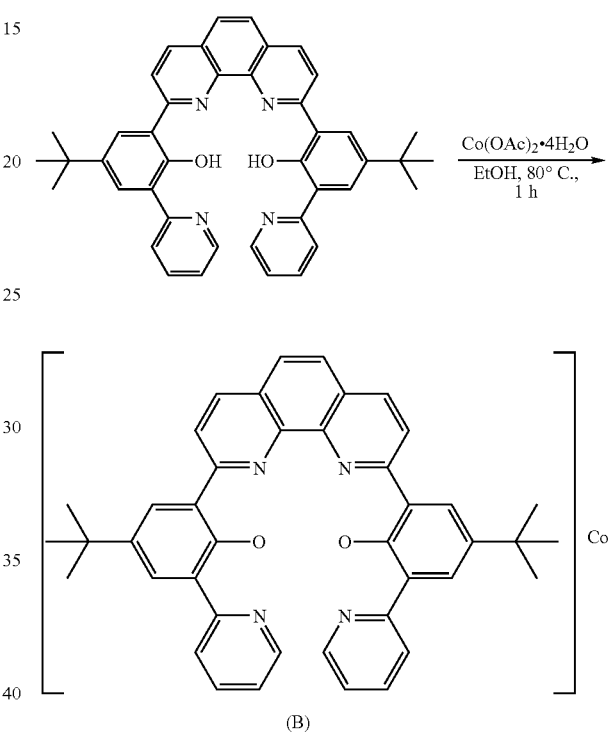

(B)

As the above ligand as a raw material for the complex, the ligand synthesized in Example 1 was used. 0.315 g of the ligand and 50 mL of ethanol solution containing 0.124 g of cobalt acetate tetrahydrate were loaded into a 100-mL egg plant flask, and the mixture was stirred for 1 hour while being heated at 80° C. The produced brown precipitate was taken by filtration, washed with ethanol, and dried in a vacuum, whereby Metal Complex (B) was obtained (yield: 0.270 g, 81%).

Elementary Analysis Value (%):

Calculated Value (Calcd for $C_{42}H_{40}CoN_4O_4$); C, 69.70; H, 5.57; N, 7.74

Actual Measurement Value: C, 70.01; H, 5.80; N, 7.56

The Metal Complex (B) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (B).

Synthesis Example 3

Metal Complex (C) shown in the following reaction formula was synthesized in accordance with the method described in Australian Journal of Chemistry, 23, 2225 (1970).

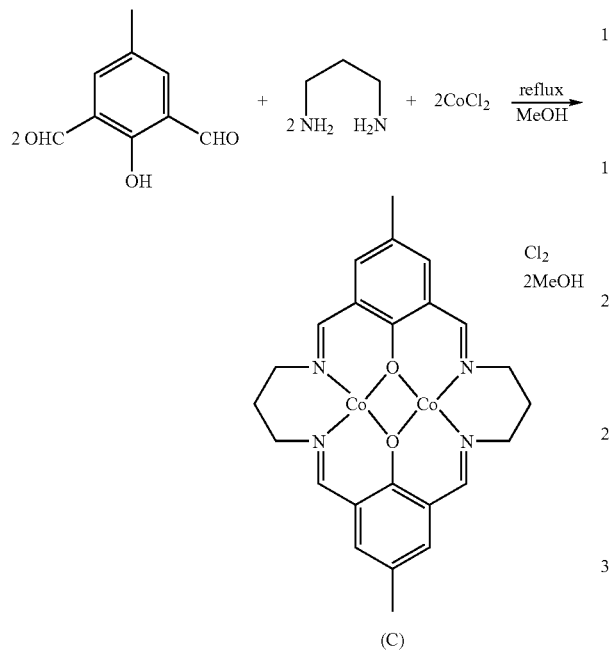

(C)

Under a nitrogen atmosphere, solution of 1.9 g of cobalt chloride hexahydrate and 1.31 g of 4-methyl-2,6-diformylphenol in 50 mL of methanol was charged into a 100-mL egg plant flask, and the solution was stirred at room temperature. Twenty (20) mL of methanol containing 0.59 g of 1,3-propanediamine was gradually added to the solution. The above mixture was refluxed for 3 hours, whereby a brownish-red precipitate was produced. The precipitate was taken by filtration, and was then dried, whereby Metal Complex (C) was obtained (yield: 1.75 g, 74%). In the above reaction formula, "$Cl_2$" shows that two equivalents of a chloride ion exists as a counter ion, and "2MeOH" shows that two equivalents of a methanol molecule is contained.

Elementary Analysis Value (%):

Calculated Value (Calcd for $C_{26}H_{34}Cl_2Co_2N_4O_4$); C, 47.65; H, 5.23; N, 8.55

Actual Measurement Value: C, 46.64; H, 5.02; N, 8.58

The Metal Complex (C) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (C).

Synthesis Example 4

Metal Complex (D) was synthesized in accordance with the following reaction formula.

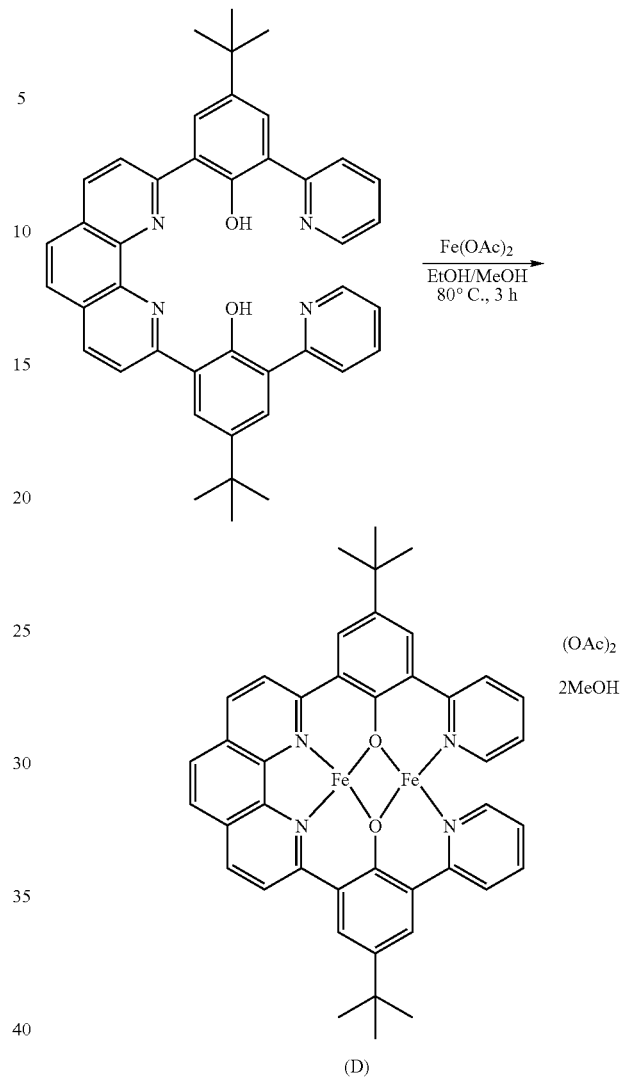

(D)

As the above ligand as a raw material for the complex, the ligand synthesized in Synthesis Example 1 was used. Under a nitrogen atmosphere, 10 mL of ethanol solution containing 0.126 g of the ligand and 5 mL of methanol solution containing 0.078 g of ferrous acetate were loaded into a 50-mL egg plant flask, and the mixture was stirred for 3 hours while being heated at 80° C., whereby a brown solid was precipitated. The solid was taken by filtration, and was then washed with methanol and dried, whereby Metal Complex (D) was obtained (yield: 0.075 g, 41%). In the above reaction formula, "$(OAc)_2$" shows that two equivalents of an acetic acid ion exists as a counter ion, and "MeOH" shows that two equivalents of a methanol molecule is contained.

Elementary Analysis Value (%):

Calculated Value (Calcd for $C_{48}H_{50}Fe_2N_4O_8$): C, 62.49; H, 5.46; N, 6.07

Actual Measurement Value: C, 59.93; H, 5.29; N, 5.70

The Metal Complex (D) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (D).

Synthesis Example 5

Metal Complex (E) was synthesized in accordance with the following reaction formula.

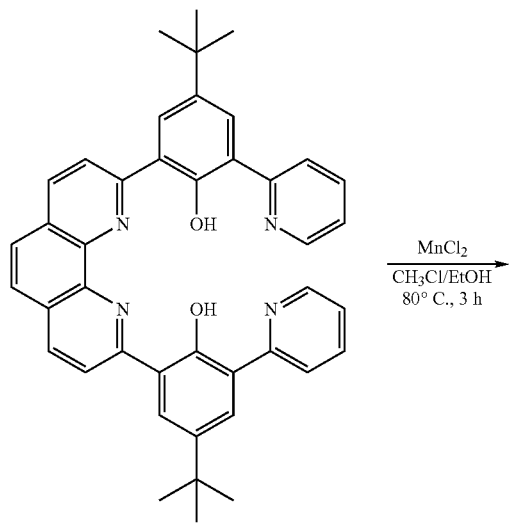

As the above ligand as a raw material for the complex, the ligand synthesized in Synthesis Example 1 was used. Under a nitrogen atmosphere, 2 mL of chloroform solution containing 0.126 g of the ligand and 6 mL of ethanol solution containing 0.089 g of manganese chloride tetrahydrate were loaded into a 25-mL egg plant flask, and the mixture was stirred for 3 hours while being heated at 80° C., whereby a yellow solid was precipitated. The solid was taken by filtration, and was then washed with chloroform and ethanol, and dried, whereby Metal Complex (E) was obtained (yield 0.092 g). In the above reaction formula, "$Cl_2$" shows that two equivalents of a chloride ion exists as a counter ion, and "$2H_2O$" shows that two equivalents of a water molecule is contained.

Elementary Analysis Value (%):

Calculated Value (Calcd for $C_{42}H_{40}Mn_2N_4O_4$); C, 59.66; H, 4.77; N, 6.63

Actual Measurement Value: C, 58.26; H, 4.58; N, 6.33

The Metal Complex (E) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (E).

Synthesis Example 6

Metal Complex (F) was synthesized by mixing a ligand and chloroform solution containing cobalt 2-ethylhexanoate and by causing them to react with each other in accordance with the following reaction formula. The following ligand as a raw material for the complex was synthesized on the basis of Tetrahedron, 1999, 55, 8377.

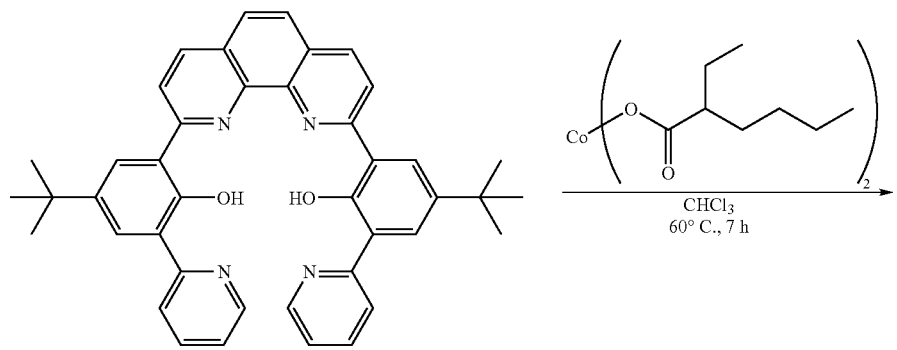

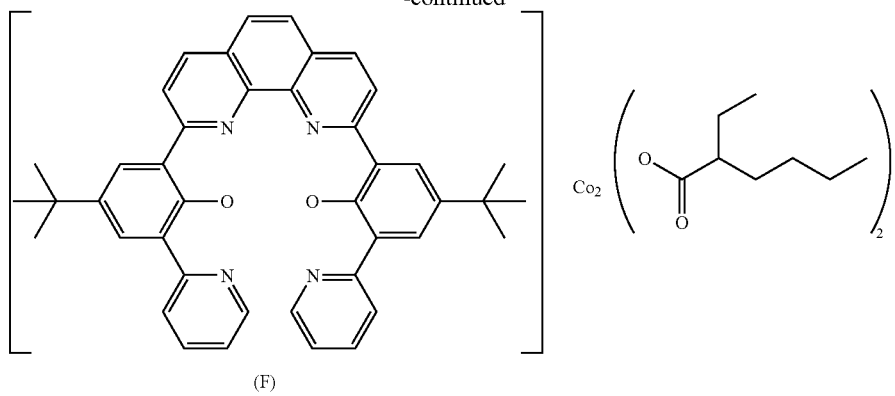

(F)

Under a nitrogen atmosphere, 0.077 g of the ligand and 5 mL of chloroform solution containing 0.239 g of cobalt 2-ethylhexanoate (65 wt % mineral oil solution) were loaded into a 25-mL egg plant flask, and the mixture was stirred for 9 hours while being heated at 60° C. The solution was dropped to an Erlenmeyer flask containing 50 mL of diethyl ether. The precipitated solid was taken by filtration, washed with diethyl ether, and dried, whereby Metal Complex (F) was obtained (yield 0.146 g).

ESI-MS [M+•]: 1032.2

Elementary Analysis Value (%):

Calculated Value (Calcd for $C_{58}H_{66}Co_2N_4O_6$); C, 67.43; H, 6.44; N, 5.42

Actual Measurement Value: C, 66.97; H, 6.21; N, 5.27

The Metal Complex (F) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (F).

Synthesis Example 7

Metal Complex (G) was synthesized by mixing a ligand and ethanol solution containing nickel acetate tetrahydrate and by causing them to react with each other in accordance with the following reaction formula. The following ligand as a raw material for the complex was synthesized on the basis of Tetrahedron, 1999, 55, 8377.

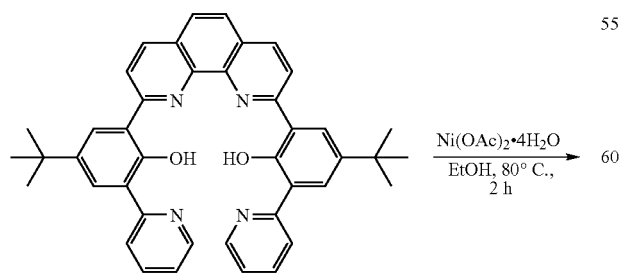

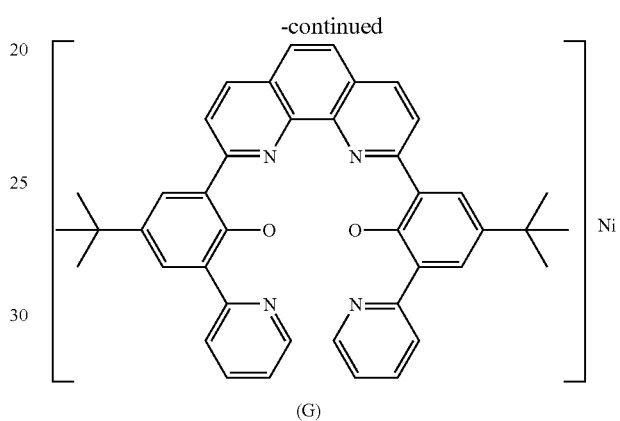

(G)

Under a nitrogen atmosphere, 0.250 g of the ligand and 30 mL of ethanol solution containing 0.100 g of nickel acetate tetrahydrate were loaded into a 50-mL egg plant flask, and the mixture was stirred for 2 hours while being heated at 80° C. The produced orange precipitate was taken by filtration, washed with ethanol, and dried in a vacuum, whereby Metal Complex (G) was obtained (yield 0.242 g).

Elementary Analysis Value (%):

Calcd for $C_{42}H_{36}N_4NiO_2$; C, 73.38; H, 5.28; N, 8.15

Found: C, 72.42; H, 5.27; N, 7.96

ESI-MS [M+•]: 687.1

The Metal Complex (G) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (G).

Synthesis Example 8

Metal Complex (H) was synthesized by mixing a ligand and ethanol solution containing cupric acetate monohydrate and by causing them to react with each other in accordance with the following reaction formula. The following ligand as a raw material for the complex was synthesized on the basis of Tetrahedron, 1999, 55, 8377.

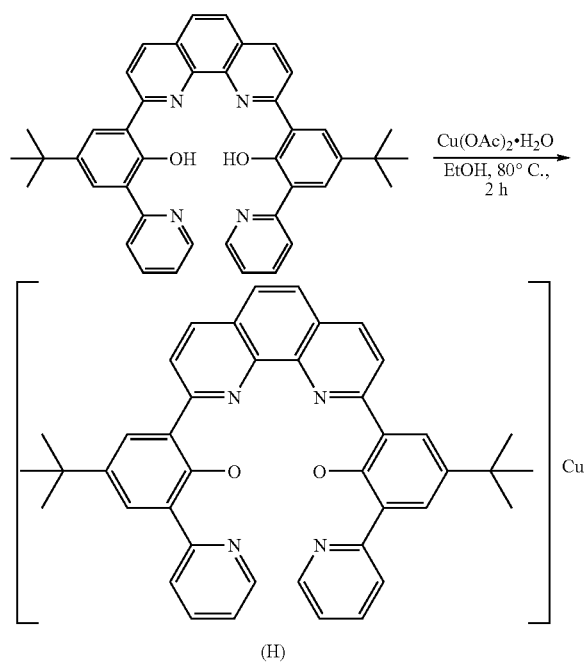

(H)

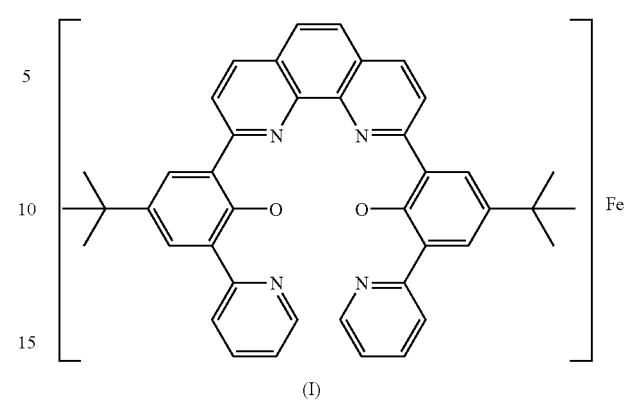

(I)

Under a nitrogen atmosphere, 0.315 g of the ligand and 30 mL of ethanol solution containing 0.100 g of cupric acetate monohydrate were loaded into a 50-mL egg plant flask, and the mixture was stirred for 2 hours while being heated at 80° C. The produced ocher precipitate was taken by filtration, washed with ethanol, and dried in a vacuum, whereby Metal Complex (H) was obtained (yield 0.250 g).

Elementary Analysis Value (%):
Calcd for $C_{42}H_{36}CuN_4O_2$; C, 72.87; H, 5.24; N, 8.09
Found: C, 72.22; H, 5.37; N, 7.77
ESI-MS [M+•]: 692.1.

The Metal Complex (H) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (H).

Synthesis Example 9

Metal Complex (I) was synthesized by mixing a ligand and ethanol solution containing ferrous acetate and by causing them to react with each other in accordance with the following reaction formula. The following ligand as a raw material for the complex was synthesized on the basis of Tetrahedron, 1999, 55, 8377.

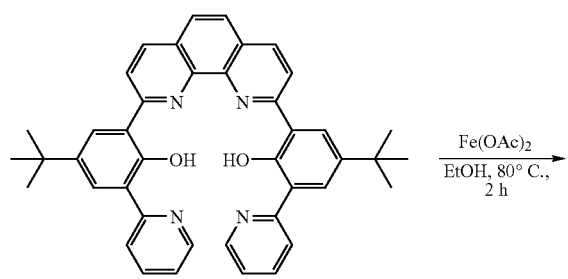

Under a nitrogen atmosphere, 0.440 g of the ligand and 30 mL of ethanol solution containing 0.120 g of ferrous acetate were loaded into a 50-mL egg plant flask, and the mixture was stirred for 2 hours while being heated at 80° C. The produced orange precipitate was taken by filtration, washed with ethanol, and dried in a vacuum, whereby Metal Complex (I) was obtained (yield 0.380 g).

Elementary Analysis Value (%):
Calcd for $C_{42}H_{36}FeN_4O_2$; C, 73.68; H, 5.30; N, 8.18
Found: C, 72.20; H, 5.42; N, 7.85
ESI-MS [M+•]: 684.0

The Metal Complex (I) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (I).

Synthesis Example 10

Metal Complex (J) was synthesized by mixing a ligand and ethanol solution containing nickel acetate and by causing them to react with each other in accordance with the following reaction formula. The following ligand as a raw material for the complex was synthesized on the basis of Tetrahedron, 1999, 55, 8377.

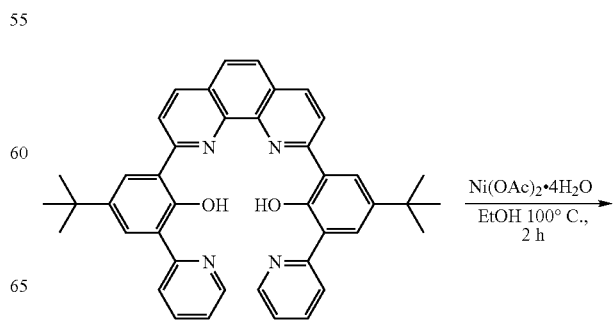

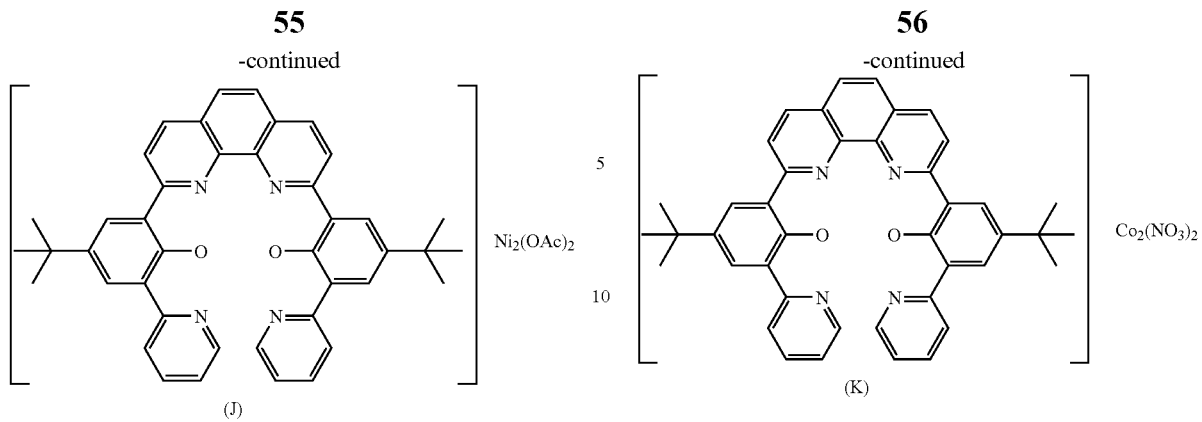

Under a nitrogen atmosphere, 0.200 g of the ligand and 30 mL of ethanol solution containing 0.250 g of nickel acetate tetrahydrate were loaded into a 50-mL egg plant flask, and the mixture was stirred for 2 hours while being heated at 100° C., whereby an orange solid was precipitated. The solid was taken by filtration, washed with ethanol and diethyl ether, and dried, whereby Metal Complex (J) was obtained (yield 0.276 g).

Elementary Analysis Value (%):

Calculated Value (Calcd for $C_{46}H_{42}N_4Ni_2O_6$): C, 63.93; H, 4.90; N, 6.07

Actual Measurement Value: C, 63.22; H, 5.02; N, 6.43

The Metal Complex (J) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (J).

Synthesis Example 11

Metal Complex (K) was synthesized by mixing chloroform solution containing a ligand and methanol solution containing cobalt nitrate hexahydrate and by causing them to react with each other in accordance with the following reaction formula. The following ligand as a raw material for the complex was synthesized on the basis of Tetrahedron, 1999, 55, 8377.

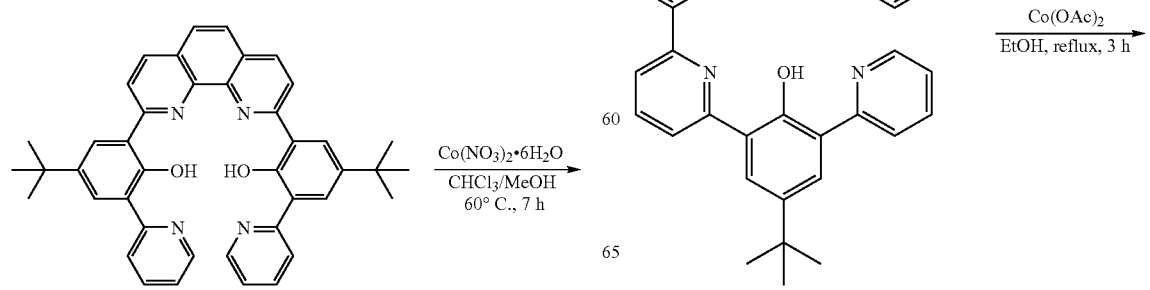

Under a nitrogen atmosphere, 2 mL of chloroform solution containing 0.096 g of the ligand and 5 mL of methanol solution containing 0.082 g of cobalt nitrate hexahydrate were loaded into a 100-mL egg plant flask, and the mixture was stirred for 7 hours while being heated at 60° C., whereby a yellow solid was produced. The solid was taken by filtration, and was then washed with methanol and dried, whereby Metal Complex (K) was obtained (yield 0.036 g).

ESI-MS $[M–NO_3]^+$: 808.0

The Metal Complex (K) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (K).

Synthesis Example 12

Metal Complex (L) was synthesized by mixing a ligand and ethanol solution containing cobalt acetate tetrahydrate and by causing them to react with each other in accordance with the following reaction formula. The following ligand as a raw material for the complex was synthesized on the basis of Tetrahedron, 1999, 55, 8377.

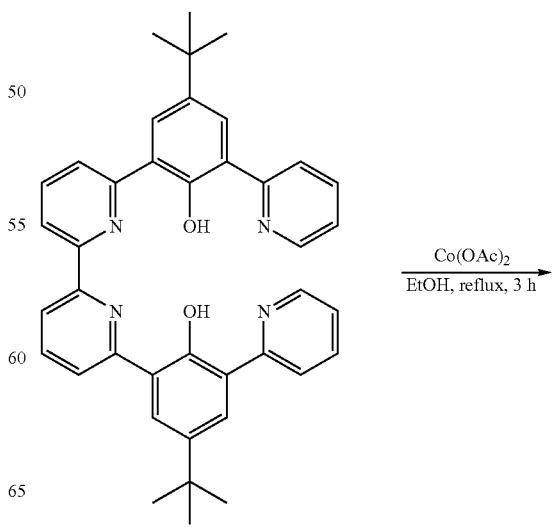

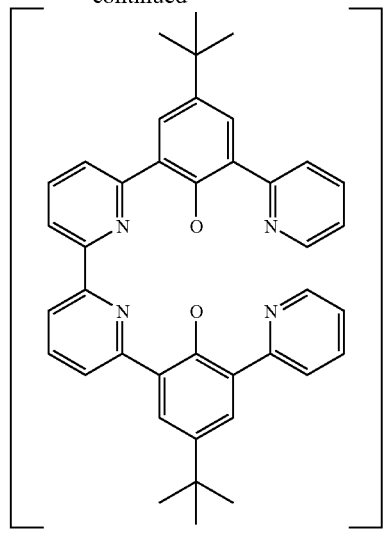

(L)

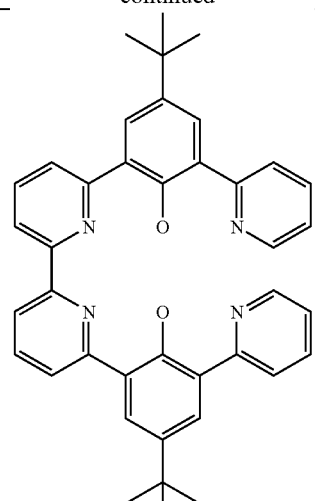

(M)

Under a nitrogen atmosphere, 0.303 g of the ligand and solution of 0.125 g of cobalt acetate tetrahydrate were loaded into a 100-mL two-necked flask, and 50 mL of ethanol was added thereto. The solution was refluxed for 3 hours, whereby an ocher solid was produced. The precipitate was taken by filtration and dried, whereby Metal Complex (L) was obtained (yield 0.242 g).

ESI-MS [M+H]$^+$: 664.2

The Metal Complex (L) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (L).

Synthesis Example 13

Metal Complex (M) was synthesized by mixing a ligand and ethanol solution containing cobalt acetate tetrahydrate and by causing them to react with each other in accordance with the following reaction formula. The following ligand as a raw material for the complex was synthesized on the basis of Tetrahedron, 1999, 55, 8377.

Under a nitrogen atmosphere, 0.303 g of the ligand and 0.324 g of cobalt acetate tetrahydrate were loaded into a 100-mL two-necked flask, and mixed solution of 20 mL of ethanol and 20 mL of chloroform was added thereto. The solution was refluxed for 3 hours, whereby an ocher solid was produced. The precipitate was taken by filtration and dried, whereby Metal Complex (M) was obtained (yield 0.133 g).

ESI-MS [M−OAc]$^+$: 781.0

The Metal Complex (M) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (M).

Metal Complex (P) was synthesized via Compound (N) and Ligand (O) in accordance with the following reaction formula.

Synthesis Example 14

Synthesis of Compound (N)

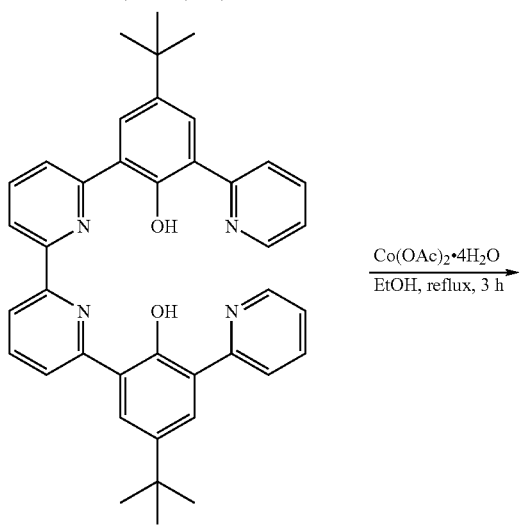

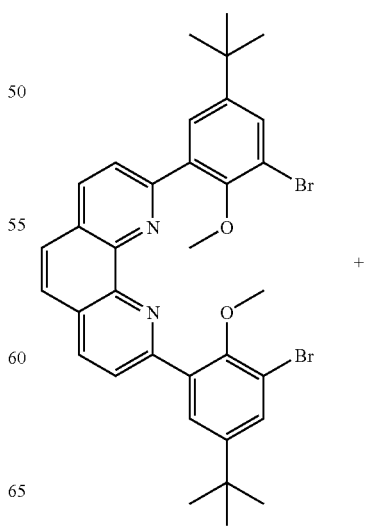

+

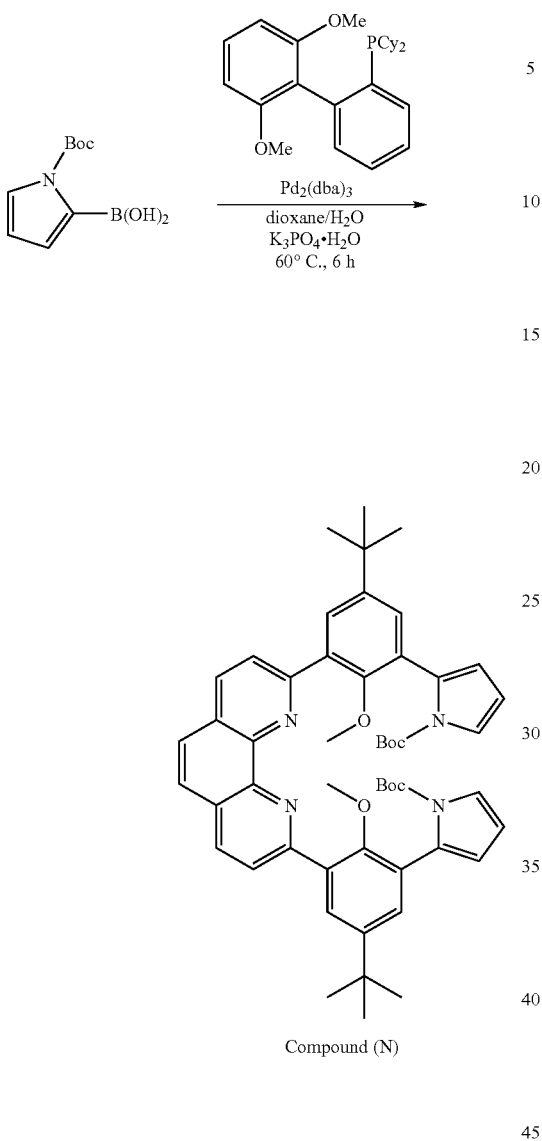

Compound (N)

Synthesis Example 15

Synthesis of Ligand (O)

Synthesis Example 15

Synthesis of Ligand (O)

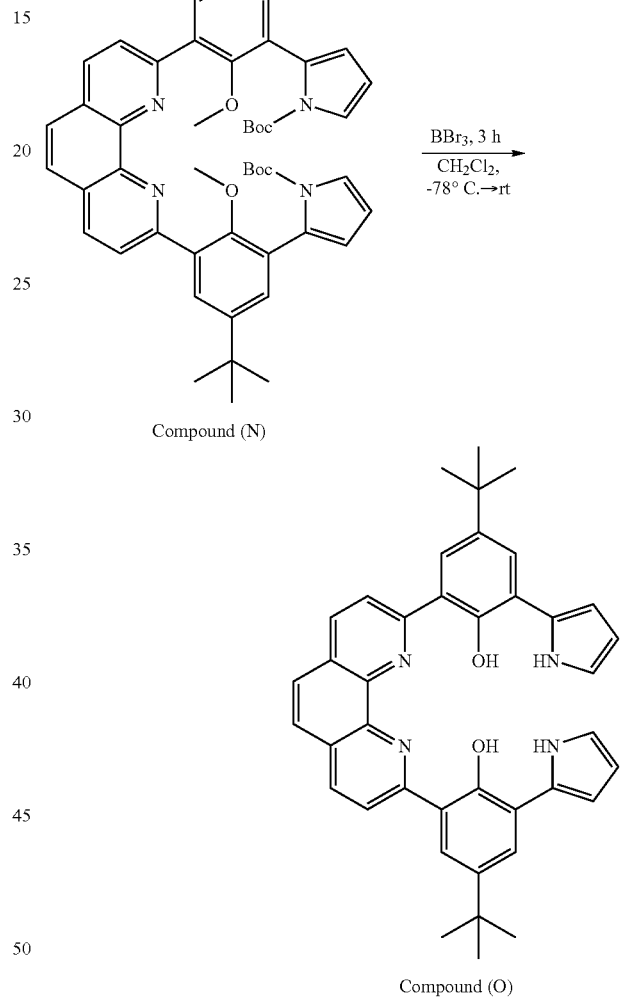

Compound (O)

Under an argon atmosphere, 3.945 g of 2,9-di(3'-bromo-5'-tert-butyl-2'-methoxyphenyl)-1,10-phenanthroline, 3.165 g of 1-N-Boc-pyrrole-2-boronic acid, 0.138 g of tris(benzylideneacetone)dipalladium, 0.247 g of 2-dicyclohexylphosphino-2',6'-dimethoxybiphenyl, and 5.527 g of potassium phosphate were dissolved in mixed solvent of 200 mL of dioxane and 20 mL of water, and the solution was stirred at 60° C. for 6 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, whereby Compound (N) was obtained.

$^1$H-NMR (300 MHz, CDCl$_3$) δ 1.34 (s, 18H), 1.37 (s, 18H), 3.30 (s, 6H), 6.21 (m, 2H), 6.27 (m, 2H), 7.37 (m, 2H), 7.41 (s, 2H), 7.82 (s, 2H), 8.00 (s, 2H), 8.19 (d, J=8.6 Hz, 2H), 8.27 (d, J=8.6 Hz, 2H).

Under a nitrogen atmosphere, 0.904 g of Compound (N) was dissolved in 10 mL of anhydrous dichloromethane. While the dichloromethane solution was cooled to −78° C., 8.8 mL of boron tribromide (1.0-M dichloromethane solution) was slowly dropped to the dichloromethane solution. After the dropping, the mixture was stirred without any change for 10 minutes, and was then left to stand while being stirred so that its temperature might reach room temperature. Three (3) hours after that, the reaction solution was cooled to 0° C., and a saturated aqueous solution of NaHCO$_3$ was added to the solution. After that, an organic layer was extracted by adding chloroform to the mixture, and was then concentrated. The obtained brown residue was purified with a silica gel column, whereby Ligand (O) was obtained.

$^1$H-NMR (300 MHz, CDCl$_3$) δ 1.40 (s, 18H), 6.25 (m, 2H), 6.44 (m, 2H), 6.74 (m, 2H), 7.84 (s, 2H), 7.89 (s, 2H), 7.92 (s, 2H), 8.35 (d, J=8.4 Hz, 2H), 8.46 (d, J=8.4 Hz, 2H), 10.61 (s, 2H), 15.88 (s, 2H)

Synthesis Example 16

Synthesis of Metal Complex (P)

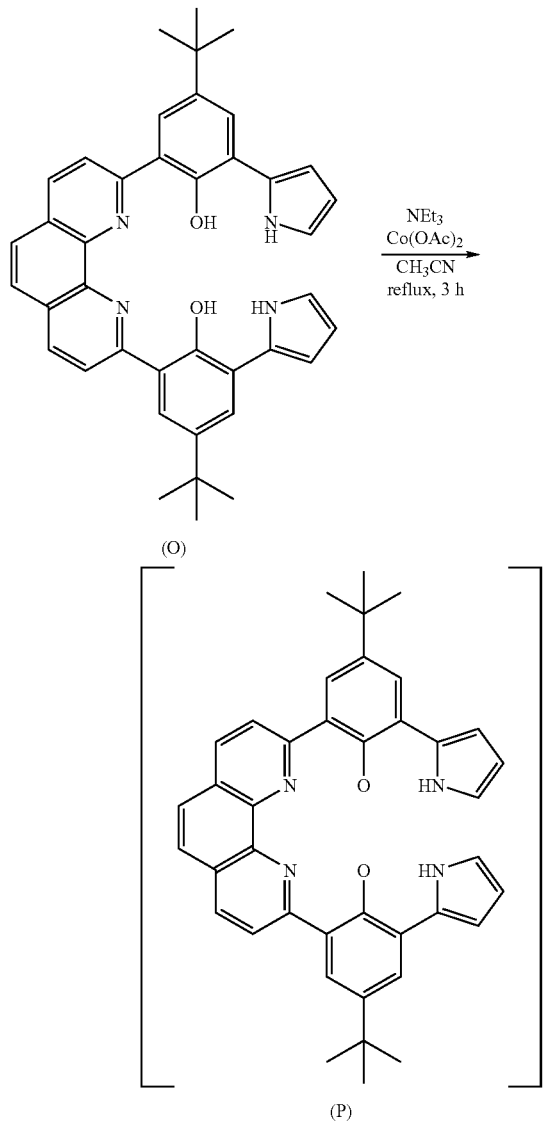

Under a nitrogen atmosphere, 0.100 g of Ligand (O) and solution of 0.040 g of cobalt acetate tetrahydrate in 20 mL of acetonitrile deaerated with Ar were loaded into a 100-mL two-necked flask, and the mixture was stirred at room temperature. Triethylamine in 45 μl was dropped to the solution, and the mixture was refluxed for 3 hours. The solution was concentrated and cooled, and then the resultant solid was taken by filtration with a membrane filter and dried, whereby Metal Complex (P) was obtained (yield 0.098 g).

ESI-MS [M+•]: 663.1

The Metal Complex (P) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (P).

Metal Complex (S) was synthesized via Compound (Q) and Ligand (R) in accordance with the following reaction formula.

Synthesis Example 17

Synthesis of Compound (Q)

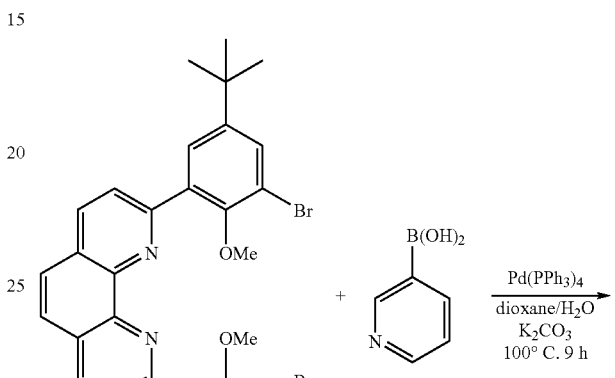

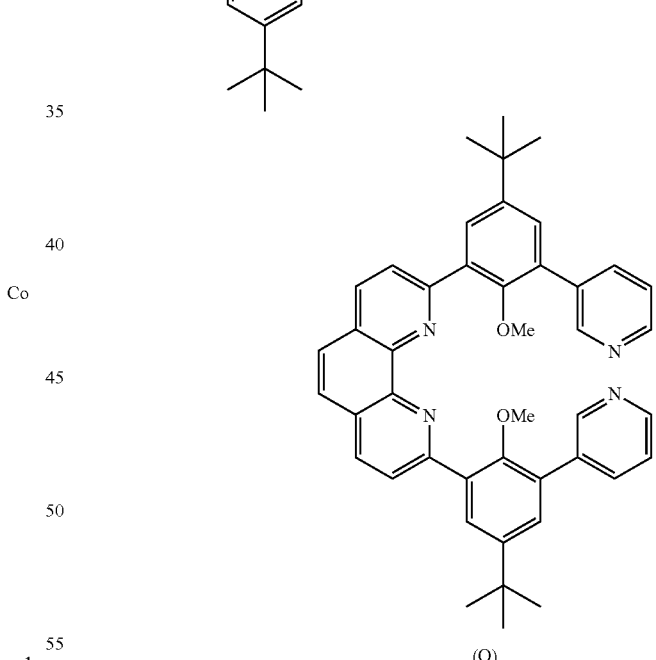

Under an argon atmosphere, 0.132 g of 2,9-di(3'-bromo-5'-tert-butyl-2'-methoxyphenyl)-1,10-phenanthroline, 0.061 g of 3-pyridylboronic acid, 0.046 g of tetrakis(triphenylphosphino)palladium, and 0.111 g of potassium carbonate were dissolved in mixed solvent of 5 mL of dioxane and 0.5 mL of water, and the solution was stirred at 100° C. for 9 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, whereby Compound (Q) was obtained.

Synthesis Example 18

Synthesis of Ligand (R)

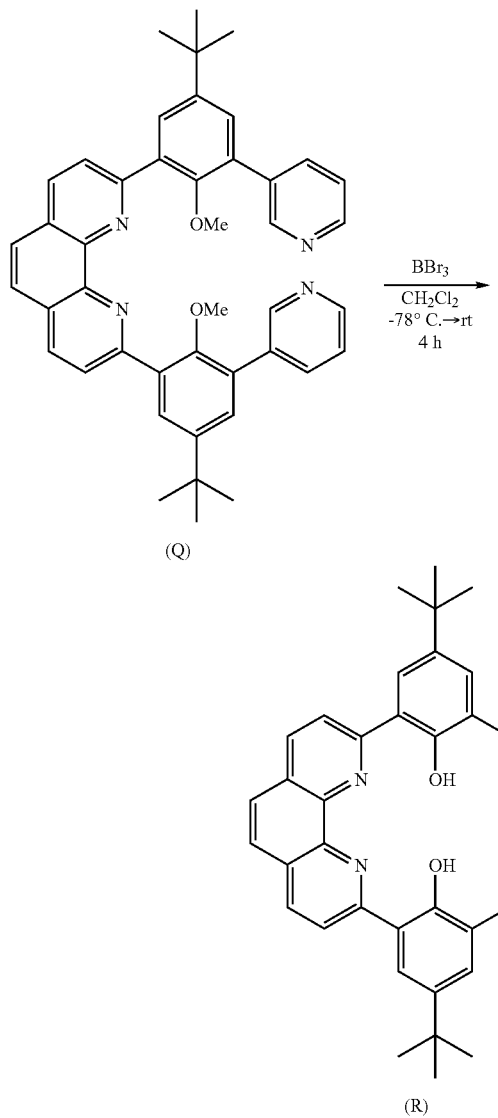

Under a nitrogen atmosphere, 0.110 g of Compound (Q) was dissolved in 3 mL of anhydrous dichloromethane. While the dichloromethane solution was cooled to −78° C. in a dry ice/acetone bath, 1.3 mL of boron tribromide (1.0-M dichloromethane solution) was slowly dropped to the dichloromethane solution. After the dropping, the mixture was stirred without any change for 10 minutes. Then, the dry ice/acetone bath was removed, and the mixture was left to stand while being stirred so that its temperature might reach room temperature. Four (4) hours after that, the resultant was neutralized with a saturated aqueous solution of NaHCO$_3$, and then an organic layer was extracted three times by adding chloroform to the mixture. The obtained organic layer was concentrated, and the obtained residue was purified, whereby Ligand (R) was obtained.

$^1$H-NMR (300 MHz, CDCl$_3$) δ1.47 (s, 18H), 7.44 (t, J=6.2 Hz, 2H), 7.55 (s, 2H), 7.95 (s, 2H), 8.16 (s, 2H), 8.40 (d, J=8.3 Hz, 2H), 8.53 (d, J=8.3 Hz, 2H), 8.67 (d, J=7.5 Hz, 2H), 9.47 (s, 2H), 9.79 (d, J=2.8 Hz, 2H), 15.36 (s, 2H)

Synthesis Example 19

Synthesis of Metal Complex (S)

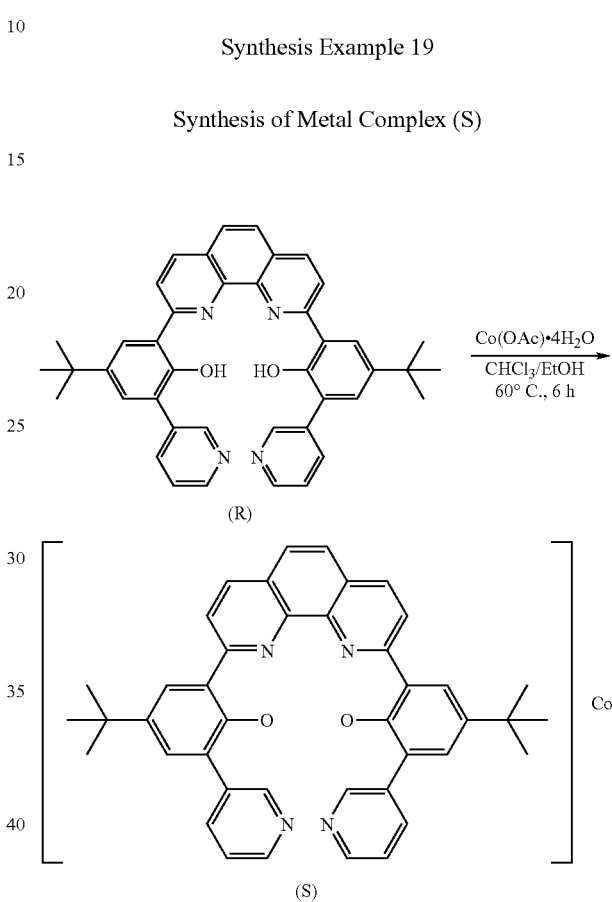

Under a nitrogen atmosphere, 0.096 g of Ligand (R) and mixed solution of 10 mL of chloroform and 4 mL of ethanol containing 0.037 g of cobalt acetate tetrahydrate were loaded into a 100-mL egg plant flask, and the mixture was stirred for 6 hours while being heated to 60° C., whereby a brown solid was produced. The solid was taken by filtration, and was then washed with ethanol and dried, whereby Metal Complex (S) was obtained (yield 0.040 g).

ESI-MS [M+•]: 687.1

The Metal Complex (S) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (S).

Metal Complex (V) was synthesized via Compound (T) and Ligand (U) in accordance with the following reaction formula.

Synthesis Example 20

Synthesis of Compound (T)

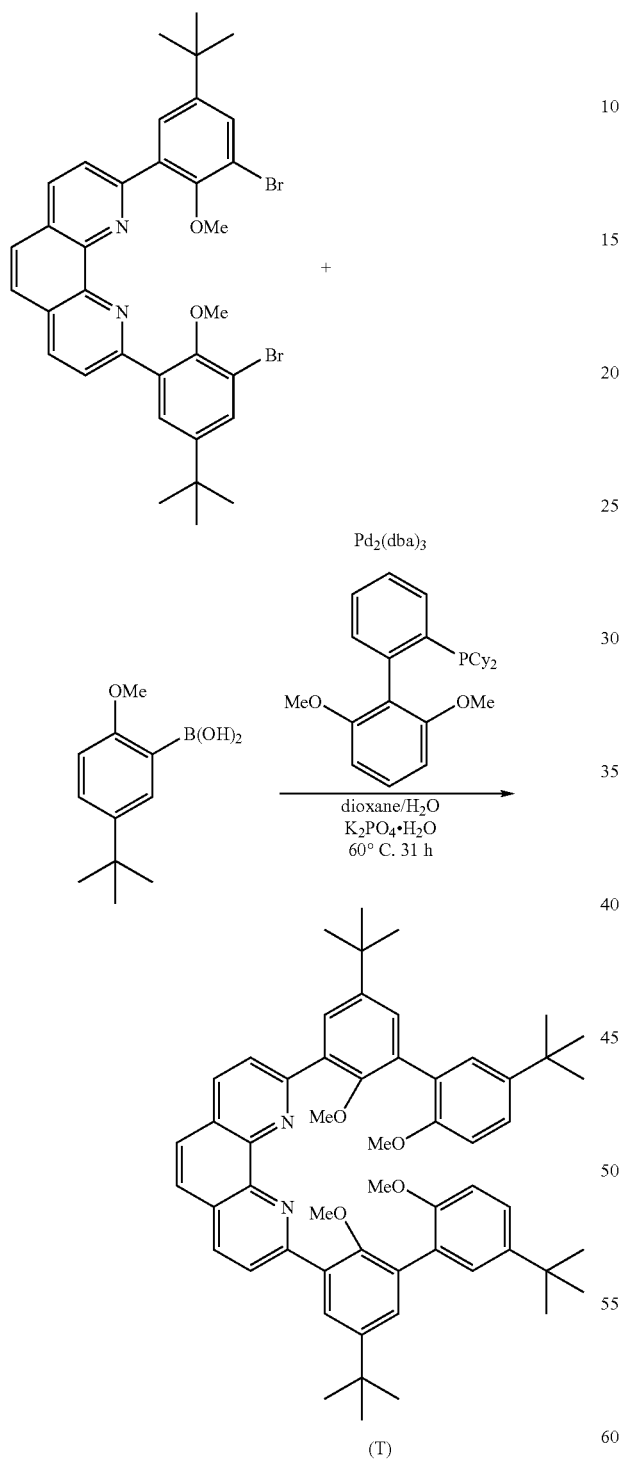

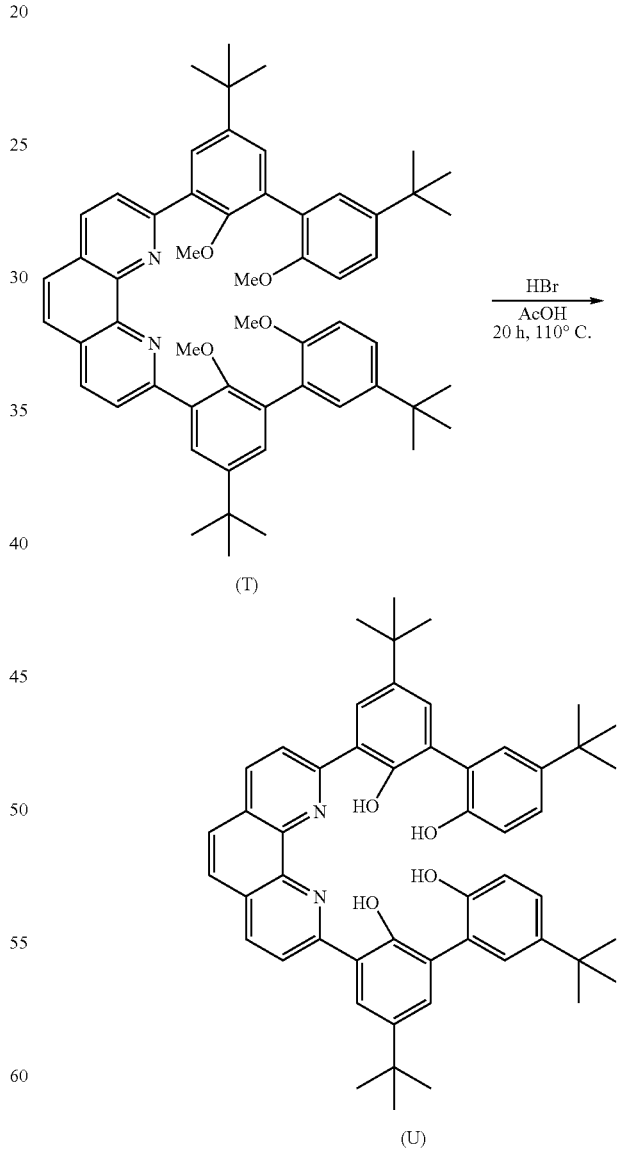

Under an argon atmosphere, 0.662 g of 2,9-di(3'-bromo-5'-tert-butyl-2'-methoxyphenyl)-1,10-phenanthroline, 0.520 g of 2-tert-butyl-5-methoxyphenyl-boronic acid, 0.090 g of tris(benzylideneacetone)dipalladium, 0.160 g of 2-dicyclohexylphosphino-2',6'-dimethoxybiphenyl, and 0.920 g of potassium phosphate were dissolved in mixed solvent of 30 mL of dioxane and 10 mL of water, and the solution was stirred at 60° C. for 31 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, whereby Compound (T) was obtained.

$^1$H-NMR (300 MHz, CDCl$_3$) δ 1.34 (s, 18H), 1.39 (s, 18H), 3.33 (s, 6H), 3.76 (s, 6H), 6.91 (s, 2H), 6.94 (s, 2H), 7.36 (m, 6H), 7.83 (s, 2H), 7.95 (d, J=2.6 Hz, 2H), 8.16 (d, J=8.2 Hz, 2H), 8.26 (d, J=8.2 Hz, 2H)

Synthesis Example 21

Synthesis of Ligand (U)

Under a nitrogen atmosphere, 0.281 g of Compound (T) was dissolved in 5 mL of acetic acid. 0.573 g of 48% hydrobromic acid was dropped to the solution, and the mixture was stirred at 110° C. Twenty (20) hours after that, the reaction solution was cooled to 0° C., and water was added to the solution. After that, an organic layer was extracted by adding chloroform to the mixture, and was then concentrated. The obtained residue was purified with a silica gel column, whereby Ligand (U) was obtained.

$^1$H-NMR (300 MHz, CDCl$_3$) δ 1.40 (s, 18H), 1.44 (s, 18H), 6.59 (s, 2H), 6.62 (s, 2H), 7.35 (m, 6H), 7.53 (s, 2H), 7.89 (s, 2H), 8.01 (s, 2H), 8.38 (d, J=9.0 Hz, 2H), 8.47 (d, J=9.0 Hz, 2H), 16.12 (s, 2H)

Synthesis Example 22

Synthesis of Metal Complex (V)

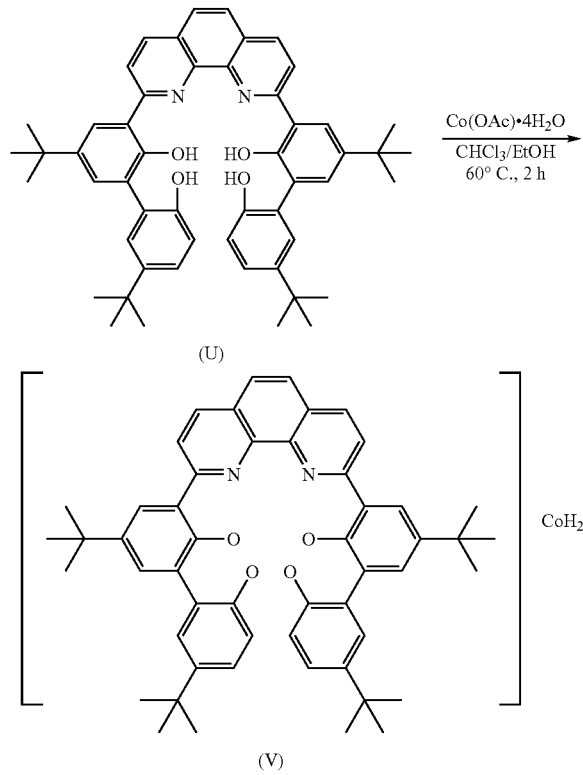

Under a nitrogen atmosphere, 0.077 g of Ligand (U) and mixed solution of 10 mL of chloroform and 2 mL of ethanol containing 0.050 g of cobalt acetate tetrahydrate were loaded into a 25-mL egg plant flask, and the mixture was stirred for 9 hours while being heated at 70° C. The solution was dropped to an Erlenmeyer flask containing 50 mL of diethyl ether. The precipitated solid was taken by filtration, washed with diethyl ether, and dried, whereby Metal Complex (V) was obtained (yield 0.018 g).

ESI-MS [M+•]: 829.3

The Metal Complex (V) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (V).

Reference Example 1

A change in mass (TGA) of each of Metal Complex (A), Metal Complex (B), Metal Complex (D), and Metal Complex (E) upon heat treatment was measured with a thermogravimetric/differential thermal analyzer (EXSTAR-6300 manufactured by Seiko Instruments Inc., hereinafter referred to as thermal analyzer). Conditions for the measurement were as follows: the measurement was performed under a nitrogen atmosphere (at a rate of temperature increase of 10° C./min), and an alumina dish was used in the heat treatment. FIGS. 1 to 4 each show the analysis (analysis chart).

Examples 1 to 21

Based on the findings obtained by the above thermogravimetric analysis results, a heat treatment was carried out in a manner that the mass reduction rate by the heat treatment became 1 mass % or more. That is, each of the metal complexes and the metal complex mixtures was subjected to two-hour heat treatment at an aimed temperature under nitrogen atmosphere using a tubular furnace.

The tubular furnace used for the heat treatment and heat treatment conditions are shown below.

Tubular furnace: EPKRO-14R, program-controllable opening and closing type tubular furnace, manufactured by Isuzu Seisakusho Heat treatment atmosphere: nitrogen gas flow 200 mL/min
Rate of temperature increase and rate of temperature decrease: 200° C./h Table 1 shows the used metal complexes or metal complex mixtures, names of the modified metal complex obtained by the heat treatment, heat treatment temperature, and mass reduction rate after the treatment. Further, the carbon content (elemental analysis value) after the heat treatment is also shown.

TABLE 1

| Example | Used Metal Complex or Metal Complex Mixture | Obtained Modified Metal Complex | Heat Treatment Temperature (° C.) | Mass Reduction Rate (%) | Carbon Content (%) |
|---|---|---|---|---|---|
| 1 | Metal Complex (A) | Modified Metal Complex (A-1) | 600 | 29.26 | 62.06 |
| 2 | Metal Complex Mixture (A) | Modified Metal Complex (A-2) | 600 | 2.52 | 90.92 |
| 3 | Metal Complex (B) | Modified Metal Complex (B-1) | 600 | 20.51 | 67.03 |
| 4 | Metal Complex Mixture (B) | Modified Metal Complex (B-2) | 800 | 7.94 | 94.05 |
| 5 | Metal Complex Mixture (B) | Modified Metal Complex (B-3) | 600 | 4.37 | 93.93 |
| 6 | Metal Complex Mixture (D) | Modified Metal Complex (D) | 800 | 6.06 | 92.64 |
| 7 | Metal Complex (E) | Modified Metal Complex (E-1) | 500 | 28.24 | 59.60 |
| 8 | Metal Complex Mixture (E) | Modified Metal Complex (E-2) | 800 | 6.00 | 93.71 |
| 9 | Metal Complex Mixture (F) | Modified Metal Complex (F) | 800 | 18.52 | 93.43 |
| 10 | Metal Complex (G) | Modified Metal Complex (G-1) | 600 | 25.81 | 69.38 |
| 11 | Metal Complex Mixture (G) | Modified Metal Complex (G-1) | 500 | 4.96 | 93.23 |
| 12 | Metal Complex Mixture (H) | Modified Metal Complex (H) | 500 | 2.88 | 92.95 |
| 13 | Metal Complex Mixture (I) | Modified Metal Complex (I) | 500 | 1.79 | 92.13 |

TABLE 1-continued

| Example | Used Metal Complex or Metal Complex Mixture | Obtained Modified Metal Complex | Heat Treatment Temperature (° C.) | Mass Reduction Rate (%) | Carbon Content (%) |
|---|---|---|---|---|---|
| 14 | Metal Complex Mixture (J) | Modified Metal Complex (J-1) | 500 | 8.74 | 92.30 |
| 15 | Metal Complex Mixture (J) | Modified Metal Complex (J-2) | 350 | 2.00 | 91.07 |
| 16 | Metal Complex Mixture (K) | Modified Metal Complex (K) | 800 | 9.52 | 93.80 |
| 17 | Metal Complex (L) | Modified Metal Complex (L) | 600 | 38.18 | 66.52 |
| 18 | Metal Complex Mixture (P) | Modified Metal Complex (P-1) | 900 | 12.16 | 95.53 |
| 19 | Metal Complex Mixture (P) | Modified Metal Complex (P-1) | 600 | 9.27 | 89.06 |
| 20 | Metal Complex Mixture (S) | Modified Metal Complex (S) | 800 | 11.59 | 91.51 |
| 21 | Metal Complex Mixture (V) | Modified Metal Complex (V) | 800 | 11.24 | 94.59 |

Reference Example 2

Test for Evaluating Modified Metal Complex for Metal Retention Ability

Each of Modified Metal Complex (A-2), Modified Metal Complex (B-1), Modified Metal Complex (B-2), and Modified Metal Complex (E-1) was immersed in a 0.1-mol/L aqueous solution of hydrochloric acid, and was then subjected to an ultrasonic treatment at room temperature for 15 minutes. A metal amount contained in each sample was determined by inductively coupled plasma-atomic emission spectroscopy (ICP-AES), and a metal retention rate was calculated by using the following equation.

Metal retention rate(%)=100−(metal amount eluted into solution side)/(metal amount contained in modified product)×100

Comparative Example 1

In addition, Metal Complex Mixture (C) prepared in Synthesis Example 3 was subjected to a heat treatment at 500° C. in accordance with the method described in Examples 1 to 21, whereby Metal Complex Composition (C) as a comparative reference example was obtained.

The metal retention rate of Metal Complex Composition (C) thus obtained was calculated in accordance with the above method. Metal Complex Composition (C) having no nitrogen-containing aromatic heterocycle was inferior in metal retention ability to Modified Metal Complex (A-2), Modified Metal Complex (B-1), Modified Metal Complex (B-2), and Modified Metal Complex (E-1).

TABLE 2

| Evaluated Sample | Metal Retention Ratio (%) |
|---|---|
| Modified Metal Complex (A-2) | 50 |
| Modified Metal Complex (B-1) | 49 |
| Modified Metal Complex (B-2) | 83 |
| Metal Complex Composition (C) | 25 |
| Modified Metal Complex (E-1) | 88 |

Examples 22 to 26

Laser Raman Spectrum Measurement for Modified Metal Complex

Figure 5:
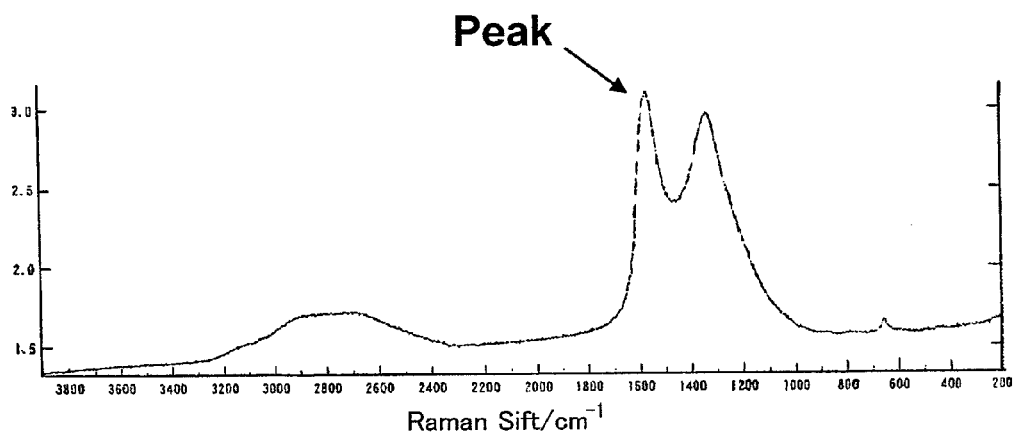
FIG. 5 shows a laser Raman spectrum of the modified metal complex (A-1).
Figure 6:
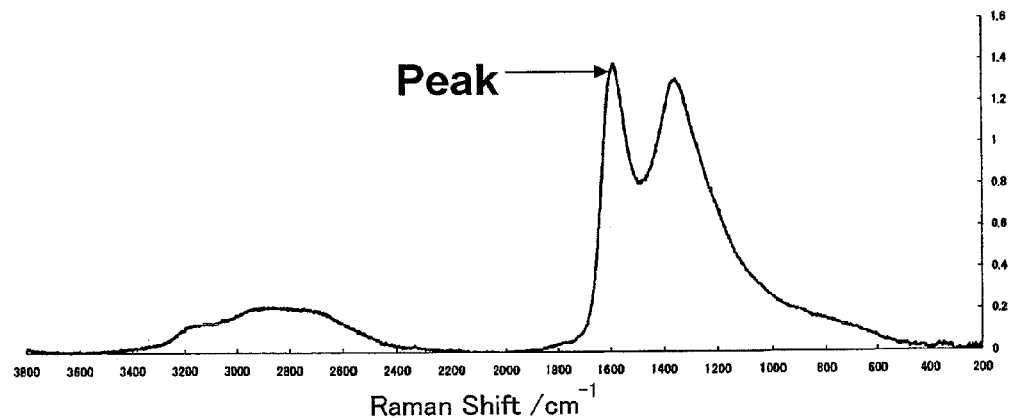
FIG. 6 shows a laser Raman spectrum of the modified metal complex (B-1).
Figure 7:
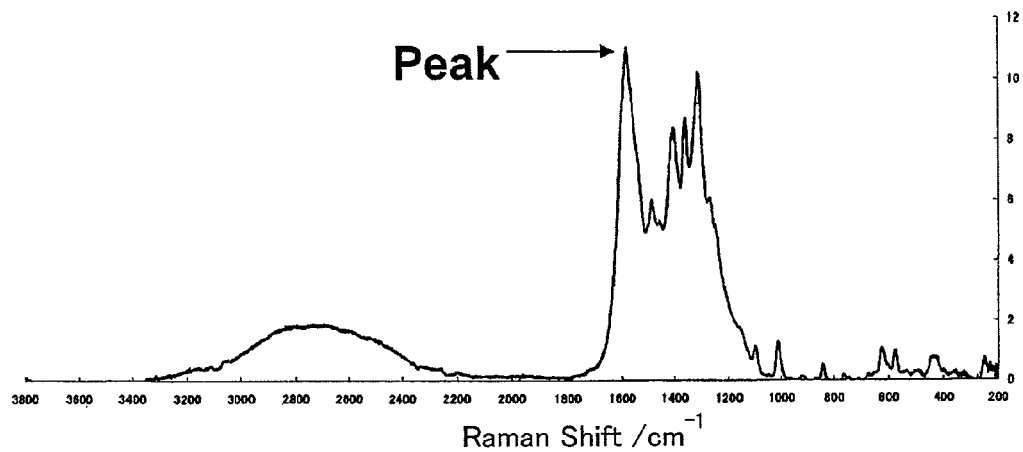
FIG. 7 shows a laser Raman spectrum of the modified metal complex (E-1).
Figure 8:
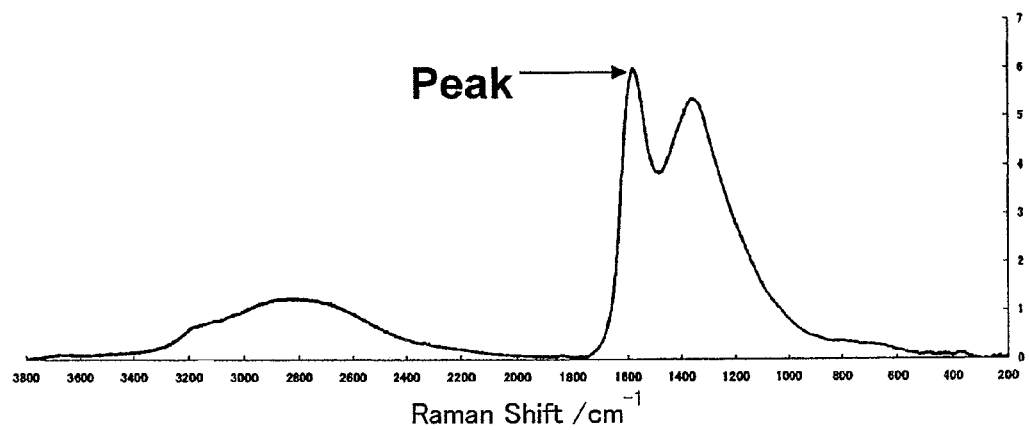
FIG. 8 shows a laser Raman spectrum of the modified metal complex (G-1).
Figure 9:
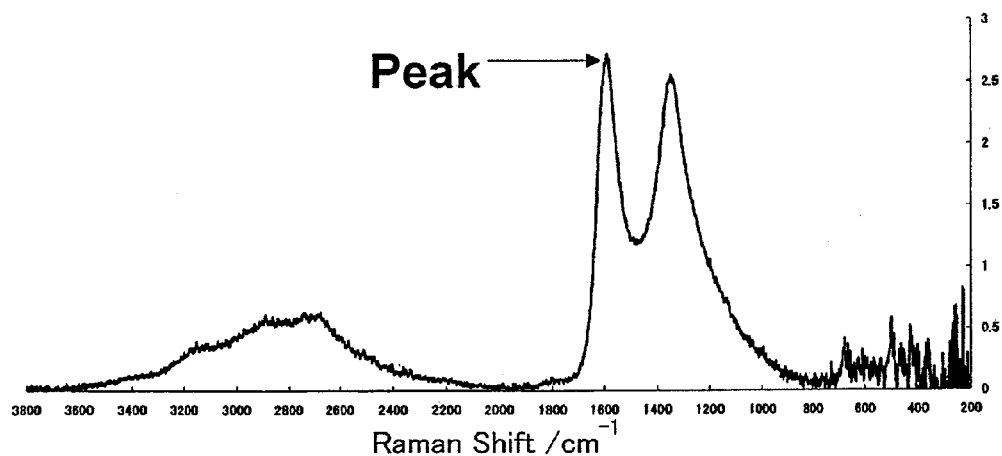
FIG. 9 shows a laser Raman spectrum of the modified metal complex (L).

FIG. 5 shows the laser Raman spectrum of Modified Metal Complex (A-1). The measurement was carried out in the following conditions.
Apparatus used: microscopic laser Raman spectrometer NSR 1000 (JASCO Corporation)
Excitation wavelength: 532 nm
Objective lens: 50 magnification
Measurement range: 200 to 3900 $cm^{-1}$ From FIG. 5, it can be found that Modified Metal Complex (A-1) has a local maximum peak at 1580 $cm^{-1}$. Accordingly, it is implied that graphene-like carbon was produced by the treatment in the obtained modified metal complex.

Each of Modified Metal Complex (B-1), Modified Metal Complex (E-1), Modified Metal Complex (G-1), and Modified Metal Complex (L) was similarly subjected to Raman spectroscopy. FIGS. 6, 7, 8, and 9 illustrate the laser Raman spectra of Modified Metal Complexes (B-1), (E-1), (G-1), and (L), respectively. Each of the charts has a local maximum peak at 1,588 $cm^{-1}$, 1,587 $cm^{-1}$, 1,579 $cm^{-1}$ and 1,592 $cm^{-1}$, respectively, so it is shown that graphene-like carbon is produced in each complex.

Examples 27 and 28

Measurement of Extended X-ray Absorption Fine Structure

Figure 10:
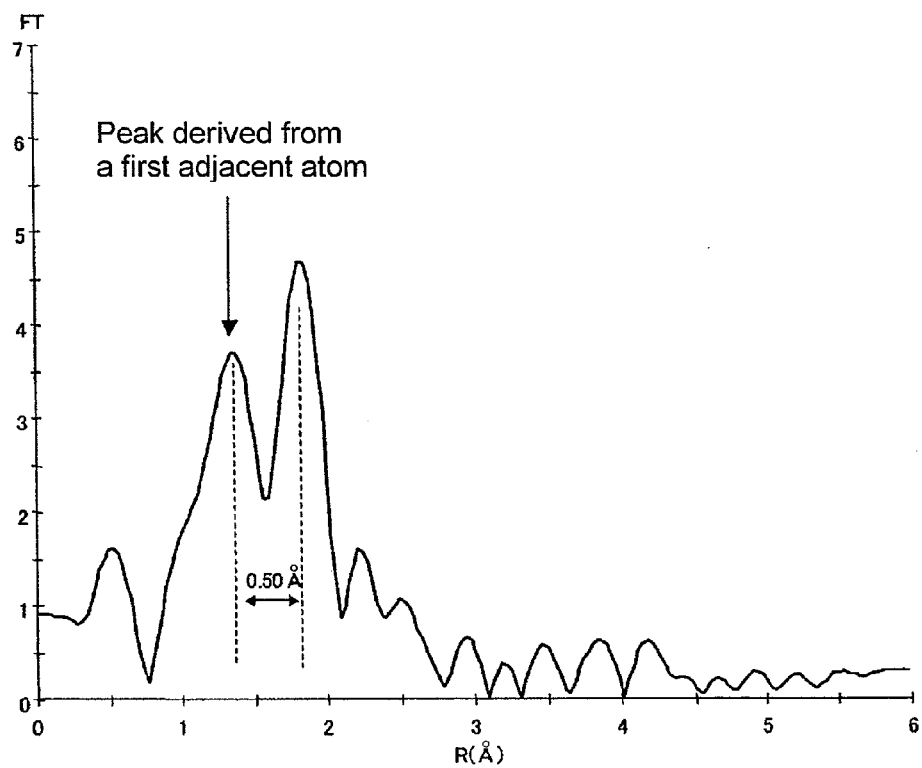
FIG. 10 illustrates a radial distribution function obtained from the extended X-ray absorption fine structure of the modified metal complex (A-2).
Figure 11:
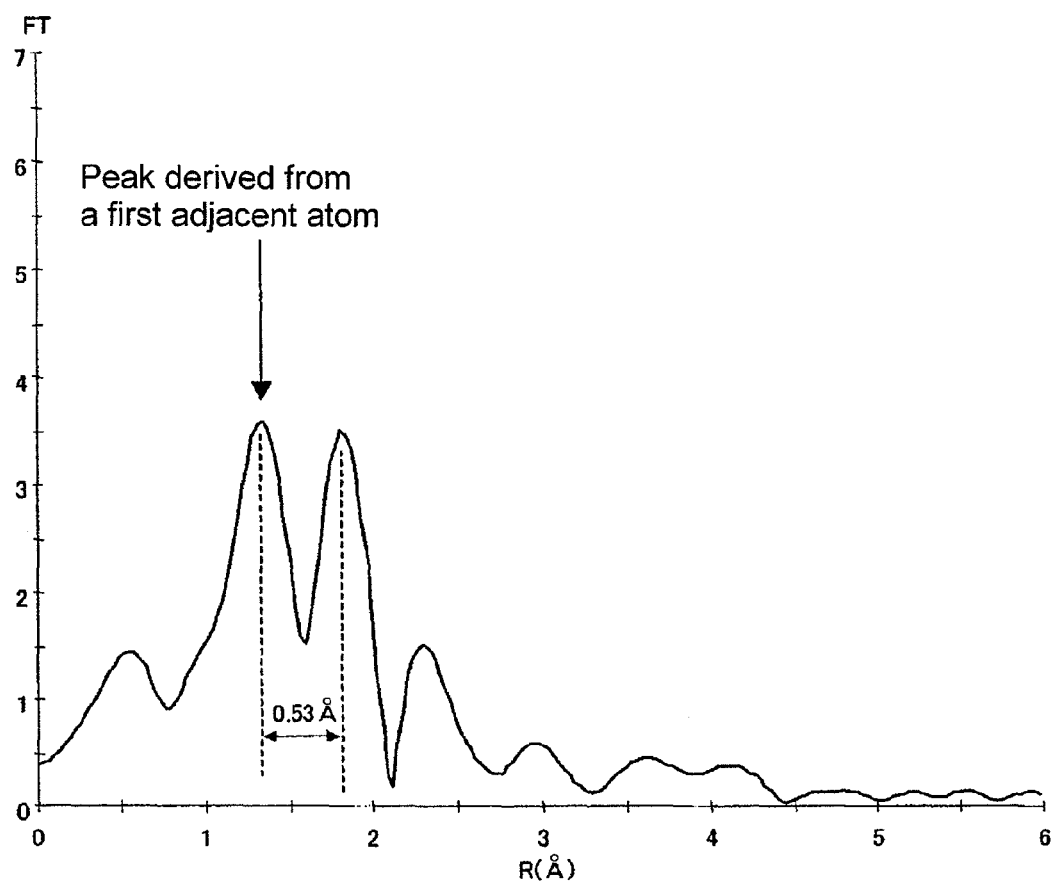
FIG. 11 illustrates a radial distribution function obtained from the extended X-ray absorption fine structure of the modified metal complex (B-2).

Modified Metal Complex (A-2), Modified Metal Complex (B-2), and Modified Metal Complex (P-2) described above were each subjected to an ultrasonic treatment in a hydrochloric acid solution, and were then each dried in a vacuum, whereby Carbon Compound (A-2), Carbon Compound (B-2), and Carbon Compound (P-2) were obtained. The extended X-ray absorption fine structure (EXAFS) of each of those compounds was measured. Beam line (BL-9A, 12C) of the Photon Factory of the High Energy Accelerator Research Organization was used in the EXAFS measurement. A pelletized sample having a diameter of 10 mm was cooled to a temperature of 20 K, and was measured by a transmission method. A radial distribution function was determined by subjecting the X-ray absorption spectrum obtained by the measurement to Fourier transformation. FIGS. 10 and 11 illustrate the radial distribution functions of Carbon Compound (A-2) and Carbon Compound (B-2), respectively. As can be seen from the figures, Carbon Compound (A-2) has a peak at 0.50 Å from the peak derived from the first adjacent atom [the term "first adjacent atom" as used herein refers to an atom (atomic group) closest to the central metal serving as a measurement object in EXAFS analysis, and, for example, a heteroatom such as an oxygen atom or a nitrogen atom positioned at a distance in the range of 1.0 Å or more and 2.5 Å or less from the central metal corresponds to the first adjacent atom], and Carbon Compound (B-2) has a peak at 0.53 Å from the peak derived from the first adjacent atom. It should be noted that the EXAFS of a cobalt metal foil was measured with the beam line at room temperature, and a peak derived from a cobalt metal was observed at 2.19 Å in the resultant radial distribution function. The term "peak" as used herein refers to a peak whose intensity value is one half or more of the maximum intensity value. Carbon Compound (P-2) was subjected to the same measurement; in the resultant radial distribution function, a peak derived from the first adjacent atom was observed at 1.35 Å, and the compound was found to have a peak at 0.49 Å from the peak.

Comparative Example 2

Measurement of Extended X-ray Absorption Fine Structure

In addition, 5,10,15,20-tetraphenyl-21H,23H-porphine cobalt(II) (manufactured by Sigma-Aldrich Co.) and a carbon carrier (Ketjen Black EC300J manufactured by Lion Corporation) were mixed at a weight ratio of 1:4. The mixture was stirred in ethanol at room temperature, and was then dried at room temperature under a reduced pressure of 1.5 Torr for 12 hours, whereby Metal Complex Mixture (W) as a comparative example was prepared. The metal complex mixture was subjected to a heat treatment at 600° C. in the same manner as that described above, whereby Modified Metal Complex (W) was prepared (mass reduction rate 1.67%, carbon content 92.95%).

Modified Metal Complex (W) was subjected to an ultrasonic treatment in a hydrochloric acid solution, and was then dried in a vacuum, whereby Carbon Compound (W) was obtained. The extended X-ray absorption fine structure (EX-AFS) of the complex was measured in the same manner as that described above, and a radial distribution function was determined. As a result, a peak derived from the first adjacent atom to cobalt was observed at 1.44 Å, but no other peak was observed.

Reference Example 3

Hydrogen Peroxide Decomposition Test for Modified Metal Complex (E-1)

A two-neck flask was loaded with 3.6 mg (about 8 μmol (per 1 metal atom) of Modified Metal Complex (E-1) and a tartaric acid/sodium tartarate buffer solution (1.00 mL (prepared from an aqueous 0.20 mol/L tartaric acid solution and an aqueous 0.10 mol/L sodium tartarate solution, pH 4.0) and ethylene glycol (1.00 mL) were added as solvents to the flask, and then stirred. The obtained solution was used as a catalyst-mixed solution.

A septum was attached to one neck of the two-neck flask containing the catalyst-mixed solution and the other neck was joined to a gas burette. After the flask was stirred at 80° C. for 5 minutes, an aqueous hydrogen peroxide solution (11.4 mol/L, 0.20 mL (2.28 mmol)) was added with a syringe and hydrogen peroxide decomposition reaction was carried out at 80° C. for 20 minutes. The generated oxygen was measured with gas burette to quantitatively measure the decomposed hydrogen peroxide.

The decomposed hydrogen peroxide amount was calculated from the gas volume containing the oxygen generated in the hydrogen peroxide decomposition test. The generated gas volume value v by actual measurement was converted into the following gas volume V at 0° C. and 101325 Pa (760 mmHg) in consideration of the vapor pressure of water.

Figure 12:
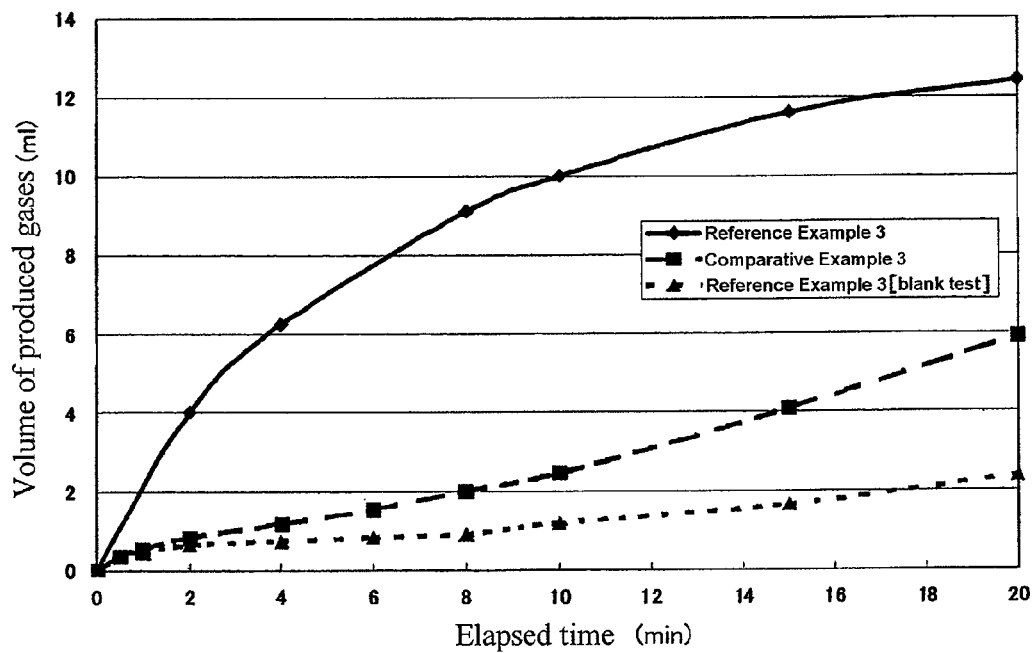
FIG. 12 shows results of a hydrogen peroxide decomposition test of the modified metal complex (E-1) and the metal complex (E).

The result is shown in FIG. 12. It was confirmed that Modified Metal Complex (E-1) of the invention had high generated gas volume as compared with that in the blank test described below and thus had a catalytic effect on hydrogen peroxide decomposition.

$$V = \frac{273v(P-p)}{760(273+t))}$$

(In the formula, P: atmospheric pressure (mmHg), p: vapor pressure of water (mmHg), t: temperature (° C.), v: actually measured generated gas volume (mL), V: gas volume (mL) at 0° C. and 101325 Pa (760 mmHg)).

[Blank Test]

A two-neck flask was loaded with 1.00 mL of a tartaric acid/sodium tartarate buffer solution (produced from an aqueous 0.20 mol/L tartaric acid solution and an aqueous 0.10 mol/L sodium tartarate solution, pH 4.0) and 1.00 mL of ethylene glycol as solvents. A septum was attached to one neck of the two-neck flask and the other neck was joined to a gas burette. After the flask was stirred at 80° C. for 5 minutes, an aqueous hydrogen peroxide solution (11.4 mol/L, 0.20 mL (2.28 mmol)) was added and the generated gas was quantitatively measured with the gas burette.

It was presumed that air dissolved in the solution could be mainly detected in this blank test.

Comparative Example 3

Hydrogen Peroxide Decomposition Test for Metal Complex (E)

The same test as that in Reference Example 3 was carried out except that Modified Metal Complex (E-1) in Reference Example 3 was changed to Metal Complex (E). The result is shown together with result of Reference Example 3 in FIG. 12.

These results have shown that the modified metal complex obtained by the modification treatment shows a higher oxygen-reducing ability under an acidic condition than the complex does.

Synthesis Example 31

Synthesis of Metal Complex (3A)

Metal complex (3A) was synthesized by mixing a ligand and ethanol solution containing cobalt acetate tetrahydrate and by causing them to react with each other in accordance with the following reaction formula. The following ligand as a raw material for the complex was synthesized on the basis of Tetrahedron, 1999, 55, 8377.

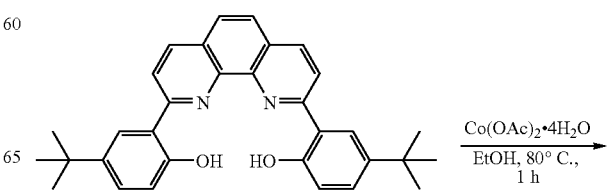

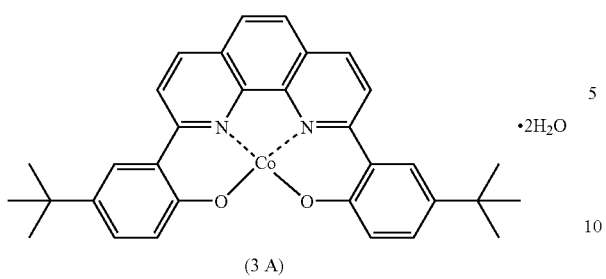

(3 A)

Under a nitrogen atmosphere, 0.300 g of the ligand and solution of 0.149 g of cobalt acetate tetrahydrate in 4 mL of ethanol were loaded into a 25-mL egg plant flask, and the mixture was stirred for 1 hour while being heated at 80° C., whereby a brown solid was produced. The solid was taken by filtration, and was then washed with ethanol and dried, whereby Metal Complex (3A) was obtained (yield 0.197 g).

Elementary Analysis Value (%):

Calculated Value (Calcd for $C_{32}H_{34}CoN_2O_4$); C, 67.48; H, 6.02; N, 4.92

Actual Measurement Value: C, 68.29; H, 5.83; N, 4.35

ESI-MS [M+•]: 533.1

The Metal Complex (3A) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (3B).

Metal Complex (3E) was synthesized via Compound (3C) and Ligand (3D) in accordance with the following reaction formula.

Synthesis Example 32

Synthesis of Compound (3C)

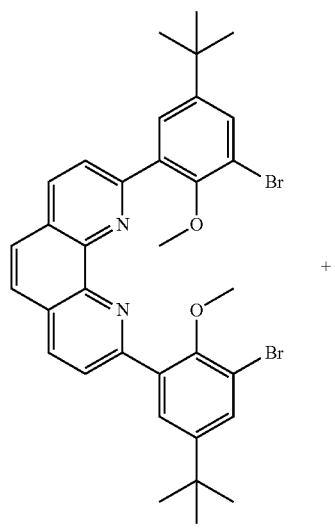

+

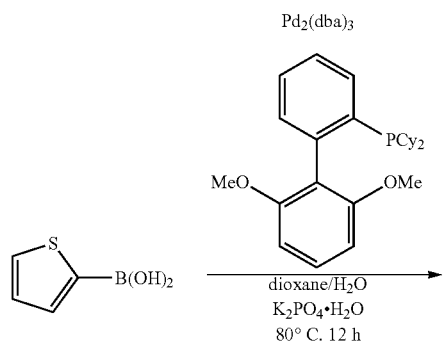

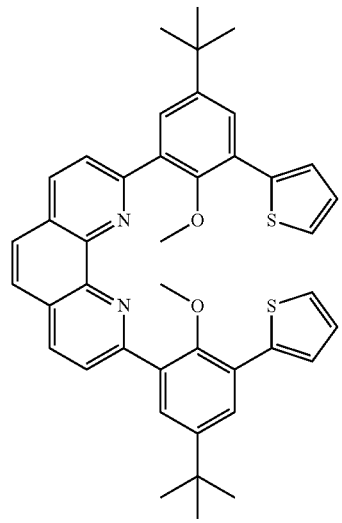

Under an argon atmosphere, 0.662 g of 2,9-di(3'-bromo-5'-tert-butyl-2'-methoxyphenyl)-1,10-phenanthroline, 0.320 g of 2-thienylboronic acid, 0.090 g of tris(benzylideneacetone)dipalladium, 0.160 g of 2-dicyclohexylphosphino-2',6'-dimethoxybiphenyl, and 0.920 g of potassium phosphate were dissolved in a mixed solvent of 30 mL of dioxane and 5 mL of water, and the solution was stirred at 80° C. for 12 hours. After the completion of the reaction, the solution was left standing to cool, distilled water and chloroform were added to the solution, and an organic layer was extracted. The resultant organic layer was concentrated, whereby a black residue was obtained. The residue was purified with a silica gel column, and then the purified product was recrystallized, whereby Compound (3C) was obtained.

$^1$H-NMR (300 MHz, CDCl$_3$) δ 1.42 (s, 18H), 3.48 (s, 6H), 7.12 (dd, 2H), 7.38 (d, J=5.0 Hz, 2H), 7.52 (d, J=2.9 Hz, 2H), 7.73 (s, 2H), 7.87 (s, 2H), 7.98 (s, 2H), 8.28 (d, J=8.6 Hz, 2H), 8.30 (d, J=8.6 Hz, 2H)

Synthesis Example 33

Synthesis of Ligand (3D)

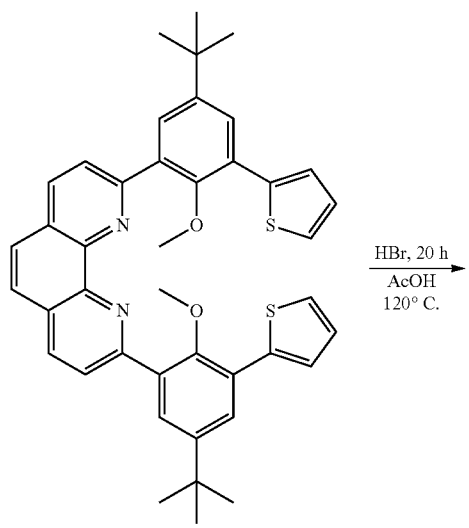

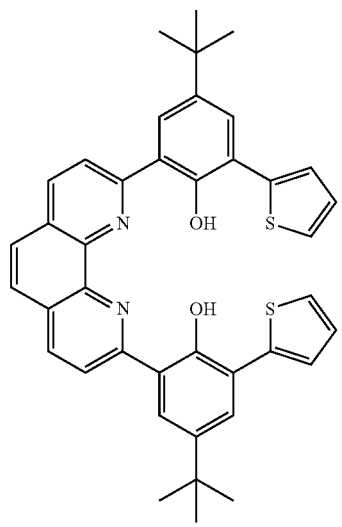

Under a nitrogen atmosphere, 0.134 g of Compound (3C) was dissolved in 5 mL of acetic acid. 0.337 g of 48% hydrobromic acid was dropped to the solution, and the mixture was stirred at 120° C. Twenty (20) hours after that, the reaction solution was cooled to 0° C., and water was added to the solution. After that, an organic layer was extracted by adding chloroform to the mixture, and was then concentrated. The obtained residue was purified with a silica gel column, whereby Ligand (3D) was obtained.

$^1$H-NMR (300 MHz, CDCl$_3$) δ 1.40 (s, 18H), 6.25 (m, 2H), 6.44 (m, 2H), 6.74 (m, 2H), 7.84 (s, 2H), 7.89 (s, 2H), 7.92 (s, 2H), 8.35 (d, J=8.4 Hz, 2H), 8.46 (d, J=8.4 Hz, 2H), 10.61 (s, 2H), 15.88 (s, 2H).

Synthesis Example 34

Synthesis of Metal Complex (3E)

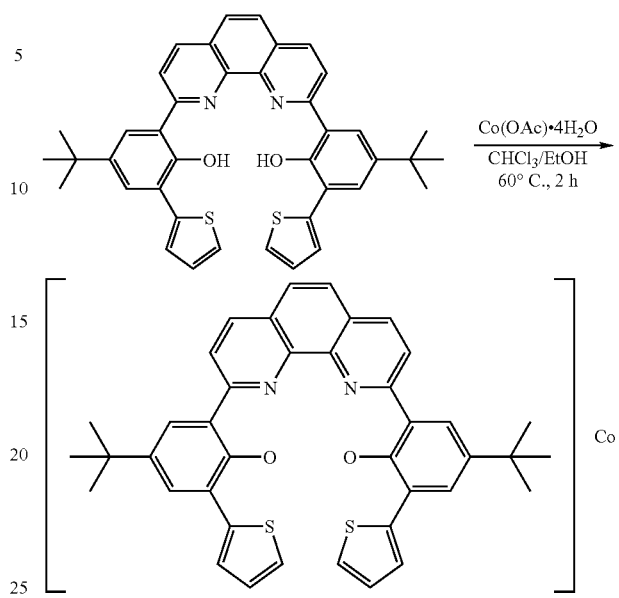

Under a nitrogen atmosphere, 0.062 g of Ligand (3D) and mixed solution of 2 mL of chloroform and 6 mL of ethanol containing 0.025 g of cobalt acetate tetrahydrate were loaded into a 25-mL egg plant flask, and the mixture was stirred for 2 hours while being heated at 60° C., whereby a brown solid was produced. The solid was taken by filtration, and was then washed with ethanol and dried, whereby Metal Complex (3E) was obtained (yield 0.034 g).

ESI-MS [M+•]: 697.0.

The Metal Complex (3E) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (3F).

Metal Complex (3I) was synthesized via Compound (3G) and Ligand (3H) in accordance with the following reaction formula.

Synthesis Example 35

Synthesis of Compound (3G)

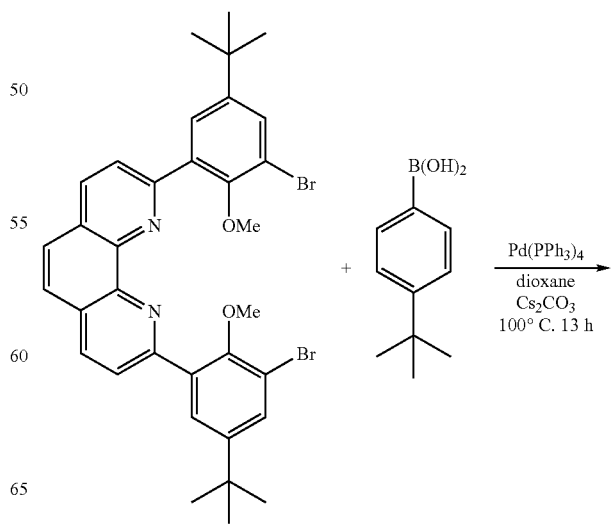

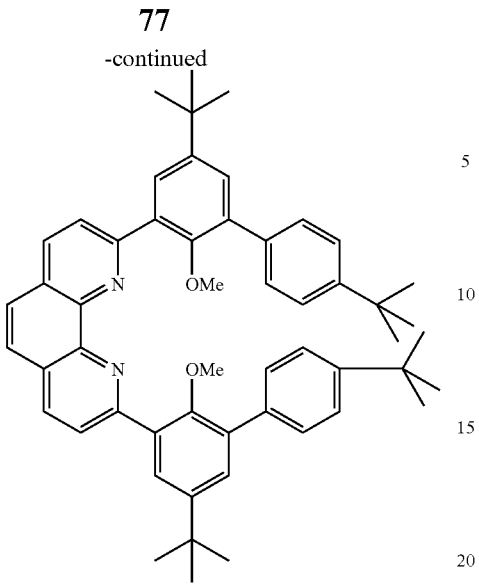

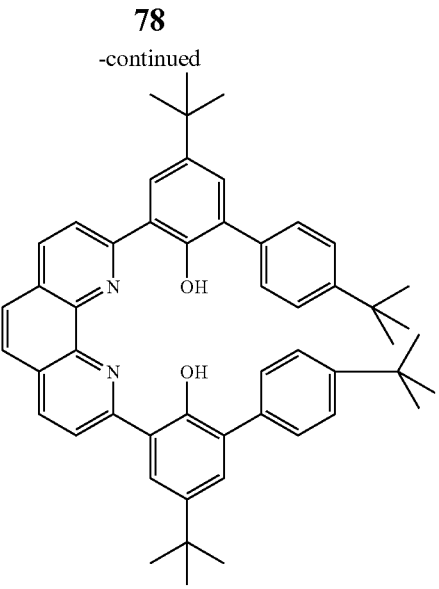

Under an argon atmosphere, 0.528 g of 2,9-di(3'-bromo-5'-tert-butyl-2'-methoxyphenyl)-1,10-phenanthroline, 0.356 g of 4-tert-butylphenylboronic acid, 0.184 g of tetrakis(triphenylphosphino)palladium, and 1.042 g of cesium carbonate were dissolved in 20 mL of dioxane, and the solution was stirred at 100° C. for 13 hours. After the completion of the reaction, the solution was left standing to cool, distilled water and chloroform were added to the solution, and an organic layer was extracted. The resultant organic layer was concentrated and purified with a silica gel column, whereby Compound (3G) was obtained.

$^1$H-NMR (300 MHz, CDCl$_3$) δ 1.39 (s, 18H), 1.40 (s, 18H), 3.31 (s, 6H), 7.44 (s, 2H), 7.46 (d, J=7.0 Hz, 4H), 7.55 (d, J=7.0 Hz, 4H), 7.86 (s, 2H), 7.99 (s, 2H), 8.23 (d, J=8.0 Hz, 2H), 8.29 (d, J=8.4 Hz, 2H)

Synthesis Example 36

Synthesis of Ligand (3H)

Under a nitrogen atmosphere, 0.242 g of Compound (3G) was dissolved in 10 mL of anhydrous dichloromethane. While the dichloromethane solution was cooled to −78° C. in a dry ice/acetone bath, 2.4 mL of boron tribromide (1.0-M dichloromethane solution) was slowly dropped to the dichloromethane solution. After the dropping, the mixture was stirred without any change for 10 minutes. Then, the dry ice/acetone bath was removed, and the mixture was left to stand while being stirred so that its temperature might reach room temperature. Two (2) hours after that, the resultant was neutralized with a saturated aqueous solution of NaHCO$_3$, and then an organic layer was extracted three times by adding chloroform to the mixture. The obtained organic layer was concentrated, and the obtained residue was purified with silica gel, whereby Ligand (3H) was obtained.

$^1$H-NMR (300 MHz, CDCl$_3$) δ 1.34 (s, 18H), 1.43 (s, 18H), 7.39 (d, J=7.3 Hz, 4H), 7.55 (s, 2H), 7.72 (d, J=7.3 Hz, 4H), 7.92 (s, 2H), 8.27 (d, J=8.4 Hz, 2H), 8.38 (d, J=8.4 Hz, 2H), 14.81 (s, 2H)

Synthesis Example 37

Synthesis of Metal Complex (3I)

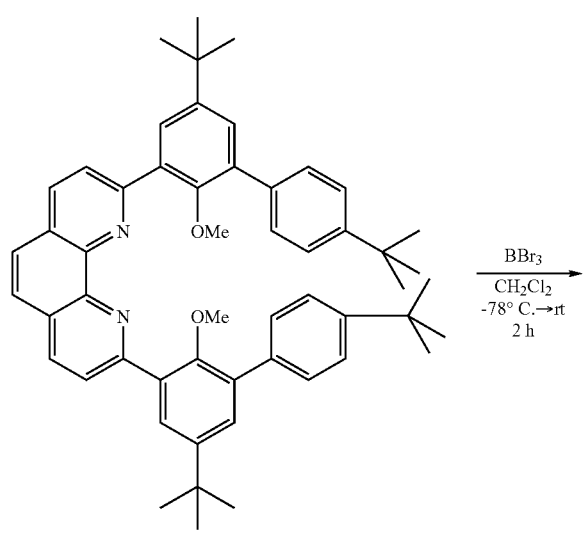

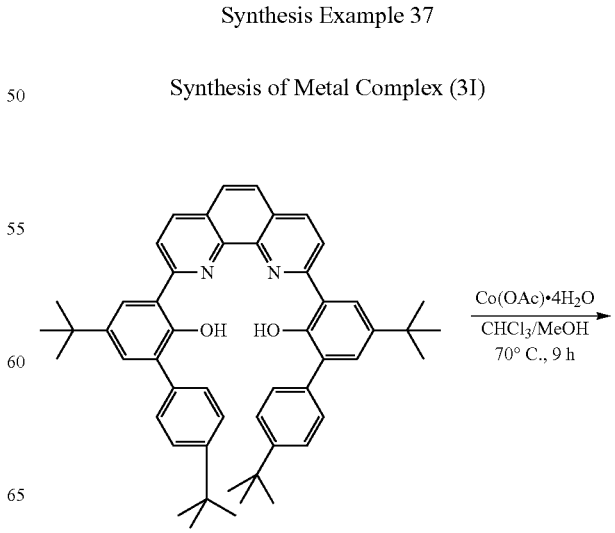

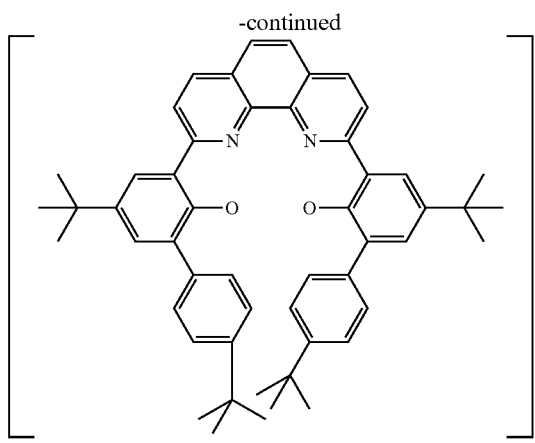

Under a nitrogen atmosphere, 0.085 g of Ligand (3H) and mixed solution of 10 mL of chloroform and 4 mL of ethanol containing 0.031 g of cobalt acetate tetrahydrate were loaded into a 100-mL egg plant flask, and the mixture was stirred for 9 hours while being heated to 70° C. The solution was condensed, and the deposited solid was dissolved in 5 mL of chloroform. The solution was dropped to an Erlenmeyer flask containing 50 mL of diethyl ether. The precipitated solid was taken by filtration, washed with diethyl ether, and dried, whereby Metal Complex (3I) was obtained (yield 0.018 g).

ESI-MS [M+•]: 799.3

The Metal Complex (3I) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (3J).

Synthesis Example 38

Synthesis of Metal Complex (3K)

The Schiff base ligand as a raw material for the complex and Metal Complex (3K) were each synthesized in accordance with the method described in A chemistry, European Journal, 1999, 5, 1460.

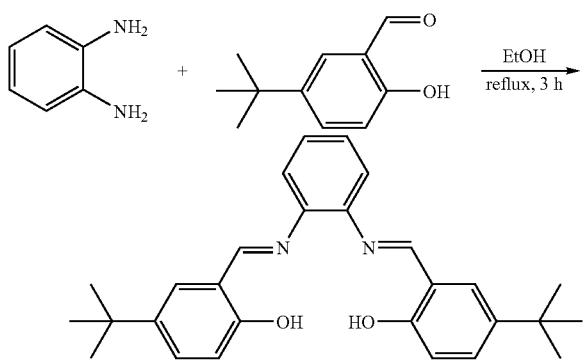

Under a nitrogen atmosphere, solution of 0.303 g of o-phenylenediamine and 1.00 g of 4-tert-butyl-2-formylphenol in 10 mL of ethanol was charged into a 50-mL egg plant flask, and the solution was stirred at 80° C. for 3 hours. The deposited orange precipitate was filtrated, washed, and dried, whereby the Schiff base ligand was obtained (yield 0.838 g, 70%).

$^1$H-NMR; δ: 12.83 (s, 2H), 8.64 (s, 2H), 7.41 (d, 8.7 Hz, 2H), 7.36-7.32 (m, 4H), 7.25-7.21 (m, 4H), 6.99 (d: 8.7 Hz, 2H), 1.32 (s, 18H)

Subsequently, Metal Complex (3K) was synthesized by mixing chloroform containing the Schiff base ligand and ethanol containing cobalt acetate tetrahydrate and by causing them to react with each other.

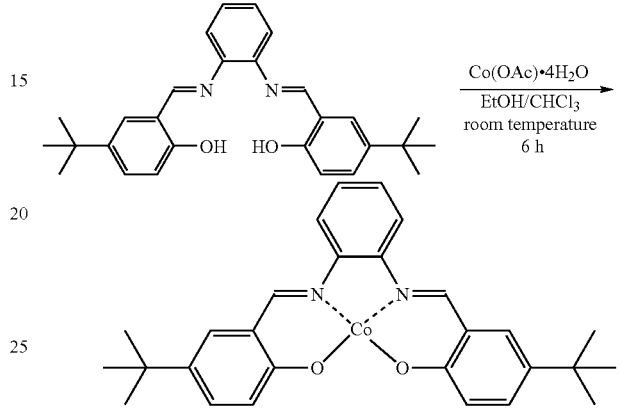

Seven (7) mL of ethanol containing 0.125 g of cobalt acetate tetrahydrate was added to a 25-mL egg plant flask containing solution of 0.214 g of the Schiff base ligand in 3 mL of chloroform while the chloroform solution was stirred. Then, the mixture was stirred at room temperature for 6 hours. The deposited brown precipitate was taken by filtration, washed with ethanol, and dried in a vacuum, whereby Metal Complex (3K) was obtained (yield 0.138 g).

Elementary Analysis Value (%):
Calculated Value (Calcd for $C_{28}H_{34}CoN_2O_4$); C, 64.49; H, 6.57; N, 5.37
Actual Measurement Value: C, 64.92; H, 6.13; N, 5.06
ESI-MS [M+•]: 485.1

The Metal Complex (3K) and a carbon carrier (Ketjen Black EC300J (trade name) manufactured by Lion Corporation) were mixed with each other in a mass ratio of 1:4 and the mixture was stirred at room temperature in ethanol. Then, the mixture was dried at room temperature under a reduced pressure of 1.5 Torr for 12 hours to prepare Metal Complex Mixture (3L).

Examples 31, 32, 33 and 34

With respect to Metal Complex Mixture (3B) prepared in the foregoing, based on the findings obtained by the thermogravimetric analysis results, a heat treatment was carried out in a manner that the mass reduction rate by the heat treatment became 1 mass % or more. That is, Mononuclear Complex Mixture (3B) was subjected to two-hour heat treatment at an aimed temperature under nitrogen atmosphere using a tubular furnace.

The tubular furnace used for the heat treatment and heat treatment conditions are shown below.
Tubular furnace: EPKRO-14R, program-controllable opening and closing type tubular furnace, manufactured by Isuzu Seisakusho
Heat treatment atmosphere: nitrogen gas flow 200 mL/min
Rate of temperature increase and rate of temperature decrease: 200° C./h Table 3 shows the used metal complex mixtures, heat treatment temperature, and mass reduction rate after the treatment. Further, the carbon content (elemental analysis value) after the heat treatment is also shown.

TABLE 3

| Example | Used Metal Complex Mixture | Heat Treatment Temperature (° C.) | Mass Reduction Rate (%) | Carbon Content (%) |
|---|---|---|---|---|
| 31 | Metal Complex Mixture (3B) | 600 | 8.90 | 92.68 |
| 32 | Metal Complex Mixture (3B) | 800 | 9.26 | 93.32 |
| 33 | Metal Complex Mixture (3F) | 800 | 10.71 | 92.60 |
| 34 | Metal Complex Mixture (3J) | 800 | 6.00 | 94.50 |

Here, modified metal complexes obtained by heat treatments to Metal Complex Mixtures (3B), (3F) and (3J) described above are referred to as Modified Metal Complex (3B-1), Modified Metal Complex (3B-2), Modified Metal Complex (3F-1), and Modified Metal Complex (3J-1), respectively.

Reference Example 31

Modified Metal Complex (3B-1) obtained in Example 31 was immersed in a 0.1-mol/L aqueous solution of hydrochloric acid, and was then subjected to an ultrasonic treatment at room temperature for 15 minutes. A metal amount contained in the sample was determined by ICP emission spectroscopy, and a metal retention rate was calculated by using the following equation.

Metal retention rate(%)=(metal amount after acid treatment)/(metal amount before acid treatment)

Table 4 shows the metal retention rate of Modified Metal Complex (3B-1).

In addition, Metal Complex Mixture (3L) prepared in Synthesis Example 38 was subjected to a heat treatment at 450° C. in accordance with the method described in Example 31, whereby Metal Complex Composition (3L-1) as a comparative reference example was obtained. The metal retention rate of Metal Complex Composition (3L-1) thus obtained was calculated in accordance with the above method. Table 4 shows the result. Metal Complex Composition (3L-1) having no nitrogen-containing aromatic heterocyclic structure was inferior in metal retention ability to Modified Metal Complex (3B-1).

TABLE 4

| Evaluated Sample | Metal Retention Rate (%) |
|---|---|
| Modified Metal Complex (3B-1) | 62% |
| Metal Complex Composition (3L-1) | 42% |

Examples 35, 36 and 37

Preparation of Electrode

As the electrode, a ring disk electrode was used in which the disk part was made of glassy carbon (4.0 mmϕ) and the ring part was made of Pt (ring inside diameter: 5.0 mm, ring outside diameter: 7.0 mm).

0.5 mL of a solution obtained by diluting a completely fluorinated ionomer having a sulfonic acid group (5 wt % Nafion solution, manufactured by Aldrich) at a dilution of 1:50 with methanol was added in a sample bottle containing 1 mg of the above electrode catalyst and the mixture was dispersed ultrasonically. 4.4 μL of the obtained suspension solution was dripped on the disk part of the above electrode, followed by drying at room temperature for 12 hours to obtain an electrode for measurement.

[Evaluation of the Oxygen-Reduction Ability of a Rotating Ring Disk Electrode]

The electrode fabricated above was rotated to evaluate the current value of oxygen-reduction reaction at the time. The measurement was made at room temperature in a nitrogen atmosphere and in an oxygen atmosphere, and the value obtained by subtracting the current value measured in a nitrogen atmosphere from the current value measured in an oxygen atmosphere was defined as the oxygen-reduction current value. The measuring device and measuring conditions are as follows.

Measuring Device
    Product manufactured by BAS Inc.
    RRDE-2 rotating ring disk electrode device
    ALS model 701C dual electrochemical analyzer Measuring Condition
    Cell solution: 0.05 mol/L aqueous sulfuric acid solution (oxygen saturated)
    Temperature of solution: 25° C.
    Reference electrode: Silver/Silver chloride electrode (saturated KCl)
    Counter electrode: Platinum wire
    Sweep speed: 5 mV/s
    Electrode rotation speed: 600 rpm FIG. 5 shows the catalytic activity in an oxygen reduction of each of Modified Metal Complex (3B-2), Modified Metal Complex (3F-1) and Modified Metal Complex (3J-1). In this case, the catalyst activity is shown as a value obtained by dividing the current density of the reversible hydrogen electrode at a potential of 0.6 V by the electrode area.

Comparative Example 31

Metal Complex Composition (3L-1) prepared in the foregoing was evaluated in accordance with the method described in Example 35. Table 5 shows the result.

TABLE 5

| | Current Density/mAcm$^{-2}$ |
|---|---|
| Example 35 | 0.165 |
| Example 36 | 0.164 |
| Example 37 | 0.204 |
| Example 31 | 0.045 |

INDUSTRIAL APPLICABILITY

The modified metal complex of the present invention is a modified metal complex excellent in stability (such as acid resistance or thermal stability). Therefore, the catalyst comprising the modified metal complex of the present invention can be preferably used in the synthesis of a polymer compound, or for an additive, a modifier, a cell or a sensor material.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2007-061009 filed in Japan on Mar. 9, 2007, Patent Application No. 2007-084345 filed in Japan on Mar. 28, 2007, and Patent Application No. 2007-205956 filed in Japan on Aug. 7, 2007, each of which is entirely herein incorporated by reference.

The invention claimed is:

1. A modified metal complex obtained by the step of subjecting a metal complex comprising an organic compound having two to six phenol rings and three to eight nitrogen-containing aromatic heterocycles in its molecule as a ligand to any one treatment of a heating treatment, a radiation irradiation treatment and a discharge treatment until a mass reduction rate after the treatment becomes 1 mass % or more and 90 mass % or less, thereby the complex shows a carbon content after the treatment of 5 mass % or more,
   wherein the nitrogen-containing aromatic heterocycles are selected from the group consisting of pyridine, pyrazine, pyridazine, pyrimidine, pyrrole, triazole, pyrazole, thiazole, oxazole, imidazole, indole, benzoimidazole, phenanthroline, carbazole, quinoline, isoquinoline, cinnoline, phthalazine, quinazoline, quinoxaline and benzodiazine, and
   wherein the metal complex comprises metal atom(s) selected from the group consisting of scandium, titanium, vanadium, chromium, manganese, iron, cobalt, nickel, copper, yttrium, zirconium, niobium, molybdenum, ruthenium, rhodium, palladium, silver, lanthanum, cerium, praseodymium, neodymium, samarium, europium, gadolinium, terbium, dysprosium, holmium, erbium, thulium, ytterbium, lutetium, hafnium, tantalum, tungsten, rhenium, osmium, iridium, platinum and gold.

2. The modified metal complex according to claim 1, wherein the number of metal atoms contained in the metal complex is 1 to 10.

3. The modified metal complex according to claim 1, wherein the ligand is a ligand represented by formula (I):

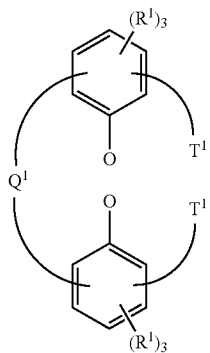

wherein $R^1$ represents a hydrogen atom or a substituent; two $R^1$'s bonded to two adjacent atoms may be coupled with each other, and $R^1$'s may be same as or different from each other; $Q^1$ represents a divalent organic group having at least one nitrogen-containing aromatic heterocycle; $T^1$ represents a monovalent organic group having at least one nitrogen-containing aromatic heterocycle, and two $T^1$'s may be same as or different from each other; and it should be noted that the charge is omitted, and
wherein the substituent is selected from the group consisting of a hydroxyl group, an amino group, a nitro group, a cyano group, a carboxyl group, a formyl group, a hydroxysulfonyl group, a halogen atom, a monovalent hydrocarbon group which may be substituted, a hydrocarbyloxy group which may be substituted, an amino group substituted with two monovalent hydrocarbon groups which may be unsubstituted or substituted, a hydrocarbylmercapto group which may be substituted, a hydrocarbylcarbonyl group which may be substituted, a hydrocarbyloxycarbonyl group which may be substituted, an aminocarbonyl group substituted with two monovalent hydrocarbon groups which may be unsubstituted or substituted and a hydrocarbyloxysulfonyl group which may be substituted.

4. The modified metal complex according to claim 3, which is a polymer comprising a residue of the ligand represented by formula (I).

5. The modified metal complex according to claim 4, which is a polymer comprising the residue of the ligand represented by formula (I) as a repeating unit.

6. The modified metal complex according to claim 1, comprising nitrogen atom and oxygen atom(s) as ligand atom(s).

7. The modified metal complex according to claim 1, which is obtained by heating the metal complex at a temperature of 250° C. or higher and 1,500° C. or lower.

8. The modified metal complex according to claim 1, wherein the metal complex has an absorption local maximum in a range of 1,500 to 1,600 cm$^{-1}$ in a spectrum measured by laser Raman spectrometry at an excitation wavelength of 532 nm.

9. A modified metal complex obtained by the step of subjecting a mixture of the metal complex before the treatment specified in claim 1, and a carbon carrier or at least one organic compound selected from an organic compound having a boiling point or melting point of 250° C. or higher and an organic compound having a thermal polymerization initiation temperature of 250° C. or lower, to any modification treatment of a heating treatment, a radiation irradiation treatment and a discharge treatment until a mass reduction rate after the modification treatment becomes 1 mass % or more and 90 mass % or less, thereby the complex shows a carbon content after the modification treatment of 5 mass % or more.

10. A modified metal complex obtained by the step of subjecting a composition comprising the metal complex before the treatment specified in claim 1, and a carbon carrier and/or a conductive polymer, to a heating treatment, a radiation irradiation treatment or a discharge treatment.

11. A catalyst, comprising the modified metal complex according to claim 1.

12. A carbon compound, which is the modified metal complex according to claim 1, wherein the carbon compound has one or more other peaks at a distance of 0.58 Å or less from a peak derived from a first adjacent atom observed in the range of 1.0 Å or more and 2.5 Å or less in the extended X-ray absorption fine structure (EXAFS) radial distribution function of the central metal of the metal complex.

13. The carbon compound according to claim 12, which has an absorption local maximum in a range of 1,500 to 1,600 cm$^{-1}$ in a spectrum determined by laser Raman spectroscopy at an excitation wavelength of 532 nm.

14. A catalyst, comprising the carbon compound according to claim 12.

15. A catalyst, comprising the modified metal complex according to claim 9.

16. A catalyst, comprising the modified metal complex according to claim 10.

* * * * *